US011299747B2

(12) United States Patent
Park et al.

(10) Patent No.: US 11,299,747 B2
(45) Date of Patent: Apr. 12, 2022

(54) TRANSGENIC PLANTS HAVING ALTERED BIOMASS COMPOSITION

(71) Applicant: Ceres, Inc., Thousand Oaks, CA (US)

(72) Inventors: Joon-Huyn Park, Thousand Oaks, CA (US); Roger I. Pennell, Malibu, CA (US); Richard Flavell, Thousand Oaks, CA (US); Chuan-Yin Wu, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 16/992,793

(22) Filed: Aug. 13, 2020

(65) Prior Publication Data

US 2021/0079420 A1    Mar. 18, 2021

Related U.S. Application Data

(62) Division of application No. 16/406,702, filed on May 8, 2019, now Pat. No. 10,822,616, which is a division of application No. 14/363,151, filed as application No. PCT/US2012/068756 on Dec. 10, 2012, now Pat. No. 10,323,256.

(60) Provisional application No. 61/568,747, filed on Dec. 9, 2011.

(51) Int. Cl.
 *C12N 15/82* (2006.01)
 *C07K 14/415* (2006.01)

(52) U.S. Cl.
 CPC ........ *C12N 15/8297* (2013.01); *C07K 14/415* (2013.01); *C12N 15/8245* (2013.01); *C12N 15/8246* (2013.01); *C12N 15/8261* (2013.01); *Y02A 40/146* (2018.01)

(58) Field of Classification Search
 None
 See application file for complete search history.

(56) References Cited

U.S. PATENT DOCUMENTS

| 4,987,071 | A  | 1/1991  | Cech et al. |
| 5,034,323 | A  | 7/1991  | Jorgensen et al. |
| 5,204,253 | A  | 4/1993  | Sanford et al. |
| 5,231,020 | A  | 7/1993  | Jorgensen et al. |
| 5,254,678 | A  | 10/1993 | Haseloff et al. |
| 5,538,880 | A  | 7/1996  | Lundquist et al. |
| 5,612,191 | A  | 3/1997  | Briggs et al. |
| 5,766,847 | A  | 6/1998  | Jackle et al. |
| 5,773,282 | A  | 6/1998  | Tsusaki et al. |
| 5,874,274 | A  | 2/1999  | Jakobsen et al. |
| 5,878,215 | A  | 3/1999  | Kling et al. |
| 5,939,533 | A  | 8/1999  | Lilja et al. |
| 6,013,863 | A  | 1/2000  | Lundquist et al. |
| 6,090,595 | A  | 7/2000  | Foody et al. |
| 6,198,021 | B1 | 3/2001  | Lange et al. |
| 6,326,527 | B1 | 12/2001 | Kirihara et al. |
| 6,329,571 | B1 | 12/2001 | Hiei |
| 6,333,181 | B1 | 12/2001 | Ingram et al. |
| 6,423,885 | B1 | 7/2002  | Waterhouse et al. |
| PP13,008  | P2 | 9/2002  | Walsh |
| 6,452,067 | B1 | 9/2002  | Bedbrook et al. |
| 6,455,675 | B1 | 9/2002  | Lange et al. |
| 6,573,099 | B2 | 6/2003  | Graham |
| 6,677,502 | B1 | 1/2004  | Allen et al. |
| 6,723,897 | B2 | 4/2004  | Brown et al. |
| PP14,743  | P2 | 5/2004  | Speichert et al. |
| 6,753,139 | B1 | 6/2004  | Baulcombe et al. |
| 6,777,588 | B2 | 8/2004  | Waterhouse et al. |
| PP15,193  | P2 | 9/2004  | Smith et al. |
| 6,906,244 | B2 | 6/2005  | Fischer et al. |
| 6,921,848 | B2 | 7/2005  | Chory et al. |
| 6,921,849 | B2 | 7/2005  | Amasino et al. |
| PP16,176  | P3 | 1/2006  | Cosner et al. |
| 7,049,490 | B2 | 5/2006  | Tanaka et al. |
| 7,059,993 | B2 | 6/2006  | Ding et al. |
| 7,112,429 | B2 | 9/2006  | Ding et al. |
| 7,195,917 | B2 | 3/2007  | Brown et al. |
| PP18,161  | P2 | 10/2007 | Probst |
| 7,420,102 | B2 | 9/2008  | Amasino et al. |
| 7,575,917 | B2 | 8/2009  | Gilbertson et al. |
| 7,807,878 | B2 | 10/2010 | Eriksson et al. |
| 7,915,050 | B2 | 3/2011  | Matsuoka et al. |
| 7,985,888 | B2 | 7/2011  | Phillips et al. |
| 2003/0175783 | A1 | 9/2003 | Waterhouse et al. |
| 2003/0175965 | A1 | 9/2003 | Lowe et al. |
| 2003/0180945 | A1 | 9/2003 | Wang et al. |
| 2003/0217388 | A1 | 11/2003 | Feyereisen et al. |
| 2003/0233670 | A1 | 12/2003 | Edgerton et al. |
| 2004/0214330 | A1 | 10/2004 | Waterhouse et al. |

(Continued)

FOREIGN PATENT DOCUMENTS

| EP | 0534858        | 3/1993  |
| WO | WO 93/16096    | 8/1993  |
| WO | WO 1994/028141 | 12/1994 |
| WO | WO 97/01952    | 1/1997  |
| WO | WO 98/36083    | 8/1998  |

(Continued)

OTHER PUBLICATIONS

Pérez-Flores et al., 2003, Expression analysis of a GA 20-oxidase in embryos from two sorghum lines with contrasting dormancy: possible participation of this gene in the hormonal control of germination, Journal of Experimental Botany 54: 2071-2079.*
U.S. Appl. No. 60/505,689, filed Sep. 23, 2003, Cook, et al.
U.S. Appl. No. 60/518,075, filed Nov. 6, 2003, Pennell, et al.
U.S. Appl. No. 60/544,771, filed Feb. 13, 2004, Cook, et al.
U.S. Appl. No. 60/558,869, filed Apr. 1, 2004, Cook, et al.
U.S. Appl. No. 60/583,609, filed Jun. 30, 2004, Alexandrov.

(Continued)

*Primary Examiner* — Bratislav Stankovic
(74) *Attorney, Agent, or Firm* — Dentons US LLP

(57) ABSTRACT

Methods and materials for modulating biomass composition in plants are disclosed. For example, nucleic acids encoding biomass composition-modulating polypeptides are disclosed as well as methods for using such nucleic acids to transform plant cells. Also disclosed are plants having altered biomass composition and plant products produced from plants having altered biomass composition.

11 Claims, 63 Drawing Sheets

Specification includes a Sequence Listing.

(56) References Cited

U.S. PATENT DOCUMENTS

| | | |
|---|---|---|
| 2005/0032221 A1 | 2/2005 | Chang et al. |
| 2005/0223422 A1 | 10/2005 | Cook et al. |
| 2005/0223434 A1 | 10/2005 | Alexandrov et al. |
| 2005/0229270 A1 | 10/2005 | Fischer et al. |
| 2005/0246785 A1 | 11/2005 | Cook et al. |
| 2006/0010518 A1 | 1/2006 | Feldmann et al. |
| 2006/0015970 A1 | 1/2006 | Pennell et al. |
| 2006/0021083 A1 | 1/2006 | Cook et al. |
| 2006/0041952 A1 | 2/2006 | Cook |
| 2006/0057724 A1 | 3/2006 | Alexandrov et al. |
| 2006/0090216 A1 | 4/2006 | Apuya et al. |
| 2006/0112445 A1 | 5/2006 | Dang |
| 2006/0112454 A1 | 5/2006 | Christensen et al. |
| 2006/0134786 A1 | 6/2006 | Feldmann |
| 2006/0143729 A1 | 6/2006 | Alexandrov et al. |
| 2006/0150285 A1 | 7/2006 | Nadzan et al. |
| 2006/0168696 A1 | 7/2006 | Feldmann et al. |
| 2006/0195943 A1 | 8/2006 | Feldmann et al. |
| 2006/0260004 A1 | 11/2006 | Fang et al. |
| 2006/0265777 A1 | 11/2006 | Apuya et al. |
| 2006/0265788 A1 | 11/2006 | Rommens |
| 2006/0294622 A1 | 12/2006 | Sosa et al. |
| 2007/0006335 A1 | 1/2007 | Cook et al. |
| 2007/0006337 A1 | 1/2007 | Cook et al. |
| 2007/0006345 A1 | 1/2007 | Alexandrov et al. |
| 2007/0006346 A1 | 1/2007 | Alexandrov et al. |
| 2007/0011783 A1 | 1/2007 | Liu et al. |
| 2007/0039067 A1 | 2/2007 | Feldmann et al. |
| 2007/0042387 A1 | 2/2007 | Pennel et al. |
| 2007/0056058 A1 | 3/2007 | Olivier et al. |
| 2007/0061914 A1 | 3/2007 | Feldmann |
| 2007/0083953 A1 | 4/2007 | Christensen et al. |
| 2007/0092935 A1 | 4/2007 | Jones et al. |
| 2007/0094750 A1 | 4/2007 | Jofuku |
| 2007/0101460 A1 | 5/2007 | Feldman et al. |
| 2007/0174936 A1 | 7/2007 | Alexandrov et al. |
| 2007/0192907 A1 | 8/2007 | Alexandrov et al. |
| 2007/0214517 A1 | 9/2007 | Alexandrov et al. |
| 2007/0277269 A1 | 11/2007 | Alexandrov et al. |
| 2008/0072340 A1 | 3/2008 | Troukhan et al. |
| 2008/0131581 A1 | 6/2008 | Schneebergr et al. |
| 2009/0031441 A1 | 1/2009 | Matsuoka et al. |
| 2009/0094717 A1* | 4/2009 | Troukhan ............ C12Q 1/6895 800/290 |
| 2011/0214199 A1 | 9/2011 | Coffin |
| 2019/0323030 A1 | 10/2019 | Park et al. |

FOREIGN PATENT DOCUMENTS

| | | |
|---|---|---|
| WO | WO 98/53083 | 11/1998 |
| WO | WO 99/32619 | 7/1999 |
| WO | WO 02/46449 | 6/2002 |
| WO | WO 2005/098007 | 10/2005 |
| WO | WO 2006/005023 | 1/2006 |
| WO | WO 2006/032916 | 3/2006 |
| WO | WO 2006/034479 | 3/2006 |
| WO | WO 2006/036864 | 4/2006 |
| WO | WO 2007/044988 | 4/2007 |
| WO | WO 2007/046403 | 4/2007 |
| WO | WO 2007/055826 | 5/2007 |
| WO | WO 2007/120989 | 10/2007 |
| WO | WO 2008/049183 | 5/2008 |
| WO | WO 2009/009142 | 1/2009 |
| WO | WO 2009/099899 | 8/2009 |
| WO | WO 2009/102965 | 8/2009 |
| WO | WO 2009/134339 | 11/2009 |
| WO | WO 2009/146015 | 12/2009 |
| WO | WO 2010/033564 | 3/2010 |
| WO | WO 2010/083178 | 7/2010 |
| WO | WO 2010/127969 | 11/2010 |
| WO | WO 2011/011412 | 1/2011 |
| WO | WO 2011/140329 | 11/2011 |
| WO | WO 2012/009551 | 1/2012 |

OTHER PUBLICATIONS

U.S. Appl. No. 60/583,691, filed Jun. 30, 2004, Alexandrov, et al.
U.S. Appl. No. 60/612,891, filed Sep. 23, 2004, Kwok.
U.S. Appl. No. 60/619,181, filed Oct. 14, 2004, Medrano.
U.S. Appl. No. 60/637,140, filed Dec. 16, 2004, Feldmann.
U.S. Appl. No. 60/757,544, filed Jan. 9, 2006, Dang.
U.S. Appl. No. 60/776,307, filed Feb. 24, 2006, Kwok.
Abler, et al., "Isolation and characterization of a genomic sequence encoding the maize Cat3 catalase gene," Plant Molecular Biology, 22:1031-1038 (1993).
Akashi, et al., "Gene Discovery by Ribozyme and siRNA Libraries," Nature Reviews Mol. Cell Biology 6:413-422 (2005).
Alonso-Blanco, et al., "Arabidopsis Protocols," Methods in Molecular Biology 82:137-146 (1998).
Appleford et al., Physiologia Plantarum 100:534-542 (1997).
Aravind and Koonin, "The DNA-repair protein AlkB, EGL-9, and leprecan define new families of 2-oxoglutarate- and iron-dependent dioxygenases," Genome Biol. 2(3):RESEARCH0007 (2001).
Baerson, et al., "Developmental regulation of an acyl carrier protein gene promoter in vegetative and reproductive tissues," Plant Mol. Biol. 22(2):255-267 (1993).
Bateman, et al., "Pfam 3.1: 1313 multiple alignments and profile HMMs match the majority of proteins," Nucl. Acids Res. 27:260-262 (1999).
Bolle, et al., "PAT1, a new member of the GRAS family, is involved in phytochrome A signal transduction," Genes Dev. 14(10):1269-1278 (2000).
Braga, et al., "Expression of the Cry1 Ab Protein in Genetically Modified Sugarcane for the Control of *Diatraea saccharalis* (Lepidoptera: Crambidae)," Journal of New Seeds 5:209-221 (2003).
Burr, et al. "Gene mapping with recombinant inbreds in maize," Genetics 118(3):519-526 (1998).
Burr, et al., "Mapping Genes with Recombinant Inbreds," The Maize Handbook, pp. 249-254(1994).
Bustos, et al., "Regulation of B-Glucuronidase Expression in Transgenic Tobacco Plants by an A/T-Rich, cis-Acting Sequence Found Upstream of a French Bean B-Phaseolin Gene," The Plant Cell 1(9):839-853 (1989).
Cerdan, et al., "A 146 bp fragment of the tobacco Lhcbl*2 promoter confers very-low-fluence and high-irradiance responses of phytochrome to a minimal CaMV 35S promoter," Plant Mol. Biol. 33:245-255 (1997).
Chen, et al., "Functional analysis of regulatory elements in a plant embryo-specific gene," Procedures of the National Academy of Sciences of the United States of America, 83:8560-8564 (1986).
Chenna, et al., "Multiple sequence alignment with the Clustal series of programs," Nucleic Acids Res. 31(13):3497-3500 (2003).
Christian, et al., "Targeting DNA Double-Strand Breaks with TAL Effector Nucleases," Genetics 186:757-761 (2010).
Conceicao, "A cotyledon regulatory region is responsible for the different spatial expression patterns of Arabidopsis 2S albumin genes," The Plant Journal 5(4):493-505 (1994).
Conkling, et al., "Isolation of Transcriptionally Regulated Root-Specific Genes from Tobacco," Plant Physiol. 93:1203-1211 (1990).
Dai, et al., "RF2b, a rice bZIP transcription activator, interacts with RF2a and is involved in symptom development of rice tungro disease," Procedures of the National Academy of Sciences of the United States of America 101(2):687-692 (2004).
De Feyter and Gaudron, "Expressing Ribozymes in Plants," Methods in Molecular Biology 74(43).
Dieffenbach and Dveksler, "PCR Primer: A Laboratory Manual," Cold Spring Harbor Laboratory Press, 520 pages (1995).
Do, et al., "ProbCons: Probabilistic consistency-based multiple sequence alignment," Genome Res. 15(2):330-340 (2005).
Durbin, et al., "Biological Sequence Analysis: Probabilistic Models of Proteins and Nucleic Acids," Cambridge University Press, Cambridge, UK (1998).
Fejes, et al., "A 268 bp upstream sequence mediates the circadian clock-regulated transcription of the wheat Cab-1 gene in transgenic plants," Plant Mol. Biol. 15:921-932 (1990).

(56) References Cited

OTHER PUBLICATIONS

Fromm, et al., "An Octopine Synthase Enhancer Element Directs Tissue-Specific Expression and Binds ASF-1, a Factor from Tobacco Nuclear Extracts," The Plant Cell 1:977-984 (1989).
Fujisawa, et al., "Suppression of the heterotrimeric G protein causes abnormal morphology, including dwarfism, in rice," Procedures of the National Academy of Sciences of the United States of America 96:7575-7580 (1999).
Garcia-Hurtado, et al., "The characterization of transgenic tomato over-expressing gibberellin 20-oxidase reveals induction of parthenocarpic fruit growth, higher yield and alteration of the gibberellin biosynthetic pathway," 30 pages.
Gardiner, et al., "Development of a Core RFLP Map in Maize Using an Immortalized F2 Population," Genetics Society of America 134:917-930 (1993).
GenBank Accession No. L05934 GI: 168436, "Isolation and characterization of a genomic sequence encoding the maize Cat3 catalase gene," dated Oct. 22, 1993, 3 pages.
GenBank Accession No. U93215 GI: 20198323, "*Arabidopsis thaliana* chromosome 2 BAC T6B20 genomic sequence," dated Feb. 27, 2002, 37 pages.
GenBank Accession No. AF129516 GI: 4567094, "Mutations in FIE, a WD polycomb group gene, allow endosperm development without fertilization," dated Apr. 6, 1999, 2 pages.
GenBank Accession No. AF096096 GI: 4185500, "Genes controlling fertilization-independent seed development in *Arabidopsis thaliana*," dated Jan. 25, 1999, 2 pages.
Green, et al., "Binding site requirements for pea nuclear protein factor GT-1 correlate with sequences required for light-dependent transcriptional activation of the rbcS-3A gene," The Embo J. 7:4035-4044 (1988).
Hedden and Phillips, "Gibberellin metabolism: new insights revealed by the genes," Trends Plant Sci. 5(12):523-530 (2000).
Hong, et al., "Promoter sequences from two different *Brassica napus* tapetal oleosin-like genes direct tapetal expression of B-glucuronidase in transgenic Brassica plants," Plant Mol. Biol. 34(3):549-555 (1997).
Hwang, et al., "Aleurone- and embryo-specific expression of the β-glucuronidase gene controlled by the barley Chi26 and Ltp1 promoters in transgenic rice," Plant Cell Reports 20:647-654 (2001).
Hyrup, et al., "Peptide Nucleic Acids (PNA): Synthesis, Properties and Potential Applications," Bioorganic & Medicinal Chemistry 4(1):5-23 (1996).
International Preliminary Reporton Patentability in Application No. PCT/US2012/068756, dated Aug. 19, 2014, 15 pages.
International Search Report and Written Opinion in Application No. PCT/US2012/068756, dated Mar. 19, 2013, 24 pages.
Jordano, et al., "A Sunflower Helianthinin Gene Upstream Sequence Ensemble Contains an Enhancer and Sites of Nuclear Protein Interaction," The Plant Cell 1:855-866 (1989).
Kaneko, et al., "Where do gibberellin biosynthesis and gibberellin signaling occur in rice plants?" The Plant Journal 35:104-115 (2003).
Kasuga, et al., "Improving plant drought, salt, and freezing tolerance by gene transfer of a single stress-inducible transcription factor," Nature Biotechnology 17:287-291 (1999).
Keller and Baumgartner, "Vascular-Specific Expression of the Bean GRP 1.8 Gene is Negatively Regulated," The Plant Cell 3(10):1051-1061 (1991).
Lam, et al., "Site-specific mutations alter in vitro factor binding and change promoter expression pattern in transgenic plants," Procedures of the National Academy of Sciences of the United States of America 86:7890-7894 (1989).
Li, et al., "Small dsRNAs induce transcriptional activation in human cells," Procedures of the National Academy of Sciences of the United States of America 103(46):17337-42 (2006).
Lloyd, et al., "Targeted mutagenesis using zinc-finger nucleases In Arabidopsis," Procedures of the National Academy of Sciences of the United States of America 102:2232-2237 (2005).
Lu, et al., "A study on the application and residues of plant growth regulators in the fruit sugarcane grown in the sub-suitable region," Journal of Agricultural Science 2(4):254-256 (2010).
Luan, et al., "A Rice cab Gene Promoter Contains Separate cis-Acting Elements That Regulate Expression in Dicot and Monocot Plants," The Plant Cell 4:971-981 (1992).
Lubberstedt, et al., "Promoters from Genes for Plastid Proteins Possess Regions with Different Sensitivities toward Red and Blue Light," Plant Physiol. 104:997-1006 (1994).
Martins, et al., "Effects of gibberellin and ethephon on the anatomy of sugar cane plants," Pesq. Agropec. Bras, Brasilia 35(10):1855-1863 (1999).
Matsuoka, et al., "Tissue-specific light-regulated expression directed by the promoter of a C4 gene, maize pyruvate, orthophosphate dikinase, in a C3 plant, rice," Procedures of the National Academy of Sciences of the United States of America, 90:9586-9590 (1993).
Matzke and Birchler, "RNAi-Mediated Pathways in the Nucleus," Nature Reviews Genetics 6:24-35 (2005).
McCallum, et al., "Targeted screening for induced mutations," Nature Biotechnology 18:455-457 (2000).
Medberry, et al., "The Commelina Yellow Mottle Virus Promoter Is a Strong Promoter in Vascular and Reproductive Tissues," The Plant Cell 4(2):185-192 (1992).
Meier, et al., "Elicitor-lnducible and Constitutive in Vivo DNA Footprints Indicate Novel cis-Acting Elements in the Promoter of a Parsley Gene Encoding Pathogenesis-Related Protein 1," The Plant Cell 3:309-316 (1991).
Mittal, "Improving the Efficiency of RNA Interference in Mammals," Nature Reviews Genetics 5:355-365 (2004).
Moore and Haber, "Cell cycle and genetic requirements of two pathways of nonhomologous end-joining repair of double-strand breaks in *Saccharomyces cerevisiae*," Mol Cell Biol. 16(5):2164-2173 (1996).
Murase, et al., "Gibberellin-induced DELLA recognition by the gibberellin receptor GID1," Nature 456(7221):459-463 (2008).
Nardini, et al., "Alpha/beta hydrolase fold enzymes: the family keeps growing," Curr. Opin. Struct. Biol. 9(6):732-737 (1999).
"Nature Reviews RNA interference collection," Nature.Com (2005), Retrieved from Internet http://www.nature.com/focus/rnai/index.html on Apr. 12, 2012, 2 pages.
Oikawa, et al., "A role of OsGA20ox1, encoding an isoform of gibberellin 20-oxidase, for regulation of plant stature in rice," Plant Mol. Biol. 55(5):687-700 (2004).
Ollis, et al., "The alpha/beta hydrolase fold," Protein Eng. 5(3):197-211 (1992).
Perriman, et al., "Effective ribozyme delivery in plant cells," Procedures of the National Academy of Sciences of the United States of America 92(13):6175-6179 (1995).
Pinot and Beisson, "Cytochrome P450 metabolizing fatty acids in plants: characterization and physiological roles," FEBS J. 278(2):195-205 (2011).
Pysh, et al., "The GRAS gene family in Arabidopsis: sequence characterization and basic expression analysis of the SCARECROW-LIKE genes," Plant J. 18(1):111-119 (1999).
Refseth, et al., "Hybridization capture of microsatellites directly from genomic DNA," Electrophoresis 18(9):1519-1523 (1997).
Riggs, et al., "Cotyledon Nuclear Proteins Bind to DNA Fragments Harboring Regulatory Elements of Phytohemagglutinin Genes," The Plant Cell 1(6):609-621 (1989).
Rivera, et al., "Genomic evidence for two functionally distinct gene classes," Procedures of the National Academy of Sciences of the United States of America 95:6239-6244 (1998).
Sheridan, et al., "The macl Gene: Controlling the Commitment to the Meiotic Pathway in Maize," Genetics 142:1009-1020 (1996).
Shibuya, et al., "RNA-directed DNA methylation induces transcriptional activation in plants," Procedures of the National Academy of Sciences of the United States of America 106(5):1660-1665 (2009).
Slocombe, et al., "Temporal and Tissue-Specific Regulation of a *Brassica napus* Stearoyl-Acyl Carrier Protein Desaturase Gene," Plant Physiol. 104(4):167-176 (1994).
Sonnhammer, et al., "Pfam: A Comprehensive Database of Protein Domain Families Based on Seed Alignments," Proteins 28:405-420 (1997).

(56) References Cited

OTHER PUBLICATIONS

Sonnhammer, et al., "Pfam: multiple sequence alignments and HMM-profiles of protein domains," Nucl. Acids Res. 26:320-322 (1998).
Stemple, "TILLING—a high-throughput harvest for functional genomics," Nat Rev Genet 5(2):145-50 (2004).
Summerton and Weller, "Morpholino Antisense Oligomers: Design, Preparation, and Properties," Antisense Nucleic Acid Drug Dev. 7:187-195 (1997).
Tovkach, et al., "A toolbox and procedural notes for characterizing novel zinc finger nucleases for genome editing in plant cells," The Plant Journal 57:747-757 (2009).
Townsend, et al., "High-frequency modification of plant genes using engineered zinc-finger nucleases," Nature 459:442-445 (2009).
Truernit, et al., "The promoter of the *Arabidopsis thaliana* SUC2 sucrose-H+ symporter gene directs expression of B-glucuronidase to the phloem: Evidence for phloem loading and unloading by SUC2," Planta 196:564-570 (1995).
Ueguchi-Tanaka, et al., "Rice dwarf mutant d1, which is defective in the subunit of the heterotrimeric G protein, affects gibberellin signal transduction," Proceedings of the National Academy of Sciences of the United States of America 97(21):11638-11643 (2000).
Urao, "Molecular cloning and characterization of a gene that encodes a MYC-related protein in Arabidopsis," Plant Mol. Biol. 32(3):571-576 (1996).
Vidal, et al. "The ectopic overexpression of a citrus gibberellin 20-oxidase enhances the non-13-hydroxylation pathway of gibberellin biosynthesis and induces an extremely elongated phenotype in tobacco," Physiologia Plantarum 112(2):251-260 (2001).
Voegele, et al., "Members of the gibberellin receptor gene family GID1 (Gibberellin Insensitive DWARF1) play distinct roles during Lepidium sativum and *Arabidopsis thaliana* seed germination," J. Exp. Botany 62(14):5131-5147 (2011).
Vogel and Jung, "Genetic Modification of Herbaceous Plants for Feed and Fuel," Critical Reviews in Plant Sciences 20(1):15-49 (2001).
Weigel, et al., "Activation Tagging in Arabidopsis," Plant Physiology 122:1003-1013 (2000).
Yamamoto, et al., "The Promoter of a Pine Photosynthetic Gene Allows Expression of a B-Glucuronidase Reporter Gene in Transgenic Rice Plants in a Light-Independent but Tissue-Specific Manner," Plant Cell Physiol. 35:773-778 (1994).
Yan, et al., "New Construct Approaches for Efficient Gene Silencing in Plants," Plant Physiol. 141:1508-1518 (2006).
Zhang, et al., "DNA sequences that activate isocitrate lyase gene expression during late embryogenesis and during postgerminative growth," Plant Physiology 110(4):1069-1079 (1996).
Zheng, et al., "SPK1 is an essential S-Phase-Specific gene of *Saccharomyces cerevisiae* that encodes a nuclear serine/threonine/tyrosine kinase," Mol. Cell Biol. 13:5829-5842 (1993).
De Souza et al., 2010, Brazilian Journal of Microbiology 41:850-861.
Sorghum bicolor protein XP_002463483.1, published Jul. 13, 2009.
Keskin et al., 2004, Protein Science 13: 1043-1055.
Guo et al., 2004, Proceedings of the National Academy of Sciences USA 101: 9205-9210.
Thornton et al., 2000, Nature Structural Biology, structural genomic supplement, Nov. 2000: 991-994.
Perez-Flores et al., 2003, Journal of Experimental Botany 54: 2071-2079.
Sorghum bicolor gibberellin 20-oxidase (GA20ox) mRNA, GenBank: AF249881.1, published May 18, 2000.
USPTO: Non-Final Office Action regarding U.S. Appl. No. 16/406,819 dated Jan. 21, 2020.
GenBank Accession No. XM_015776057, Aug. 7, 2018.
GenBank Accession No. XM_025939797 Jul. 27, 2018.
Response to Non-Final Office Action regarding U.S. Appl. No. 16/406,819 filed Mar. 2, 2020.
USPTO: Final Office Action regarding U.S. Appl. No. 16/406,819 dated Mar. 12, 2020.
Response to Final Office Action regarding U.S. Appl. No. 16/406,819 filed Apr. 13, 2020.
USPTO: Advisory Action regarding U.S. Appl. No. 16/406,819 filed Apr. 27, 2020.
Supplemental Response to Final Office Action regarding U.S. Appl. No. 16/406,819 filed Jun. 2, 2020.
Notice of Allowance and Fee(s) Due regarding U.S. Appl. No. 16/406,819, dated Jun. 26, 2020.
Paterson et al., The Sorghum bicolor genome and the diversification of grasses, Nature 547:551-556 (2009).
Sorghum bicolorr polypeptide SORBIDRAFT_01g000580, GenBank accession No. XP_002463483, published Jul. 13, 2009.

* cited by examiner

| SEQ_ID_NO | Sequence | Length |
|---|---|---|
| SEQ_ID_NO_471 | EAALLEEAH RCMDAFFTLP LGEKQRAQRR AGESCGYASS | 120 |
| SEQ_ID_NO_473 | DDALIEQAH RCMDAFFTLP MSDKQRAQRR QGDSCGYASS | 127 |
| SEQ_ID_NO_475 | DAALITAEAH RCMDAFFTLP LPDKQRAQRR QGDSCGYASS | 118 |
| SEQ_ID_NO_476 | DAELLADAH RCVDAFFTMP LPEKQRALRR PGESCGYASS | 118 |
| SEQ_ID_NO_477 | DAELLADAH RCVDAFFTMS LLQGKQRALRR PGESCGYASS | 118 |
| SEQ_ID_NO_478 | DAQLLQDAH RCVDAFFTMP LPEKQRALRR PGESCGYASS | 118 |
| SEQ_ID_NO_479 | DAELLADAH RCVDAFFTMP LPEKQRAQRR PGESCGYASS | 118 |
| SEQ_ID_NO_480 | VDANLISDAQ TYMDLFFELP LSEKQRAQRK AGESCGYASS | 142 |
| SEQ_ID_NO_481 | VDENLISDAH QYMDLFFELP LSDKQRAQRK AGESCGYASS | 138 |
| SEQ_ID_NO_482 | VDASLIADAH RYMDTFFELP LSEKQRAQRK LGEHCGYASS | 137 |
| SEQ_ID_NO_483 | VEANLISNAH RYMDTFFELP LNEKQRARRK LGEHCGYASS | 134 |
| SEQ_ID_NO_484 | VDSSLIADAH RYMDTFFDLP LSEKQRAQRK LGEHCGYASS | 140 |
| SEQ_ID_NO_485 | VDANLIADAH RYMDTFFDMP LRQKQRAQRK LGEHCGYASS | 134 |
| SEQ_ID_NO_487 | VDAKLIYKAH KYMDNFFLLP LAKKQRAQRK LGEHCGYASS | 140 |
| SEQ_ID_NO_488 | VDDKLISNAH QYMDSFFGLP LSEKQRAQRK LGEHCGYASS | 140 |
| SEQ_ID_NO_489 | VNANLIAHAH RYMDMFFDLP LSEKQRAQRK LGEHCGYASS | 140 |
| SEQ_ID_NO_490 | VDKTLISHAH NYVDTFFKLP LSDKQKAERK GESCGYASS | 138 |
| SEQ_ID_NO_491 | VDATLIAHAH RYMDHFFQLP MSAKQRAERK AGEHCGYASS | 145 |
| SEQ_ID_NO_492 | VDDKLIAKAH QYIDYFELP MMVKQRAQRK VGEHCGYASS | 129 |
| SEQ_ID_NO_493 | VDSRLIAKAH EYMEMFFSMP LSEKQRAQRR LGDHCGYASS | 140 |
| SEQ_ID_NO_495 | SEELISDAH EYTSRFFDMP LSEKQRVLRK SGESVGYASS | 150 |
|  |  | 139 |

Figure 1D

| SEQ_ID_NO | | | | | Length |
|---|---|---|---|---|---|
| SEQ_ID_NO_471 | FTGRFASKLP | MKETLSFRYS | SAGDEE---G | EEGVGEYLVR | 157 |
| SEQ_ID_NO_473 | FTGRFASKLP | MKETLSFRYS | D--DQG--D | GDVVVDYFVD | 162 |
| SEQ_ID_NO_475 | FTGRFASKLP | MKETLSFRYT | D--DDGDKS-D | KDVVASYFVD | 156 |
| SEQ_ID_NO_476 | FTGRFASKLP | MKETLSFRSC | P--S---E | PALVVDYIVA | 151 |
| SEQ_ID_NO_477 | FTGRFASKLP | MKETLSFRSC | P--S---D | PDLVVEYIVA | 151 |
| SEQ_ID_NO_478 | FTGRFASKLP | MKETLSFRSC | P--S---D | PALVVDYIVA | 151 |
| SEQ_ID_NO_479 | FTGRFASKLP | MKETLSFRFS | A--EKN---S | ADIVKDYFEN | 151 |
| SEQ_ID_NO_480 | FTGRFSSKLP | MKETLSFQFS | A--DEN---S | SDIVKDYFKD | 177 |
| SEQ_ID_NO_481 | FTGRFSSKLP | MKETLSFQYS | G--EKS---S | ANGVKDYFEN | 173 |
| SEQ_ID_NO_482 | FTGRFSSKLP | MKETLSFRYS | A--EEN---LS | SHIVEEYFQR | 172 |
| SEQ_ID_NO_483 | FTGRFSSKLP | MKETLSFRYS | A--EKS---S | NNIVEDYLLN | 169 |
| SEQ_ID_NO_484 | FTGRFSSKLP | MKETLSFRYS | A--EED---S | SHIVEEYFQR | 176 |
| SEQ_ID_NO_485 | FTGRFSSKLP | MKETLSFSYS | A--ENN---S | SKMVEDYLVN | 169 |
| SEQ_ID_NO_487 | FTGRFSSKLP | MKETLSFRYK | A--EKK---S | SNAVQEYFLN | 175 |
| SEQ_ID_NO_488 | FTGRFSSKLP | MKETLSFRYS | A--EED---S | SHLVEEYFQN | 175 |
| SEQ_ID_NO_489 | FTGRFSTKLP | MKETLSFSFS | A--DKT---S | SKHIEEYFHN | 173 |
| SEQ_ID_NO_490 | FTGRFSSKLP | MKETLSFSFS | A--QPD---SJ | HDIVVDYFQT | 180 |
| SEQ_ID_NO_491 | FKLPMKETLSFRSSL | | D--DNN---F | SNIVQDYLCN | 164 |
| SEQ_ID_NO_492 | FTGRFSSKLP | MKETLSFRYC | D--DMS---R | SNLVQEYFSN | 175 |
| SEQ_ID_NO_493 | FTGRFSTKLP | MKETLSFRFC | | SKSVQDYFCD | 185 |
| SEQ_ID_NO_495 | | | | | 174 |

Figure 1E

| SEQ_ID_NO | Sequence | |
|---|---|---|
| SEQ_ID_NO_471 | KLGAEHGRRL GEVYSRYCHE MSRLSLELME VLGESLGIVG | 197 |
| SEQ_ID_NO_473 | KLGDAYRHH GEVYGRYCSE MSRLSLELME VLGESLGV- | 199 |
| SEQ_ID_NO_475 | KLGEGYLRHH GEVYGRYCSE MSRLSLELME VLGESLGV- | 193 |
| SEQ_ID_NO_476 | TLGEDHLRRL GEVYYRYCSE MSRLSLEIME VLGESLGV- | 188 |
| SEQ_ID_NO_477 | TLGEDHLRRL GEAYARYCSE MSRLSLEIME VLGESLGV- | 188 |
| SEQ_ID_NO_478 | TLGEDHLRRL GEVYARYCSE MSRLSLEIME VLGESLGV- | 188 |
| SEQ_ID_NO_479 | TLGEDHLRRL GEVYARYCSE MSRLSLEIME VLGESLGV- | 188 |
| SEQ_ID_NO_480 | TMGEEFVRL GKVYQEYCNA MSRLSLGIME LLGLSLGV- | 214 |
| SEQ_ID_NO_481 | KMGEEFIRL GNVYQDYCNA MNRLSLGIME LLGMSLGV- | 210 |
| SEQ_ID_NO_482 | TLGKEFTRL GKVYQEYCNA MSRLSLGIME LLGMSLGV- | 209 |
| SEQ_ID_NO_483 | TLGESFNHL GNVYQDYCNS MNTLSLGIME LLGMSLGV- | 206 |
| SEQ_ID_NO_484 | TMGDEFKQF GRVYQDYCES MSRLSLGIME LLAISLGI- | 213 |
| SEQ_ID_NO_485 | KMGNELSHL GNIYQEYCNA MSKLSLGIME LLAISLGV- | 206 |
| SEQ_ID_NO_487 | TLGESFRQL GRVYQDYCEA MSTLSLVIME LLGMSLGI- | 212 |
| SEQ_ID_NO_488 | KMGEDFSEF GQVYQDYCEA MSTLSLGIME LLGMSLGV- | 212 |
| SEQ_ID_NO_489 | TMGESFSHL GNVYQEYCNS MSTLSLGIME LLGMSLGV- | 210 |
| SEQ_ID_NO_490 | RMGEDFAEF GTVYQDYCEA MSNLSLGIME LLGMSLGI- | 217 |
| SEQ_ID_NO_491 | TLGQDFAHI GKIYQEYCNA MSTLSLGIME LLGMSLGV- | 201 |
| SEQ_ID_NO_492 | TMGEDFKPF GKVYQDYCDA MSTLSLRIME LLGMSLGV- | 212 |
| SEQ_ID_NO_493 | VMGEEFRQF GKVYQEYCEA MSTLSLRIME LLGLTLGV- | 222 |
| SEQ_ID_NO_495 | ALGHGFQPF GKVYQEYCEA MSSLSLKIME LLGLSLGV- | 211 |

Figure 1F

| SEQ_ID_NO | Sequence | | | | Length |
|---|---|---|---|---|---|
| SEQ_ID_NO_471 | -DRRHYFRRF | FQRNDSIMRLN | YYPACQRPLD | TLGTGPHCDP | 237 |
| SEQ_ID_NO_473 | -GRRHFRRFF | QGNDSIMRLN | YYPPCQRPYD | TLGTGPHCDP | 238 |
| SEQ_ID_NO_475 | -GRRHFRRFF | QGNDSIMRLN | YYPPCQRPYD | TLGTGPHCDP | 232 |
| SEQ_ID_NO_476 | -GRAHYRRFF | EGNESIMRLN | YYPPCQRPNE | TLGTGPHCDP | 227 |
| SEQ_ID_NO_477 | -GRAHYRRFF | EGNDSIMRLN | YYPPCQRPLE | TLGTGPHCDP | 227 |
| SEQ_ID_NO_478 | -GRAHYRRFF | EGNDSIMRLN | YYPPCQRPYE | TLGTGPHCDP | 227 |
| SEQ_ID_NO_479 | -GRAHYRRFF | EENNSIMRLN | YYPPCQRPYE | TLGTGPHCDP | 227 |
| SEQ_ID_NO_480 | -NRSHFKEFF | QENNSIMRLN | YYPRCQKPEL | TLGTGPHCDP | 253 |
| SEQ_ID_NO_481 | -SRAHFKEFF | EEENDSIMRLN | YYPPCQKPEL | TLGTGPHCDP | 249 |
| SEQ_ID_NO_482 | -HRAHFKEFF | EEENDSIMRLN | YYPRCQKPDQ | TLGTGPHCDP | 248 |
| SEQ_ID_NO_483 | -EKSHFKEFF | EEENDSIMRLN | YYPPCQKPEL | TLGTGPHCDP | 245 |
| SEQ_ID_NO_484 | -GRAHFREFF | DKNDSIMRLN | YYPPCLKPDL | TLGTGPHCDP | 252 |
| SEQ_ID_NO_485 | -ERSHFKEFF | EEENDSIMRLN | YYPPCQKPEL | TLGTGPHCDP | 245 |
| SEQ_ID_NO_487 | -GRAHFREFF | EEENESIMRLN | YYPPCQKPDL | TLGTGPHCDP | 251 |
| SEQ_ID_NO_488 | -GGAHFREFF | NEENDSIMRLN | YYPPCQKPDL | TLGTGPHCDP | 251 |
| SEQ_ID_NO_489 | -GREHFKEFF | QENESIMRLN | YYPPCQKPDL | TLGTGPHCDP | 249 |
| SEQ_ID_NO_490 | -SREHFREFF | EEENESIMRLN | YYPPCRKPDL | TLGTGPHCDP | 256 |
| SEQ_ID_NO_491 | -SEKHFREFY | EEENDSIMRLN | YYPPCQKPDL | TLGTGPHCDP | 240 |
| SEQ_ID_NO_492 | -SQGHYREFF | EGNDSIMRLN | YYPPCQKPDL | TLGTGPHCDP | 251 |
| SEQ_ID_NO_493 | -GRAYFREFF | EGNDSIMRLN | YYPPCQKPDL | TLGTGPHCDP | 261 |
| SEQ_ID_NO_495 | -KRDYFREFF | EEENDSIMRLN | YYPPCLKPDL | TLGTGPHCDP | 250 |

Figure 1G

| SEQ_ID_NO | | | | | | |
|---|---|---|---|---|---|---|
| SEQ_ID_NO_471 | TSLTI LHQDH | VGGLEVVA- | ---- | EGRWRA | IRPRPGALVV | 271 |
| SEQ_ID_NO_473 | TSLTI LHQDD | VGGLQVFDAA | TGPGT | GRWRS | IRPHPGAFVV | 278 |
| SEQ_ID_NO_475 | TSLTI LHQDD | VGGLQVFDAA | ---- | TLAWRS | IRPRPGAFVV | 268 |
| SEQ_ID_NO_476 | TSLTI LHQDN | VGGLQVHT- | ---- | EGRWRS | IRPRADAFVV | 261 |
| SEQ_ID_NO_477 | TSLTI LHQDD | VGGLQVHA- | ---- | DGRWLS | IRPRADAFVV | 261 |
| SEQ_ID_NO_478 | TSLTI LHQDD | VGGLQVHT- | ---- | DGRWRS | IRPRADAFVV | 261 |
| SEQ_ID_NO_479 | TSLTI LHQDN | VGGLEVFV- | ---- | DNEWRS | IRPRADAFVV | 261 |
| SEQ_ID_NO_480 | TSLTI LHQDN | VGGLEVFV- | ---- | DNEWRS | ITPNSNAFVV | 287 |
| SEQ_ID_NO_481 | TSLTI LHQDS | VGGLQVFV- | ---- | DNEWRS | IAPNSQAFVV | 283 |
| SEQ_ID_NO_482 | TSLTI LHQDC | VGGLQVFV- | ---- | DNEWRS | IAPNSNAFVV | 282 |
| SEQ_ID_NO_483 | TSLTI LHQDQ | VGGLQVFV- | ---- | DDEWRS | ITPTFNAFVV | 279 |
| SEQ_ID_NO_484 | TSLTI LHQDR | VGGLQVFV- | ---- | DNEWHS | ISPNFEAFVV | 286 |
| SEQ_ID_NO_485 | TSLTI LHQDQ | VGGLQVFV- | ---- | DNEWRS | ISPNFNAFVV | 279 |
| SEQ_ID_NO_487 | TSLTI LHQDQ | VGGLQVFV- | ---- | DDKWMS | ISPNFEAFVV | 285 |
| SEQ_ID_NO_488 | TSLTI LHQDQ | VGGLQVFV- | ---- | DNEWRS | ISPNFDAFVV | 285 |
| SEQ_ID_NO_489 | TSLTI LHQDQ | VGGLQVFV- | ---- | DNEWRS | ISPNFNAFVV | 283 |
| SEQ_ID_NO_490 | TSLTI LHQDT | VGGLQVFV- | ---- | DNQWRS | INPNFNAFVV | 290 |
| SEQ_ID_NO_491 | TSLTI LHQDQ | VGGLQVFV- | ---- | DEEWRS | IPPNFDAFVV | 274 |
| SEQ_ID_NO_492 | TSLTI LHQDE | VGGLQVFV- | ---- | DEKWHS | ITPNFNAFVV | 285 |
| SEQ_ID_NO_493 | TSLTI LHQDH | VGGLQVFV- | ---- | ENQWRS | VHPDPQAFVV | 295 |
| SEQ_ID_NO_495 | TSLTI LHQDH | VNGLQVFV- | ---- | ENQWRS | IRPNPKAFVV | 284 |

| SEQ_ID | Pos | Seq1 | Seq2 | Seq3 | Seq4 |
|---|---|---|---|---|---|
| SEQ_ID_NO_471 | 311 | NVGDTFMALS | NARYRSCLHR | AVVNSTAPRR | SLAFFLCPEM |
| SEQ_ID_NO_473 | 318 | NIGDTFMALS | NGRYRSCLHR | AVVNSRVPRR | SLAFFLCPEM |
| SEQ_ID_NO_475 | 308 | NIGDTFMALS | NGRYRSCLHR | AVVNSRVARR | SLAFFLCPEM |
| SEQ_ID_NO_476 | 301 | NIGDTFMALS | NGRYKSCLHR | AVVNSKVPRK | SLAFFLCPEM |
| SEQ_ID_NO_477 | 301 | NIGDTFMALS | NGRYKSCLHR | AVVNSRVPRK | SLAFFLCPEM |
| SEQ_ID_NO_478 | 301 | NIGDTFMALS | NGRYKSCLHR | AVVNSRVPRK | SLAFFLCPEM |
| SEQ_ID_NO_479 | 301 | NIGDTFMALS | NGRYKSCLHR | AVVNSRVPRK | SLAFFLCPKK |
| SEQ_ID_NO_480 | 327 | NIGDTFMALS | NGRYKSCLHR | AVVNNKTPRK | SLAFFLCPKK |
| SEQ_ID_NO_481 | 323 | NIGDTFMALS | NGRYKSCLHR | AVVNSKIPRK | SLAFFLCPKK |
| SEQ_ID_NO_482 | 322 | NIGDTFMALS | NGRYKSCLHR | AVVNNRLHRK | SLAFFLCPKK |
| SEQ_ID_NO_483 | 319 | NIGDTFMALS | NGRYKSCLHR | AVVNSQTPRK | SLAFFLCPKN |
| SEQ_ID_NO_484 | 326 | NIGDTFMALS | NGRYKSCLHR | AVVNNKITRK | SLAFFLCPKN |
| SEQ_ID_NO_485 | 319 | NIGDTFMALS | NGRYKSCLHQ | AVVNSQTPRK | SLAFFLCPNK |
| SEQ_ID_NO_487 | 325 | NIGDTFMALS | NGRYKSCLHR | AVVNSHKPRK | SLAFFLCPEG |
| SEQ_ID_NO_488 | 325 | NIGDTFMALS | NGIYRSCLHR | AVVNSQTPRK | SLAFFLCPEK |
| SEQ_ID_NO_489 | 323 | NIGETLMALS | NGKYKSCLHR | AVVNSKSPRK | SLAFFLCPKK |
| SEQ_ID_NO_490 | 330 | NIGDTFMALS | NGRYKSCLHR | AVVNSKTPRK | SLAFFLCPKN |
| SEQ_ID_NO_491 | 314 | NIGDTFMALS | NGIFKSCLHR | AVVNNRTVRK | SLAFFLCPKK |
| SEQ_ID_NO_492 | 325 | NIGDTFMALS | NGIFKSCLHR | AVVNSESERK | SLAFFLCPNM |
| SEQ_ID_NO_493 | 335 | NIGDTFMALS | NDRYKSCLHR | AVVNSESERK | SLAFFLCPKK |
| SEQ_ID_NO_495 | 324 | NIGDTFMALS | NDRYKSCLHR | AVVNSESERK | SLAFFLCPKK |

| SEQ ID | Sequence | # |
|---|---|---|
| SEQ_ID_NO_471 | DTVVRPPEEL VDD-HHPRVY PDFTWRALLD FTQRHYRADM | 350 |
| SEQ_ID_NO_473 | DKVVRPPAEL VDD-ANPRAY PDFTWRTLLD FTMRHYRSDM | 357 |
| SEQ_ID_NO_475 | DKVVRPPKEL VDD-ANPRAY PDFTWRTLLD FTMRHYRSDM | 347 |
| SEQ_ID_NO_476 | DKVVAPPGTL VDA-ANPRAY PDFTWRSLLD FTQKHYRADM | 340 |
| SEQ_ID_NO_477 | DKVVAPPETL VDE-ANPRAY PDFTWRALLD FTQKHYRADM | 340 |
| SEQ_ID_NO_478 | DKVVAPPGTL VDA-ANPRAY PDFTWRSLLD FTQKHYRADM | 340 |
| SEQ_ID_NO_479 | DKVVSPPKEL VDE-NNPRVY PDFTWATFLE FTQKHYRADM | 340 |
| SEQ_ID_NO_480 | DKVVSPPEKL VDQ-KNPRIY PDFTWSTFLE FTQKHYRADM | 366 |
| SEQ_ID_NO_481 | DKVVSPPDEL VDE-NNPRIY PDFTWSTFLE FTQKHYRADM | 362 |
| SEQ_ID_NO_482 | DKVVSPPSEL VDS-NNPRIY PDFTWPTLLE FTQKHYRADM | 361 |
| SEQ_ID_NO_483 | DKVVSPPSKL VDS-SSPRIY PDFTWPMLLE FTQKHYRADM | 358 |
| SEQ_ID_NO_484 | DKVVTPPAEL VSQ-NNPRMY PDFTWPTLHE FTQKHYRADM | 366 |
| SEQ_ID_NO_485 | DKVVRPPTEL VDT-NSPRVY PDFTWPMLLE FTQKHYRADM | 358 |
| SEQ_ID_NO_487 | DKVVSPPTEL VDT-NSPRIY PDFTWSNLLE FTQKHYRADM | 364 |
| SEQ_ID_NO_488 | DKVVSPPIEL VDT-NNPRIY PDFTWPMLLE FTQKHYRADM | 364 |
| SEQ_ID_NO_489 | DKMVTPPHEL VDT-CNPRIY PDFTWPTLLE FTQKHYRADM | 362 |
| SEQ_ID_NO_490 | DKVVRPPNEL VDS-SNPRVY PDFTWPTLLE FTQKHYRADM | 369 |
| SEQ_ID_NO_491 | DKVVSPPSEL VDS-LOPRVY PDFTWPMLLE FTQKHYRADM | 353 |
| SEQ_ID_NO_492 | EKVVKPPKNL VDS-NNPRLY PDFTWPALLE FTQKHYRADV | 364 |
| SEQ_ID_NO_493 | DKVVTPPREL LDS-ITSRRY PDFTWPMLLE FTQKHYRADM | 374 |
| SEQ_ID_NO_495 | DRVVTPPREL LDS-ITSRRY PDFTWSMFLE ETQKHYRADM | 363 |

Figure 1J

| SEQ ID | Seq A | Seq B | Seq C | # |
|---|---|---|---|---|
| SEQ_ID_NO_471 | RTLQAFSDWL | NHHRHL | QPTI YS | 372 |
| SEQ_ID_NO_473 | RTLEAFSNWL | NHGGHL | SSPPPP | 379 |
| SEQ_ID_NO_475 | RTLEAFSNWL | STSSNGGQ | HLLEKK | 371 |
| SEQ_ID_NO_476 | KTLEVFSDWL | VQQQQGQLL | PPLASH | 365 |
| SEQ_ID_NO_477 | KTLEVFSSWM | QQGHQP-A- | ATTTTT | 363 |
| SEQ_ID_NO_478 | KTLEVFSDWM | VQQQP----- | -ASART | 360 |
| SEQ_ID_NO_479 | KTLEVFSSWV | VQQQ------ | QAAMT | 359 |
| SEQ_ID_NO_480 | KTLQAFSNWV | EQK------- | TSTT | 383 |
| SEQ_ID_NO_481 | NTLQAFSNWM | QQE------- | TSRT | 379 |
| SEQ_ID_NO_482 | NTLKAFSNWL | QQK------- | NS | 376 |
| SEQ_ID_NO_483 | NTLQAFSNWL | QHNTI----- | TAQL | 376 |
| SEQ_ID_NO_484 | NTLQTFSNWL | QQK------- | KQLK | 383 |
| SEQ_ID_NO_485 | KTLEAFTNWL | QHS------- | TAQA | 375 |
| SEQ_ID_NO_487 | NTLANFSNWL | QQR------- | NS | 379 |
| SEQ_ID_NO_488 | NTLQEFSNWV | QQKT------ | AEAG | 382 |
| SEQ_ID_NO_489 | KTLEVFSSWL | QQK------- | LAQV | 379 |
| SEQ_ID_NO_490 | NTLQTFSNWL | QQK------- | SLS | 385 |
| SEQ_ID_NO_491 | KTLEVFTNWL | HQR------- | PNKTI | 372 |
| SEQ_ID_NO_492 | NTLQSFSTML | ASTH------ | NS | 379 |
| SEQ_ID_NO_493 | KTLEVFSNWL | QQK------- | KS | 389 |
| SEQ_ID_NO_495 | KTLDVFANWL | QQK------- | PI | 377 |
| SEQ_ID_NO_495 | NTLQAFSDWL | TKF------- | | |

| SEQ_ID_NO | | | | | | |
|---|---|---|---|---|---|---|
| SEQ_ID_NO_99 | EHRYPCAYDD | GWTALKWMS | QPFMRSGG-- | DAQARVFLSG | 196 |
| SEQ_ID_NO_101 | EHRYPCAYDD | GWAALKWAMS | QPFLRSGE-- | GAQPRVFLSG | 198 |
| SEQ_ID_NO_103 | EHRYPCAYDD | GWTALKWAMS | QPFLRSGRGG | DARPRVFLSG | 199 |
| SEQ_ID_NO_104 | EHRYPCAYDD | GWTALKWAMS | QPFLRSGE-- | DAQPRVFLSG | 197 |
| SEQ_ID_NO_105 | EHRYPCAYED | GWAALKWAQA | QPFLRSGA-- | DARPRVFLSG | 197 |
| SEQ_ID_NO_106 | EHRYPCAYDD | GWAALKWAQA | QPFLRSGS-- | DARLRVFLAG | 198 |
| SEQ_ID_NO_107 | EHRYPCAYDD | GWTALKWATS | QPFLRSGG-- | DGRPRVFLSG | 198 |
| SEQ_ID_NO_108 | ENRYPCAYDD | GWTALKWNS | RPWLQSQK- | DSKVHIYLAG | 193 |
| SEQ_ID_NO_110 | ENRYPCAYDD | GWAALKWNS | RTWLESKK- | DSKVHIYLAG | 188 |
| SEQ_ID_NO_111 | EHRYPCAYDD | GWAALKWKS | RSWLQSGK- | DAKVHMYLAG | 188 |
| SEQ_ID_NO_112 | EHRYPCAYDD | GWNALKWKS | RVMLQSGK- | DSKVHVYLAG | 188 |
| SEQ_ID_NO_113 | EHRYPCAYDD | GWNALKWKS | KWLQSGK- | DSNYYLAG | 188 |
| SEQ_ID_NO_114 | EFRYPCAYED | GWTALKWHS | RPWLHSGK- | DSKVHVYLAG | 188 |
| SEQ_ID_NO_115 | ENRYPSAYDD | GWAALKWHS | RPWLHSGK- | DSKAYVYLAG | 190 |

| SEQ_ID_NO | | | | | | |
|---|---|---|---|---|---|---|
| SEQ_ID_NO_99 | DSSGGNIAHH | VAVRAADEGV | KVCGNILLNA | MFGGTERTES | 236 |
| SEQ_ID_NO_101 | DSSGGNIAHH | VAVRAADAGI | RICGNILLNA | MFGGTERTDS | 238 |
| SEQ_ID_NO_103 | DSSGGNIAHH | VAVRAADAGI | NICGNILLNA | MFGGTERTES | 239 |
| SEQ_ID_NO_104 | DSSGGNIAHH | VAVRAAEEGI | KIHGNILLNA | MFGGKERTES | 237 |
| SEQ_ID_NO_105 | DSSGGNIAHH | VAVRAAEEGI | SICGNILLNA | MFGGVERTES | 237 |
| SEQ_ID_NO_106 | DSSGGNIAHH | VAVRAADAGI | KIHGNILLNA | MFGGTERTES | 238 |
| SEQ_ID_NO_107 | DSSGGNIAHH | VALRAIESGI | DILGSILLNA | MFGGQERTES | 233 |
| SEQ_ID_NO_108 | DSSGGNIVHH | VALRAVESGI | DVLGNILLNP | MFGGQERTES | 228 |
| SEQ_ID_NO_110 | DSSGGNIVHH | VALRAIESGI | EVLGNILLNP | MFGGQERTES | 228 |
| SEQ_ID_NO_111 | DSSGGNITHH | VAVRAITNEGV | KVLGNILLHP | MFGGLERTES | 228 |
| SEQ_ID_NO_112 | DSSGGNIAHH | VAARAAEED | EVLGNILLHP | MFGGEKRTES | 228 |
| SEQ_ID_NO_113 | DSSGGTLAHH | VAHRAAESGV | EVLGNILLHP | MFGGQERTQS | 230 |

```
SEQ_ID_NO_99   ERRLDGKYFV TLQDRDWYVK AYLPEDADRD HPACNPFGPN 276
SEQ_ID_NO_101  ERRLDGKYFV TLQDRDWYVK AYLPEDADRD HPACNPFGPN 278
SEQ_ID_NO_103  ERRLDGKYFV TLQDRDWYVK AYLPEDADRD HPACNPFGPN 279
SEQ_ID_NO_104  ERRLDGKYFV TLQDRDWYVK AYLPEDADRD HPACNPFGPN 277
SEQ_ID_NO_105  ERRLDGKYFV TLQDRDWYVK AYLPEDTDRD HPACNPFGPN 277
SEQ_ID_NO_106  ERRLDGKYFV TMQDRDWYVK AYLPEDADRD HPACNPFGPN 278
SEQ_ID_NO_107  ERRLDGKYFV TLQDRDWYVK AYLPEGEDRD HPACNPFGPN 273
SEQ_ID_NO_108  ERRLDGKYFV TLRDRDWYVR AYLPEREDRD HPACNPFGPN 268
SEQ_ID_NO_110  EKRLDGKYFV TLQDRDWYVR AFLPEEADRD HPACNPFGPK 268
SEQ_ID_NO_111  EKRLDGKYFV TLQDRDWYVR AFLPEGEDRD HPACNPFGPK 268
SEQ_ID_NO_112  EKRLDGKYFV TVQDRDWYVR AYLPEGEDRD HPACNPFGPR 268
SEQ_ID_NO_113  EKRLDGKYFV TIQDRDWYVR AYLPEGEDRD HPACNPLFGPK 268
SEQ_ID_NO_114  EKKLDGKYFV TIHDRDWYVR AYLPEGEDRD HPACNPFGPK 268
SEQ_ID_NO_115  EKKLDGKYFV TIQDRDWYVR AYLPEGEDRD HPACNPFGPR 270

SEQ_ID_NO_99   GRRLGGLPFA KSLIIVSGLD LTCDRQLAYA DALREDGHHV 316
SEQ_ID_NO_101  GRRLRGLPFT KSLIIVSGLD LTCDRQLAYA EGLREDGHHA 318
SEQ_ID_NO_103  GRRLRGLPFT KSLIIVSGLD LTCDRQLAYA EGLQEDGHHV 319
SEQ_ID_NO_104  GRRLRGLPFA KSLIIVSGLD LTCDRQLGYA EGLREDGHHV 317
SEQ_ID_NO_105  GRRLKGLPFA KSLIIVSGLD LTCDRQLGYA EGLREDGHDV 317
SEQ_ID_NO_106  GRRLRGLPFA KSLIIVSGLD LTCDRQLAYA EGLQQDGHHV 318
SEQ_ID_NO_107  GRRLRGLPFP KSLVVVAGLD LTCDRQLAYA EGLKKAGQEV 313
SEQ_ID_NO_108  GRSLEGIKFP KSLVVVAGLD LIQDWQLAYA EGLKKAGQDV 308
SEQ_ID_NO_110  GKSLEGIKFP KSLVVVAGLD LVHDRQITYA EGLKKAGQDV 308
SEQ_ID_NO_111  GRSLEGMKFP KSLVVVAGED LIQDWQLAYV EGLKKAGQMV 308
SEQ_ID_NO_112  GKSLEGVNFP KSLVVVAGLD LVQDWQLAYV EGLKAGQDV 308
SEQ_ID_NO_113  GQSLEGINFP KSLVVVAGLD LIQDWQLAYV DGLKRTGHHV 308
SEQ_ID_NO_114  AKSLEGINFP KSLVVVAGLD LMQDWQLAYV QGLKNSGHDV 308
SEQ_ID_NO_115  GVSLEGLSFP KSLVVVAGLD LVQDWQLAYV EGLKNAGQEV 310
```

Figure 2E

| SEQ_ID_NO | Sequence (part 1) | Sequence (part 2) | Sequence (part 3) | Sequence (part 4) | Pos |
|---|---|---|---|---|---|
| SEQ_ID_NO_99  | KVVQCENATV | GFYLLPNTVH | YHEVMEEISD | FLNA- | 350 |
| SEQ_ID_NO_101 | KLVYREKATI | GFYLLPNTDH | YHEVMEEISD | FLGA- | 352 |
| SEQ_ID_NO_103 | KLVYREKATI | GFYLLPNTDH | YHEVMEEIAD | FLRA- | 353 |
| SEQ_ID_NO_104 | KVVHREKATI | GFYLLSNTDH | YHEVMEEIAD | FVQL- | 351 |
| SEQ_ID_NO_105 | KLVYREKATI | GFYLLSNTDH | YHEVMEEIAD | FLRA- | 351 |
| SEQ_ID_NO_106 | KLVYREKATI | GFYLLSNTNH | YHEVMEEIAE | FVRA- | 352 |
| SEQ_ID_NO_107 | KVVYREKATI | GFYLLPNTDH | YHEVMEEIGD | FLAA- | 347 |
| SEQ_ID_NO_108 | KLLYVEQATI | GFYLLPNNHH | FHTVMDEISK | FVSS- | 342 |
| SEQ_ID_NO_110 | KLLYLEQATI | GFYLLPNNNY | FHTVMDEISE | FVSP- | 342 |
| SEQ_ID_NO_111 | KLLYLEQATI | GFYLLPNNNH | FHTVMDEISE | FVCP- | 342 |
| SEQ_ID_NO_112 | NLLFLEQATI | GFYLLPNNDH | FYCLMEEIKN | FVKS- | 342 |
| SEQ_ID_NO_113 | NLLYLKQATI | GFYFLPNNDH | FHCLMDELTK | FVHSI DEDSQ | 348 |
| SEQ_ID_NO_114 | KLLFLEQATI | GFYFLPNNEH | FYCLMEEIDN | FIN-- | 341 |
| SEQ_ID_NO_115 | KLLFLKQATI | GFYFLPNNDH | EYMLMEEINS | EVNP- | 344 |

| SEQ_ID_NO | Sequence | Pos |
|---|---|---|
| SEQ_ID_NO_99  | --------NL------YY----- | 354 |
| SEQ_ID_NO_101 | --------NL------L-L---- | 355 |
| SEQ_ID_NO_103 | --------NE------R------ | 355 |
| SEQ_ID_NO_104 | --------NL------L-L---- | 354 |
| SEQ_ID_NO_105 | --------NL------L-L---- | 353 |
| SEQ_ID_NO_106 | --------NL------L------ | 355 |
| SEQ_ID_NO_107 | --------NL------L-C---- | 349 |
| SEQ_ID_NO_108 | --------DL--------C---- | 344 |
| SEQ_ID_NO_110 | --------NL--------C---- | 344 |
| SEQ_ID_NO_111 | --------NL--------C---- | 344 |
| SEQ_ID_NO_112 | --------NL--------P---- | 344 |
| SEQ_ID_NO_113 | SKSSPVLLT---------P---- | 358 |
| SEQ_ID_NO_114 | --------NL------------- | 342 |
| SEQ_ID_NO_115 | --------NL--------C---- | 346 |

Figure 2E

| SEQ ID | Sequence | # |
|---|---|---|
| SEQ_ID_NO_188 | MKREYQEAGG SSGGG---------SS--ADM G-SCKDKVMA | 29 |
| SEQ_ID_NO_221 | MKREYQEAGG SSGGG---------SS--ADM G-SCKDKVMA | 29 |
| SEQ_ID_NO_201 | MKREYQDAGG SGG-------------DM G-SSKDKMMA | 24 |
| SEQ_ID_NO_194 | MKREYQDAGG SGG-------------DM G-SSKDKMMA | 24 |
| SEQ_ID_NO_215 | MKREYQDAGG SGGG------------DM G-SSKDKMMA | 24 |
| SEQ_ID_NO_202 | MKREYQDAGG SGGGG-----------DM G-SSKDKMMV | 27 |
| SEQ_ID_NO_207 | MKREYQDAGG SGGG-----------DEM G-SSKDKMMV | 24 |
| SEQ_ID_NO_283 | MKREYQDAGG SGGG------------DM G-SSRDKMMV | 27 |
| SEQ_ID_NO_196 | MKRDLLDGCG GGGGG----GGGK GEEG- GGM V-SAKGKMWD | 36 |
| SEQ_ID_NO_235 | MKRDHQETIG GAGNSI GNKA ESSS- SSM A-TGKGKLW | 36 |
| SEQ_ID_NO_245 | MKRDFQQACA GGPV-----K G-DS- SSM P-NGKAKMWE | 30 |
| SEQ_ID_NO_286 | MKRDHRDSRA TVTARENNSK PEYSsPP SSA L-NGKAKIWE | 39 |
| SEQ_ID_NO_282 | MKRDHRDSCG GGGG--SVK GEC- SSM PS NGKANMWE | 34 |
| SEQ_ID_NO_239 | MKREHQESKG DSS--------- SCS A-MAKGKLWQ | 26 |
| SEQ_ID_NO_277 | MKRDRDRE REKR--------- AFSN- GAV S-SGKSKIWE | 30 |

| SEQ ID | Sequence | # |
|---|---|---|
| SEQ_ID_NO_188 | GAA------- EEEDVDELLA ALGYKVRSSD MADVAQKLEQ | 63 |
| SEQ_ID_NO_221 | GAA---G--- EEEDVDELLA ALGYKVRSSD MADVAQKLEQ | 63 |
| SEQ_ID_NO_201 | AAA----EL- QDEEDVDELLA ALGYKVRSSD MADVAQKLEQ | 59 |
| SEQ_ID_NO_194 | AAAGAG--EQ EEEDVDELLA ALGYKVRASD MADVAQKLEQ | 62 |
| SEQ_ID_NO_215 | AAAGAG--EL- QEEELDEMLA SLGYKVRSSD MADVAQKLEQ | 61 |
| SEQ_ID_NO_202 | SSSEAG---- EGEEEMDELLA AVGYKVRASD MADVAQKLEQ | 63 |
| SEQ_ID_NO_207 | AAAGAG--EL- QEEEVDELLA AVGYKVRSSD MADVAQKLEQ | 61 |
| SEQ_ID_NO_283 | SAA----Q- EGEEVDELLA VLGYKVRSSD MADVAQKLEQ | 62 |
| SEQ_ID_NO_196 | DGG----Q- DAGGDMDELLA VLGYNVRSSD MVDVAQKLEQ | 70 |
| SEQ_ID_NO_235 | EDD----RH- AGGGMDELLA VLGYKIKSSE MADVAQKLEQ | 70 |
| SEQ_ID_NO_245 | EDL----DG- QQGGMDELLA ALGYKVRSSD MADVAQKLEQ | 65 |
| SEQ_ID_NO_286 | DDQ----YS- AGGDMDELLA VLGYKVRSSD MADVAQKLEQ | 76 |
| SEQ_ID_NO_282 | EQQ----Q- QQQGMDELLA ALGYKVRSDD MADVAQKLEQ | 68 |
| SEQ_ID_NO_239 | EEE-EQQQ-- DGGGMDELLA VLGYKVRSSD MAEVAQKLEQ | 64 |
| SEQ_ID_NO_277 | EDE-E-EK- PDAGMDELLA VLGYKVKSSD MADVAQKLEQ | 66 |

| | | | | | | |
|---|---|---|---|---|---|---|
| SEQ_ID_NO_188 | GGGASRGSVV | EAAPP- | ---- | -ATQ- | GAAAANAPAV | 227 |
| SEQ_ID_NO_221 | GGGASRGSVV | EAAPP- | ---- | -AMQ- | GAAAANAPAV | 227 |
| SEQ_ID_NO_201 | DGGRTRSSVV | EAAPP- | ---- | -ATQ- | ASAAANAPAV | 225 |
| SEQ_ID_NO_194 | DGGRTRSSVV | EAAPP- | ---- | -ATQ- | ASAAANGPAV | 229 |
| SEQ_ID_NO_215 | DGGRTRSSVV | EAAPP- | ---- | -ATQ- | APAAANGPAV | 231 |
| SEQ_ID_NO_202 | GGGAARSSVV | EAAPP- | ---- | -VAL- | -AAAAAPAL | 216 |
| SEQ_ID_NO_207 | DGGRTRSSVV | EAAPP- | ---- | -ATQ- | ASAAANGPAV | 222 |
| SEQ_ID_NO_283 | GGG-ARSSVV | EAAPP- | ---- | -VAL- | -AAAANTPAL | 220 |
| SEQ_ID_NO_196 | QSSNS-SCTP | SSSPQ- | ---- | -EN | GLASVAESTR | 217 |
| SEQ_ID_NO_235 | TVATT-NTQTV | EELEPG- | -TN | -AIMA | VSGTLSEPTR | 223 |
| SEQ_ID_NO_245 | ---------- | ------ | ---- | KRLKASPIE- | SSESASEPTR | 212 |
| SEQ_ID_NO_286 | ---------- | ------ | ---- | ---- | GAVSDPTR | 204 |
| SEQ_ID_NO_282 | ---------- | ------ | ---- | KRLKPSPME- | SADSASEPTR | 195 |
| SEQ_ID_NO_239 | -NNNL ---- | DELETANNI | N | ---- | PTNLSEPNR | 186 |
| SEQ_ID_NO_277 | ---------- | ------ | ---- | ---- | MVTDSSATR | 185 |

| | | | | | | |
|---|---|---|---|---|---|---|
| SEQ_ID_NO_188 | PVVVVDTQEA | GIRLVHALLA | CAEAVQQENF | AAAEALVKQI | 267 |
| SEQ_ID_NO_221 | PVVVVDTQEA | GIRLVHALLA | CAEAVQQENF | AAAEALVKQI | 267 |
| SEQ_ID_NO_201 | PVVVVDTQEA | GIRLVHALLA | CAEAVQQENF | TAAEALVKQI | 265 |
| SEQ_ID_NO_194 | PVVVVDTQEA | GIRLVHALLA | CAEAVQQENF | SAAEALVKQI | 269 |
| SEQ_ID_NO_215 | PVVVVDTQEA | GIRLVHALLA | CAEAVQQENF | SAADALVKQI | 271 |
| SEQ_ID_NO_202 | PVVVVMDTQEA | GIRLVHALLA | CAEAVQQENL | SAAEALVKQI | 256 |
| SEQ_ID_NO_207 | PVVVVMDTPEA | GIRLVHALLA | CAEAVQQENL | SAADALVKQI | 262 |
| SEQ_ID_NO_283 | PVVVVDSQET | GVRLVHTLLA | CADAVQQDNM | SAADALVKQI | 260 |
| SEQ_ID_NO_196 | PVVVVDSQEA | GVRLVHTLMA | CAEAIQQENL | SAAEALVKHI | 257 |
| SEQ_ID_NO_235 | PVVLIDSQET | GVRLVHTLLA | CAEAVQQENL | KLADALVKHI | 263 |
| SEQ_ID_NO_245 | PVVLVDSQEA | GVRLVHTLLA | CAEAVQQENL | KLADALVKHV | 252 |
| SEQ_ID_NO_286 | PRVLVDHQEA | GVRLVHTLLA | CAEAVQQENL | KLADALVKHV | 244 |
| SEQ_ID_NO_282 | TVLLVDSQET | GVRLVHTLLA | CAEAVQQENL | KLADALVKHI | 235 |
| SEQ_ID_NO_239 | PMVLIDSQET | GVRLVHTLMA | CAEAIQQDNF | KLAEALLKHI | 226 |
| SEQ_ID_NO_277 | PVVLVDSQET | GVRLVHTLMA | CAEAVQQENL | TLADQLVRHI | 225 |

Figure 3D

| | | | | | | |
|---|---|---|---|---|---|---|
| SEQ_ID_NO_188 | PTLAASQGGA | MRKVAAYFGE | ALARRVYRFR | PA_DSTLLDA | 306 |
| SEQ_ID_NO_221 | PTLAASQGGA | MRKVAAYFGE | ALARRVYRFR | PA_DSTLLDA | 306 |
| SEQ_ID_NO_201 | PMLASSQGGA | MRKVAAYFGE | ALARRVYRFR | PAPDSLLDA  | 305 |
| SEQ_ID_NO_194 | PMLASSQGGA | MRKVAAYFGE | ALARRVYRFR | PPPDSSLLDA | 309 |
| SEQ_ID_NO_215 | PLLASSQGGA | MRKVAAYFGE | ALARRVYRFR | PTPDTSLLDA | 311 |
| SEQ_ID_NO_202 | PMLASSQGGA | MRKVAAYFGE | ALARRVFRFR | PQPDSSLLDA | 296 |
| SEQ_ID_NO_207 | PLLASSQGGA | MRKVAAYFGE | ALARRVFRFR | PTPDSLLDA  | 302 |
| SEQ_ID_NO_283 | PMLASSQGGA | MRKVATYFAE | ALARRIYRIY | PQDF_SLES  | 300 |
| SEQ_ID_NO_196 | GLLAASQAGA | MRKVATYFAQ | ALARRIYKIF | PQDF_HCLDS | 294 |
| SEQ_ID_NO_235 | GVLAASQAGA | MRKVATYFAE | ALARRIYGIF | PEE_TLES   | 301 |
| SEQ_ID_NO_245 | GILAASQAGA | MRKVATYFAQ | ALARRIYRIY | PQD_CLDS   | 289 |
| SEQ_ID_NO_286 | GILAASQTGA | MRKVATYFAE | ALARRIYGIF | PEE_SLDP   | 281 |
| SEQ_ID_NO_282 | GILAASQAGA | MRKVASYFAE | ALARRIYKIY | PQE_SLDP   | 272 |
| SEQ_ID_NO_239 | GLLAASQASs | MRKVATYFAE | ALARRIYKIY | PQD_SMES   | 263 |
| SEQ_ID_NO_277 | GILAVSQSGA | MRKVATYFAE | ALARRIYKIY | PQD_SMES   | 262 |

| | | | | | | |
|---|---|---|---|---|---|---|
| SEQ_ID_NO_188 | AFADLLHAHF | YESCPYLKFA | HFTANQAILE | AFAGCHRVHV | 346 |
| SEQ_ID_NO_221 | AFADLLHAHF | YESCPYLKFA | HFTANQAILE | AFAGCRRVHV | 346 |
| SEQ_ID_NO_201 | AFADLLHAHF | YESCPYLKFA | HFTANQAILE | AFAGCRRVHV | 345 |
| SEQ_ID_NO_194 | AFADLLHAHF | YESCPYLKFA | HFTANQAILE | AFAGCRRVHV | 349 |
| SEQ_ID_NO_215 | AVADFLHAHF | YESCPYLKFA | HFTANQAILE | AFAGCRRVHV | 351 |
| SEQ_ID_NO_202 | AVADFLHAHF | YESCPYLKFA | HFTANQAILE | AFAGCRRVHV | 336 |
| SEQ_ID_NO_207 | AFADFLHAHF | YEACPYLKFA | HFTANQAILE | AFAGANRVHV | 342 |
| SEQ_ID_NO_283 | SYSDILQMHF | YETCPYLKFA | HFTANQAILE | AFANASRVHV | 340 |
| SEQ_ID_NO_196 | SYSDTLEMHF | YESCPYLKFA | HFTANQAILE | AFATAGRVHV | 334 |
| SEQ_ID_NO_235 | SLsDLLHMHF | YETCPYLKFA | HFTANQAILE | AFATASRVHV | 341 |
| SEQ_ID_NO_245 | SFSDVLHMHF | YESCPYLKFA | HFTANQAILE | AFATAGRVHV | 329 |
| SEQ_ID_NO_286 | SYSDTLEMHF | YETCPYLKFA | HFTANQAILE | AFA_TANRVHV | 321 |
| SEQ_ID_NO_282 | SYSDVLQMHF | YESCPYLKFA | HFTANQAILE | AFGTANRVHV | 312 |
| SEQ_ID_NO_239 | SFSDVLHMHF | YESCPYLKFA | HFTANQAILE | AFGTANRVHV | 303 |
| SEQ_ID_NO_277 | SYTDVLQMHF | YETCPYLKFA | HFTANQAILE | AETGCNKVHV | 302 |

Figure 3E

| SEQ_ID_NO_188 | VDFGI KQGMQ | WPALL QALAL | RPGGPPS FRL | TGVGPPPQPDE | 386 |
|---|---|---|---|---|---|
| SEQ_ID_NO_221 | VDFGI KQGMQ | WPALL QALAL | RPGGPPS FRL | TGVGPPPQPDE | 386 |
| SEQ_ID_NO_201 | VDFGI KQGMQ | WPALL QALAL | RPGGPPS FRL | TGVGPPPQPDE | 385 |
| SEQ_ID_NO_194 | VDFGI KQGMQ | WPALL QALAL | RPGGPPS FRL | TGVGPPPQPDE | 389 |
| SEQ_ID_NO_215 | VDFGI KQGMQ | WPALL QALAL | RPGGPPS FRL | TGVGPPPQPDE | 391 |
| SEQ_ID_NO_202 | VDFGI KQGMQ | WPALL QALAL | RPGGPPS FRL | TGVGPPPQPDE | 376 |
| SEQ_ID_NO_207 | VDFGI KQGLQ | WPALL QALAL | RPGGPPS FRL | TGVGPPPQPDE | 382 |
| SEQ_ID_NO_283 | VDFGI KQGLQ | WPALL QALAL | RPGGPPS FRL | TGVGPPPQHDE | 380 |
| SEQ_ID_NO_196 | DFGL KQGLQ | WPAL MQALAL | RPGGPPS FRL | TGI GPPPQPDE | 374 |
| SEQ_ID_NO_235 | DFGL KQGMQ | WPAL MQALAL | RPGGPPS FRL | TGI GPPPQPDN | 381 |
| SEQ_ID_NO_245 | DFGL KQGMQ | WPAL MQALAL | RPGGPPT FRL | TGI GPPPQPDN | 369 |
| SEQ_ID_NO_286 | DFGL KQGMQ | WPAL MQALAL | RPGGPPA FRL | TGI GPPPQPDN | 361 |
| SEQ_ID_NO_282 | DFGL RQGMQ | WPAL MQALAL | RPGGPPA FRL | TGI GPPPQPDN | 352 |
| SEQ_ID_NO_239 | DFGL KQGMQ | WPAL MQALAL | RPGGPPA FRL | TGI GPPPQPDN | 343 |
| SEQ_ID_NO_277 | DFSL KQGMQ | WPAL MQALAL | RPGGPPA FRL | TGI GPPPQPDN | 342 |

| SEQ_ID_NO_188 | TDAL QQVGWK | LAQF AHTI RV | DFQYRGL VAA | TLADL EPF ML | 426 |
|---|---|---|---|---|---|
| SEQ_ID_NO_221 | TDAL QQVGWK | LAQF AHTI RV | DFQYRGL VAA | TLADL EPF ML | 426 |
| SEQ_ID_NO_201 | TDAL QQVGWK | LAQF AHTI RV | DFQYRGL VAA | TLADL EPF ML | 425 |
| SEQ_ID_NO_194 | TDAL QQVGWK | LAQF AHTI RV | DFQYRGL VAA | TLADL EPF ML | 429 |
| SEQ_ID_NO_215 | TDAL QQVGWK | LAQF AHTI RV | DFQYRGL VAA | TLADL EPF ML | 431 |
| SEQ_ID_NO_202 | TDAL QQVGWK | LAQF AHTI RV | DFQYRGL VAA | TLADL EPF ML | 416 |
| SEQ_ID_NO_207 | TDAL QQVGWK | LAQF AHTI RV | DFQYRGL VAA | TLADL EPF ML | 422 |
| SEQ_ID_NO_283 | TDAL QQVGWK | LAQF AHTI RV | DFQYRGL VAA | TLADL EPF ML | 420 |
| SEQ_ID_NO_196 | TDAL QQVGWK | LAQLAETI GV | EFEFRGF VAN | SLADL EAEML | 414 |
| SEQ_ID_NO_235 | TDAL QQVGWK | LAQLAQTI GV | EFEFRGF VAS | SLADL EPSML | 421 |
| SEQ_ID_NO_245 | TDAL QQVGWK | LAQLAETI GV | EFEFRGF VAS | SLADL DP NML | 409 |
| SEQ_ID_NO_286 | TDAL QQVGWK | LAQLAQ N GV | EFEFRGF VCS | SLADL TPSML | 401 |
| SEQ_ID_NO_282 | TDAL QQVGWK | LAQLAD T GV | EFEFRGF VCN | SLADL DP KML | 392 |
| SEQ_ID_NO_239 | TDAL QQVGWK | QFEFRGF VAN | SLADL QPEML | 383 |
| SEQ_ID_NO_277 | TDAL QQVGWK | LAQLAETI GV | EFEFRGF VAN | SLADL DA T LL | 382 |

| SEQ ID | | | | | | | |
|---|---|---|---|---|---|---|---|
| SEQ_ID_NO_188 | 466 | QPEGEADANE | EPEVIAVNSV | FELHRLLAQP | GALEKVLGTV | |
| SEQ_ID_NO_221 | 466 | QPEGEADANE | EPEVIAVNSV | FELHRLLAQP | GALEKVLGTV | |
| SEQ_ID_NO_201 | 464 | QPDGEDTDDD | EPEVIAVNSV | EELHRLLAQP | GALEKVLGTV | |
| SEQ_ID_NO_194 | 468 | QPEGEDTDDD | EPEVIAVNSV | FELHRLLAQP | GALEKVLGTV | |
| SEQ_ID_NO_215 | 470 | QPEGEDLDKDE | EPEVIAVNSV | FELHRLLAQP | GALEKVLGTV | |
| SEQ_ID_NO_202 | 456 | QPEGEDLDKDE | EPEVIAVNSV | FEMHRLLAQP | GALEKVLGTV | |
| SEQ_ID_NO_207 | 461 | QPEGEEDPNE | EPEVIAVNSV | FEMHRLLAQP | GALEKVLGTV | |
| SEQ_ID_NO_283 | 460 | QPEGEEDPNE | EVEAVAVNSV | LELHRLLARP | GAIEKVLSSI | |
| SEQ_ID_NO_196 | 449 | QIRP-----P | -GEVAVNSV | FELHRLLDRP | GGIDKVLGSI | |
| SEQ_ID_NO_235 | 456 | DLRP------ | -GEVAVNSV | FELHRLLARP | GSVDKVMDTV | |
| SEQ_ID_NO_245 | 442 | EIRP-----S | -GEAVAVNSV | FELHRMLARP | GAVDKVLSSI | |
| SEQ_ID_NO_286 | 436 | DIRP------ | DVEIAVNSV | FELHRMLARP | GSVDKVLDTV | |
| SEQ_ID_NO_282 | 425 | DLRP-----P | ETEAVAINSV | FELHRLLARP | GGMEKVLSSI | |
| SEQ_ID_NO_239 | 418 | DIRP-----S | | FELHRLLSRP | GALEKVLNGI | |
| SEQ_ID_NO_277 | 417 | | | | | |

| SEQ ID | | | | | | | |
|---|---|---|---|---|---|---|---|
| SEQ_ID_NO_188 | 506 | HAVRPRIVTV | VEQEANHNSG | SFLDRFTESL | HYYSTMFDSL | |
| SEQ_ID_NO_221 | 506 | HAVRPRIVTV | VEQEANHNSV | SFLDRFTESL | HYYSTMFDSL | |
| SEQ_ID_NO_201 | 504 | RAVRPRIVTV | VEQEANHNSG | SFLDRFTESL | HYYSTMFDSL | |
| SEQ_ID_NO_194 | 508 | RAVRPRIVTV | VEQEANHNSG | SFLDRFTESL | HYYSTMFDSL | |
| SEQ_ID_NO_215 | 510 | RAVRPRIVTV | VEQEANHNSG | TFLDRFTESL | HYYSTMFDSL | |
| SEQ_ID_NO_202 | 496 | RAVRPRIVTV | VEQEANHNSG | TFLDRFTESL | HYYSTMFDSL | |
| SEQ_ID_NO_207 | 501 | RAVRPRIVTI | VEQEANHNGP | VFLDRFTEAL | HYYSNLFDSL | |
| SEQ_ID_NO_283 | 500 | KAMKPKIVTI | VEQEASHNGP | VFLDRFTEAL | HYYSSLFDSL | |
| SEQ_ID_NO_196 | 489 | KNLNPKIVTI | VEQEANHNGP | VFLDRFTEAL | HYYSNLFDSL | |
| SEQ_ID_NO_235 | 496 | KAMRPKIVTI | VEQEANHNGP | VFLDRFTEAL | HYYSSLFDSL | |
| SEQ_ID_NO_245 | 482 | KKIKPKIVTV | VEQEANHNGP | GFLDRFTEAL | HYYSSLFDSL | |
| SEQ_ID_NO_286 | 476 | KAMKPKIVTV | VEQEASHNGP | VFLDRFTEAL | HYYSSLFDSL | |
| SEQ_ID_NO_282 | 465 | KQLNPKIVTL | VEQEANHNAG | VFLDRFNEAL | HYYSTMFDSL | |
| SEQ_ID_NO_239 | 458 | | | | | |
| SEQ_ID_NO_277 | 457 | | | | | |

| SEQ_ID | Sequence | Length |
|---|---|---|
| SEQ_ID_NO_1 | MPTP-A------HLS--------------KDPHYFD FRAARRVPET | 25 |
| SEQ_ID_NO_2 | MPTP-S------HLS--------------KDPHYFD FRAARRVPET | 25 |
| SEQ_ID_NO_3 | MPTP-A------HLS--------------NDPRYFD FRAARRVPET | 25 |
| SEQ_ID_NO_4 | MPTP-S------HLS--------------KDPHYFD FRAARRVPET | 25 |
| SEQ_ID_NO_6 | MPTP-S----------------------KDPHYFD FRAARRVPET | 24 |
| SEQ_ID_NO_8 | MPTP-S----------------HL----KNPLYFD FRAARRVPES | 24 |
| SEQ_ID_NO_9 | MPTP-S------HLK--------------NPLCFD FRAARRVPET | 24 |
| SEQ_ID_NO_10 | MQSS--------SSAST-P---AA-ASGLVF LGSAAGVPET | 30 |
| SEQ_ID_NO_11 | MPSL--------MEQPIHFP--QPI-HHPKHFD LGSAHEVPDS | 33 |
| SEQ_ID_NO_12 | MPSR-L------SDAFKAHP--LHL-LNHRHLD LNSVQELPDS | 32 |
| SEQ_ID_NO_13 | MPAR-LSDAF--KSHPL-----NL--QLKHPD FSSLQELPDS | 32 |
| SEQ_ID_NO_14 | MPAP-R------MDPYKDKS--SHY-HRRHLD FQSVEELPDA | 34 |
| SEQ_ID_NO_15 | MHTN--------SM--------------INQKHLD LNSMKVLPES | 24 |
| SEQ_ID_NO_16 | MPSR-L------SDSFRAL---VH--HSQKHLD LNSIKELPES | 28 |
| SEQ_ID_NO_17 | MPTR-L------SDSFRPH-------VNHKHPD LNSIKELPES | 31 |
| SEQ_ID_NO_18 | MPSL-P------SRVVKL-E--QHPTKKSFLD LESLNELPDS | 29 |
| SEQ_ID_NO_19 | MPSL--------SEAYRAHP--VH--VNHKHPD FNSLQELPES | 31 |
| SEQ_ID_NO_20 | MPSL--------SEAYRAHP----------VNHKHPD FNSLQELPES | 31 |
| SEQ_ID_NO_21 | MPVR-L------SEAFPSHP--H-----KHYPAD ENSLHELPDS | 30 |

Figure 4A

| SEQ_ID | | | | | | | |
|---|---|---|---|---|---|---|---|
| SEQ_ID_NO_1 | HAWPGLHD | PVV | DGSGA | - | GEPDAVP | VVDMR | - | D | 56 |
| SEQ_ID_NO_2 | HAWPGLHD | PVV | DGGGA | G | GGPDAVP | VVDMR | - | D | 56 |
| SEQ_ID_NO_3 | HAWPGLHD | PVV | DGGEA | G | GGPDAVP | VVDMR | - | D | 56 |
| SEQ_ID_NO_4 | HAWPGLHE | PVV | DGR-A | G | AGEDAVL | VVDTR | - | D | 55 |
| SEQ_ID_NO_6 | HAWPGLHD | PVV | DGGLA | - | PGPDAVP | VVDLA | GAADE | 57 |
| SEQ_ID_NO_8 | HAWPGLHE | PVV | DGGGA | P | GTPDAVP | VVDLR | - | E | 55 |
| SEQ_ID_NO_9 | HAWPGLDD | PSV | DGG-G | - | GGEDAVP | VVDVR | - | A | 54 |
| SEQ_ID_NO_10 | HAWPGVNE | PP- | ES--- | - | AGRDMVP | VVDMG | - | V | 57 |
| SEQ_ID_NO_11 | HTWPTIQP | PSG | ----- | N | GPNESIP | VIDLS | - | S | 58 |
| SEQ_ID_NO_12 | YAWAGVDEL | PSS | DSL-- | - | LITESVP | VIDLT | - | D | 59 |
| SEQ_ID_NO_13 | YAWSQNDDQY | PLY | PGS-F | - | AEQDSVP | VIDLS | - | D | 63 |
| SEQ_ID_NO_14 | YEMGPLESH | PSE | -SS-- | G | GADQGVP | VIDLK | - | G | 60 |
| SEQ_ID_NO_15 | HAWLSLES | PLY | NSL-- | - | LSPDLVP | VIDLT | - | - | 51 |
| SEQ_ID_NO_16 | HAWTSSND | TLI | NSNNT | M | CNFESIP | VIDLD | - | N | 55 |
| SEQ_ID_NO_17 | YTWTHLDD | YTQ | ENS-- | KESA | NSSVP | VIDLS | - | N | 65 |
| SEQ_ID_NO_18 | HAWTSSND | CSI | DNPS- | - | CNFESIP | VINLQ | - | N | 57 |
| SEQ_ID_NO_19 | FAWGSFED | TLI | DSNN- | G | YGPDSVP | VIDLN | - | D | 61 |
| SEQ_ID_NO_20 | YNMTHLDD | PSL | DSSF- | K | ESTTTVP | VIDLN | - | D | 63 |
| SEQ_ID_NO_21 | YAWTNQLDEC | PSL | DSS-- | F | GSDLCVP | VIDLN | - | D | 60 |

| | | | | | | |
|---|---|---|---|---|---|---|
| SEQ_ID_NO_1 | EAAIAGMFAL | PASEKMRAVR | RPGD- | -SCGY | GSPPISSFFS | 126 |
| SEQ_ID_NO_2 | EAAIAGMFAL | PASEKMRAVR | RPGD- | -SCGY | GSPPISSFFS | 126 |
| SEQ_ID_NO_3 | EAAIAGMFAL | PASEKMRAVR | RPGD- | -SCGY | GSPPISSFFS | 126 |
| SEQ_ID_NO_4 | EARIAGMFAL | PAQEKMRAVR | RPGD- | -SCGY | GSPPISSFFA | 125 |
| SEQ_ID_NO_6 | EDRIATMFAL | PADDKMRAVR | GPGD- | -ACGY | GSPPISSFFS | 129 |
| SEQ_ID_NO_8 | EDRIARMFAL | PAADKMRAVR | GPGD- | -ACGY | GSPPISSFFS | 127 |
| SEQ_ID_NO_9 | EERVARVFSL | PASEKMRAVR | GPGE- | -PCGY | GSPSEFS | 124 |
| SEQ_ID_NO_10 | EEQVARLFVL | PAPDKARAGR | RPGEPT | ATGY | GRPPLALRFS | 131 |
| SEQ_ID_NO_11 | ESQARRLFSL | PTQQKLKAGR | SPNS- | -ISGY | GLAPISSLFS | 128 |
| SEQ_ID_NO_12 | ESAGRSLFSL | PAQQKLKAAR | SPDG- | -VAGY | GLARISSFFN | 129 |
| SEQ_ID_NO_13 | ESAGRSLFSL | PVQQKLKAAR | SPDG- | -ISGY | GFARISSFFQ | 133 |
| SEQ_ID_NO_14 | ESAGRRLFSL | PLHQKLKAAR | APDG- | -VTGY | GPARISSFFP | 130 |
| SEQ_ID_NO_15 | EAAGRRLFSL | PLQQKLKAAR | APDG- | -VSGY | GVARISSFFP | 121 |
| SEQ_ID_NO_16 | ELAGKSLFAL | PMQQKLKAAR | SPEG- | -VTGY | GLARISSFFP | 131 |
| SEQ_ID_NO_17 | QWLGQTLFTL | PSHQKLKAAR | SPDG- | -VTGY | GAAQISSLFS | 135 |
| SEQ_ID_NO_18 | DVAGKTLFSL | PMQQKLKAAR | SSCG- | -VSGY | GPAGISSFFP | 132 |
| SEQ_ID_NO_19 | EAAGKSLFAL | PVNQKLKATR | SPDG- | -VTGY | GIARISSLFS | 131 |
| SEQ_ID_NO_20 | QWLGQTLFSL | PSHQKHKATR | PADG- | -LSGY | GIHRISSFFP | 133 |
| SEQ_ID_NO_21 | ESTCRSLFSL | PVQQKLKAAR | | | | 130 |

Figure 4D

| | | | | | |
|---|---|---|---|---|---|
| SEQ_ID_NO_1 | KCMWSEGYTF | SPANLRSDLR | KLWPKAGHDY | RHFCAVMEEF | 166 |
| SEQ_ID_NO_2 | KCMWSEGYTF | SPANLRSDLR | KLWPKAGHDY | RHFCAVMEEF | 166 |
| SEQ_ID_NO_3 | KSMWSEGYTF | SPANLRSDLR | KLWPKAGHDY | RHFCAVMEEF | 166 |
| SEQ_ID_NO_4 | KCMWSEGYTF | SPANLRSDLR | KLWPKQGHDY | RLFCDVMEEF | 165 |
| SEQ_ID_NO_6 | KCMWSEGYTF | SPANLRSDLR | KLWPKAGDDY | TSFCDVMEEF | 169 |
| SEQ_ID_NO_8 | KCMWSEGYTF | SPANLRADLR | KLWPKAGDDY | ASFCDVMEEF | 167 |
| SEQ_ID_NO_9 | KLMWSEGYTF | SPASLRADLR | RLWPKSGDDY | LLFCDVMEEF | 164 |
| SEQ_ID_NO_10 | KLMWSEGYTF | SPSSLRSELR | RVWPDGGDDY | LRFCDVMEEY | 171 |
| SEQ_ID_NO_11 | KLMWSEGFTI | RAATVREEFR | SLWPD---DY | FNFCEVLEEY | 164 |
| SEQ_ID_NO_12 | KLMWYEGFTI | SGSPLDHAR | QLWPQ---DY | TKFCDVTEEF | 165 |
| SEQ_ID_NO_13 | KLMWSEGFTI | FGSPLEHAR | QLWPQ---DY | NKFCNIIEEY | 169 |
| SEQ_ID_NO_14 | KLLWSEGFTI | VGSPLDHFR | QLWPQ---SY | QNFCEIIEEY | 166 |
| SEQ_ID_NO_15 | KLMWSEGFTI | FGSPEDHAR | KLWPN---DY | TRFCDVIEEY | 157 |
| SEQ_ID_NO_16 | KLMWSEGFTI | MGSPYEHAR | QIWPH---DY | QKFCDYIEEY | 167 |
| SEQ_ID_NO_17 | KLMWSEGFTI | VGSPLEHAR | QLWPQ---DY | AKHCDIMLQY | 171 |
| SEQ_ID_NO_18 | KLMWSEGFTI | VGSPIDHFR | QLWPKL--NY | KKFCEVIEEY | 168 |
| SEQ_ID_NO_19 | KRMWSEGFTI | LGSPLDHAR | QLWPN---DY | NKFCDIIEKY | 167 |
| SEQ_ID_NO_20 | KLMWYEGFTI | VGSPLDHFR | ELWPQ---DY | TRFCDLVQY | 169 |
| SEQ_ID_NO_21 | KLMWSEGFTL | VGSPLEHFR | QLWPQ---DY | NKFCCMVEEY | 166 |

Figure 4E

| SEQ_ID_NO_1 | HREMRALADK | LLELFLVALG | LTGEQVA- | -E | SEQKI AET | 204 |
|---|---|---|---|---|---|---|
| SEQ_ID_NO_2 | HREMRVLADK | LLELFLVALG | LTGEQVA- | -E | SEHKI AET | 204 |
| SEQ_ID_NO_3 | HREMRALADK | LLELFLVALG | LTVEQVA- | -E | SEQQI AET | 204 |
| SEQ_ID_NO_4 | HGEMRALSDR | LLELFLAALG | LTGEQAA- | -E | AEHRI AET | 203 |
| SEQ_ID_NO_6 | HKHMRALADK | LLELFLMALG | LTDEQVG- | -E | AERRI AET | 207 |
| SEQ_ID_NO_8 | HKEMRVLAGK | LLELFLRALG | LTDEEVA- | -E | EERRI GET | 205 |
| SEQ_ID_NO_9 | HKEMRRLADE | LLRLFLRALG | LTGEEVA- | -E | AERRI GER | 202 |
| SEQ_ID_NO_10 | DREMRALGGR | LLDLFFMALG | LTDVQFA- | -E | TERRI RET | 209 |
| SEQ_ID_NO_11 | NKEMKRVAER | LMQLMLGSLG | LTEETI K- | -G | PMNELFQD | 201 |
| SEQ_ID_NO_12 | EKEMNQLAER | LMWLMLGSLG | LTKEDVN- | -WA | SKGD- -D | 199 |
| SEQ_ID_NO_13 | EKVMKRLAGR | LMWLMLGSLG | SMEDVK- | -WA | PKGDFRI D | 206 |
| SEQ_ID_NO_14 | DRDMKRLAGR | LMWLVLGSLG | VTMEDVE- | -WA | PTGDFNDI | 204 |
| SEQ_ID_NO_15 | KEEMNKLAQT | LMSL ML GSLG | TKEEVK- | -WA | SQGL- -- | 190 |
| SEQ_ID_NO_16 | EREMEKLAGR | LMWL ML DSLG | TMEDI E- | -G | VCPKGES- KG | 205 |
| SEQ_ID_NO_17 | DEAMKKLAGK | LMWL I LGSLG | TKDEVK- | -WA | SKAQFDEK | 209 |
| SEQ_ID_NO_18 | EKEMEKLAGR | LMQL VVGSLG | SNQDI | -G | PKGET- KE | 206 |
| SEQ_ID_NO_19 | QKEMNQLAKK | LMOL ML DSLG | ITKEDI K- | -WA | - LL EG | 202 |
| SEQ_ID_NO_20 | DETMKKLAGT | LMWL MDSLG | SKEDVS- | -MNWA | SKAQF EK | 206 |
| SEQ_ID_NO_21 | ETEMKKLAGR | LMWL I FGSLG | SKEDVS- | -G | PKGDFE- D | 203 |

Figure 4F

| SEQ_ID | | | | | Length |
|---|---|---|---|---|---|
| SEQ_ID_NO_1 | MTATMHLNWY | PKCPDPKRAL | GLIAHTDSGF | FTFVLQSLVP | 244 |
| SEQ_ID_NO_2 | MTATMHLNWY | PKCPDPKRAL | GLIAHTDSGF | FTFVLQSLVP | 244 |
| SEQ_ID_NO_3 | MTATMHLNWY | PKCPDPKRAL | GLIAHTDSGF | FTFVLQSLVP | 244 |
| SEQ_ID_NO_4 | MTATMHLNWY | PKCPDPKRAL | GLIAHTDSGF | FTFVLQSLVP | 243 |
| SEQ_ID_NO_6 | MTATMHLNWY | PKCPDPKRAL | GLIAHTDSGF | FTFVLQSLVP | 247 |
| SEQ_ID_NO_8 | MTATMHLNWY | PRCPDPKRAL | GLIAHTDSGF | FTFVLQSLVP | 245 |
| SEQ_ID_NO_9 | MTIMHLNWY | PRCPDPRRAL | GLIAHTNSGF | FTFVLQSLVP | 242 |
| SEQ_ID_NO_10 | MTATMHLNWY | PRCPEPRRAL | GLIAHTDSGF | ETFVLQSLVP | 249 |
| SEQ_ID_NO_11 | MTATVHLNWY | PRCPEPERAI | GLTAHTDSSL | LTILYQSNTS | 241 |
| SEQ_ID_NO_12 | VTATMHPILY | LSSVLQLNSY | PACPNPDRAM | GLAAHTDSSL | 239 |
| SEQ_ID_NO_13 | FKAALQLNSY | PACPEPDRAM | GLAAHTDSTL | FTILYQNTVS | 246 |
| SEQ_ID_NO_14 | ASAALQLNSY | PACPDPDRAM | GLAAHTDSTL | LTILYQNTTS | 244 |
| SEQ_ID_NO_15 | CSAALQLNSY | PKCPNPGRAM | GLAAHTDSTL | LTILYQNNTS | 230 |
| SEQ_ID_NO_16 | SCPALQLNSY | PACPDPDRAM | GLAPHTDSTI | LTILSQNNTS | 245 |
| SEQ_ID_NO_17 | GSAALQLNSY | PSCPDPDRAM | GLAAHTDSTF | LTILHQNNTS | 249 |
| SEQ_ID_NO_18 | ACAALQLNSY | PACPDPDHAM | GLAAHTDSTI | LTILSQNDIS | 246 |
| SEQ_ID_NO_19 | GCAALQLNSY | PLRPDPNRAM | GLAAHTDSTL | LTILHQNNTS | 242 |
| SEQ_ID_NO_20 | ANGAMQLNSY | PSCPDPDHAM | GLTPHTDSTF | LTILSQNDIS | 246 |
| SEQ_ID_NO_21 | ASNALQLNSY | PACPDPSRAM | GLAEHTDSTL | LTILHQSNLS | 243 |

Figure 4G

| | | | | | | |
|---|---|---|---|---|---|---|
| SEQ_ID_NO_1 | GLQLFRHG- | ---- | PDRWTV | PA- | VPGAMVV | NVGDLFQILT | 278 |
| SEQ_ID_NO_2 | GLQLFRHG- | ---- | PDRWTV | PA- | VPGAMVV | NVGDLFHILT | 278 |
| SEQ_ID_NO_3 | GLQLFRHG- | ---- | PDRWTV | PA- | VPGAMVV | NVGGLFQILT | 278 |
| SEQ_ID_NO_4 | GLQLFRHG- | ---- | PDRWTV | PA- | VPGAMVV | NVGDLFHILT | 278 |
| SEQ_ID_NO_6 | GLQLFRHA- | ---- | PDRWTV | PAD | VPGAFVV | NVGDLFQILT | 281 |
| SEQ_ID_NO_8 | GLQLFRHA- | ---- | PDRWAV | PA- | VPGAFVV | NVGDLFHILT | 279 |
| SEQ_ID_NO_9 | GLQLFRRG- | ---- | PDRWAV | PA- | VAGAFVV | NVGDLFQILT | 276 |
| SEQ_ID_NO_10 | GLQLLRRG- | ---- | PDRWTV | PA- | PPGALIV | MLGDLFQVLT | 283 |
| SEQ_ID_NO_11 | GLQVLRPNKE | SSPT | QWWTV | PPI | PPGALVV | NVGDLCHILS | 279 |
| SEQ_ID_NO_12 | GLQVQREG- | ---- | A-GMTV | PPI | LPGALVI | NVGDLLHILS | 272 |
| SEQ_ID_NO_13 | GLQVLREG- | ---- | TI-GWWTV | PPI | LPGALVV | NIGDLFHILS | 279 |
| SEQ_ID_NO_14 | GLQVHRDG- | ---- | L-GWMV | PPI | VPGALVV | NVGDLLHILS | 277 |
| SEQ_ID_NO_15 | GLQVFKEG- | ---- | AI-GWWTV | PPI | FPGALVI | NIGDLLHILS | 263 |
| SEQ_ID_NO_16 | GLQAHRDG- | ---- | SI-GWWTV | PPI | LHGGLVV | NVGDLLHILS | 278 |
| SEQ_ID_NO_17 | GLQVFQEG- | ---- | N-NGWWTV | PPI | IPGALVV | NVGDLLHILS | 282 |
| SEQ_ID_NO_18 | GLQVYQEG- | ---- | SI-GWWTV | PPI | SGGLVI | NVGDLFHILS | 279 |
| SEQ_ID_NO_19 | GLQVFER-- | ---- | SI-GWTV | PPI | LQGGLVV | NVGDLLHILS | 275 |
| SEQ_ID_NO_20 | GLQVNREG- | ---- | A-GMTV | PPI | VAGALVI | NVGDLFHILS | 279 |
| SEQ_ID_NO_21 | GLQVLREG- | ---- | A-GWLTV | PPI | VAGALVI | NIGDLIHILS | 276 |

Figure 4H

| | | | | | |
|---|---|---|---|---|---|
| SEQ_ID_NO_1 | NGRFHSVYHR | AVVNRESDRI | SLGYFLGPPA | HVKVAPLREA | 318 |
| SEQ_ID_NO_2 | NGRFHSVYHR | AVVNRDSDRI | SLGYFLGPPA | HVKVAPLREA | 318 |
| SEQ_ID_NO_3 | NGRFHSVYHR | AVVNRDSDRI | SLGYFLGPPA | DIKVAPLREA | 318 |
| SEQ_ID_NO_4 | NGRFHSVYHR | AVVNRDSDRI | SLGYFLGPPA | HVKVAPLREA | 318 |
| SEQ_ID_NO_6 | NGRFHSVYHR | AVVNRDLDRI | SLGYFLGPPA | HAKVAPLREA | 318 |
| SEQ_ID_NO_8 | NGRFHSVYHR | AVVNRDLDRI | SLGYFHGPPA | HAKVAPLREA | 321 |
| SEQ_ID_NO_9 | NGRFHSVYHR | AVVNRDRDRV | SLGYFLGPPP | DAEVAPLPEA | 319 |
| SEQ_ID_NO_10 | NGRFRSPIHR | AVVSRERERL | SVPYFLCPPE | DMTVAPLASA | 316 |
| SEQ_ID_NO_11 | NGRFHSVYHR | AVVNRTEHRY | SAAYLCGPPA | HVKVSPIVKP | 323 |
| SEQ_ID_NO_12 | NGKFPSVHR | ALVNRTKHRL | SVAYLYGPPA | GVPISPVPKL | 319 |
| SEQ_ID_NO_13 | NGLYPSVLHR | AVVNRSRHRL | SIAYLYGPPA | SVQISPLSKL | 312 |
| SEQ_ID_NO_14 | NGLYPSVLHR | AVVNRTHHRL | SVAYLFGPPQ | SVRISPLERL | 319 |
| SEQ_ID_NO_15 | NGLYPSVLHR | AVVNRTRHRL | SVAYLYGPPS | NVQISPLSKL | 317 |
| SEQ_ID_NO_16 | NGSYPSVLHR | AMVNRTKHRL | SVAYLYGPPS | RVKVSPLAKL | 303 |
| SEQ_ID_NO_17 | NGLYTSVLHR | AVVNRTRHRL | SVAYLYGPPT | NVEICPHEKL | 318 |
| SEQ_ID_NO_18 | NGSYPSVLHR | AMVNRVQHRL | SVAYLYGPAS | GVRVSPLSKL | 322 |
| SEQ_ID_NO_19 | NGRYPSVYHR | VLVNRTRQRF | SVAYLYGPPT | GVRVQLPLPKL | 315 |
| SEQ_ID_NO_20 | NGLYPSVLHR | AVVNRTRQRF | SVAYLYGPPS | NVEICPHAKL | 319 |
| SEQ_ID_NO_21 | NGEYQNVFHR | ALVNRSQQRL | SVAYLYGPPL | NVQISPHSKL | 316 |

Figure 4I

| SEQ_ID | | | | | | | Pos |
|---|---|---|---|---|---|---|---|
| SEQ_ID_NO_1 | LA- | GTPAAY | RAVTWPEYMG | VRKKAFTTGA | SALKMVAIST | 356 |
| SEQ_ID_NO_2 | LA- | GTPAAY | RAVTWPEYMG | VRKKAFTTGA | SALKMVAIST | 356 |
| SEQ_ID_NO_3 | LA- | GTPAAY | RAVTWPEYMG | VRKKAFTTGA | SALKMVAIPT | 356 |
| SEQ_ID_NO_4 | VGRT | GGKPAY | RAVTWPEYMG | VRKKAFTTGA | SALKMVAIIT | 358 |
| SEQ_ID_NO_6 | VPP- | GRTPAY | RAVTWPEYMG | VRKKAFTTGA | SALKMVALAA | 358 |
| SEQ_ID_NO_8 | VPP- | GRTPAY | RAVTWPEYMG | VRKKAFTTGA | SALKMVAAAA | 360 |
| SEQ_ID_NO_9 | VPA- | GRSPAY | RAVTWPEYMA | VRKKAFATGG | SALKMVSTDA | 358 |
| SEQ_ID_NO_10 | LLP- | GRKAVF | RAVTWPEYME | VKHKVFGTDA | PALEMLQLQV | 355 |
| SEQ_ID_NO_11 | VG-- | -PAY | RPITWREYLG | LKARLFDKAL | ASVLSEE--- | 362 |
| SEQ_ID_NO_12 | VDS- | THPPLY | RPVTWSEYLC | TKAKHFDKAL | SLVRLCMPRN | 352 |
| SEQ_ID_NO_13 | LGP- | SQPPLY | RPITWNEYLG | TKAKHFNKAL | SSVRLCAPLN | 351 |
| SEQ_ID_NO_14 | VDP- | DHPALY | RPISWTEYLS | TKAKHFNKAL | SSVRLCGPPV | 358 |
| SEQ_ID_NO_15 | VDP- | VHPPLY | RPVTWSEYLG | TKAKHFNKAL | SSVRVCAPLN | 356 |
| SEQ_ID_NO_16 | TDQ- | TQPPLY | RAVTWSEYLG | TKAKRHFDKAL | SSVRLCAPLS | 342 |
| SEQ_ID_NO_17 | VGP- | RHPPLY | RSVTWNEYLG | TKAKYEDKAL | SSVSLCVPLS | 357 |
| SEQ_ID_NO_18 | LDH- | THPPLY | RAVTWSEYLG | IKSEHLTKAL | SSVRLCAPIN | 361 |
| SEQ_ID_NO_19 | DA- | TKPPLY | RPVTWSEYLG | TKAKHFNKAL | SLIRINHNTN | 358 |
| SEQ_ID_NO_20 | GP- | SHPSLY | RSVTWNEYLG | LEGKLYNKAL | SSVRLCTPIN | 354 |
| SEQ_ID_NO_21 | VTP- | -- | RPVTWKEYLG | LEGKLYNKAL | SSIKFHDHQ- | 354 |

Figure 4J

| | | |
|---|---|---|
| SEQ_ID_NO_1 | - - - - - - LS | 369 |
| SEQ_ID_NO_2 | - - - - - - LSS | 369 |
| SEQ_ID_NO_3 | - - - - - - ISS | 368 |
| SEQ_ID_NO_4 | - - - - - - ISS | 372 |
| SEQ_ID_NO_6 | - - - - - - VSS | 389 |
| SEQ_ID_NO_8 | - - - - - - LSS | 374 |
| SEQ_ID_NO_9 | AAAAD VHA | 373 |
| SEQ_ID_NO_10 | - - - - - - ATT | 374 |
| SEQ_ID_NO_11 | - - - - - - SCV | 365 |
| SEQ_ID_NO_12 | - - - - - - KVG | 365 |
| SEQ_ID_NO_13 | - - - - - - KVG | 372 |
| SEQ_ID_NO_14 | - - - - - EVGS | 368 |
| SEQ_ID_NO_15 | - - - - - - QVG | 356 |
| SEQ_ID_NO_16 | - - - - - - QVG | 371 |
| SEQ_ID_NO_17 | - - - - - - QVG | 377 |
| SEQ_ID_NO_18 | - - - - - - QVG | 372 |
| SEQ_ID_NO_19 | - - - - - - VFG | 382 |
| SEQ_ID_NO_20 | - - - - - - QVG | 374 |
| SEQ_ID_NO_21 | - - - - - - DQM | 358 |

| SEQ ID | Sequence | Length |
|---|---|---|
| SEQ_ID_NO_287 | DMSDPESKHA LVKACEDFGF FKVINHGVSA ELVSMEHETI | 61 |
| SEQ_ID_NO_288 | DLSEPDSKHL VVKSCEEFGF FKVINHGIPL ELISRLETEV | 70 |
| SEQ_ID_NO_290 | DLSKPDSKHL LVKACEEFGF FKVVNHGVPL EFISKLESEA | 70 |
| SEQ_ID_NO_291 | DLSKPDSRQQ ILKACEEFGF FKVINHGVPL DFISRLESEA | 71 |
| SEQ_ID_NO_292 | DLSAPDAKQL IVEACEEFGF FKVVKHGVPM ELISSLESES | 58 |
| SEQ_ID_NO_293 | DLKDPEAKTR IVKACEELGF FKLVNHGVPF EFMTRLEYLA | 71 |
| SEQ_ID_NO_294 | DLSAPDAKHL IVEACQEFGF FKVINHGVPM EFISTLESEA | 63 |
| SEQ_ID_NO_295 | DLTKPDSKQL IVKACEEFGF FKVINHGVPT EFITRLESEA | 71 |
| SEQ_ID_NO_296 | DLSKPESKQH LVKACEEFGF FKFINHGVPM DFISTLESEA | 72 |
| SEQ_ID_NO_297 | DLSKPDSKNL IVKACQEFGF FKVINHSVPT EFITKLESEA | 68 |
| SEQ_ID_NO_298 | DLTDPEAKNL IVEACEEFGF FKVINHDVPI DFMTRLESEA | 70 |
| SEQ_ID_NO_299 | DLSKPESKQH LVKACEEFGF FKLVNHGVPI KFINKLESEA | 71 |
| SEQ_ID_NO_300 | DLSKPDAKTH IVEACEEFGF FKVVNHGVPL EFISKLESEA | 69 |
| SEQ_ID_NO_301 | DLTDPDAKTL KACEEFGF FKLVNHGVPL QFMANLENET | 72 |
| SEQ_ID_NO_303 | DLTDPHAKTL LVRACERDGF FKLVNHGIPM EVMTKLEALA | 70 |
| SEQ_ID_NO_305 | NLAQPGSETL LVEACEELGF FKVVNHGVPA ELIARLEEEA | 70 |
| SEQ_ID_NO_306 | DLSRPGAPRA ADACERFGF FKVVNHGVAT DTMDKAESEA | 71 |
| SEQ_ID_NO_308 | DLSSPGAARA ADACERYGF FKLVNHGVAL DAMDRLESEA | 70 |
| SEQ_ID_NO_309 | DLGSPGAARA VVRACEQFGF FKVVNHGVPT DTMDKAESEA | 71 |
| SEQ_ID_NO_310 | DLSGPDAAGD VVDACERFGF FSVVNHGVAT GVVDRLEAEA | 71 |
| SEQ_ID_NO_311 | DLSSPGAALA VVDACERFGF FKVVNHGVPT GVVDRLEAEA | 74 |
| SEQ_ID_NO_313 | DLSSPGAALA VVDACERFGF FKVVNHGVPT GVVDRLEAEA | 74 |
| SEQ_ID_NO_314 | DLSNPDAKTQ IVNACQEFGF FKVINHGVPM EITKLEAQA | 69 |

Figure 5B

| | | | | | |
|---|---|---|---|---|---|
| SEQ_ID_NO_287 | VDFFSLPKSE | KTQVAL-- | -GY | PFGYGNSKI G | RNGDVGWEY | 98 |
| SEQ_ID_NO_288 | LEFFSLSLSE | KQKAGPL- | -PD | PFGYGNRSI G | PNGDVGWEY | 108 |
| SEQ_ID_NO_290 | VKFFSLPLSE | KEKASPL- | -PN | PFGYGNKKS I G | QNGDVGWEY | 108 |
| SEQ_ID_NO_291 | TKFFSLPLSE | KEKITGQ- | -PK | PYGYGNKQI G | PNGDVGWEY | 109 |
| SEQ_ID_NO_292 | TKFFSLPLSE | KQRAGPL- | -PS | PFGYGNKQI G | RNGDVGWEY | 109 |
| SEQ_ID_NO_293 | MNFFNLPQSE | KDKAGPL- | -PS | PFGYGNKQI G | PNGDVGW EY | 96 |
| SEQ_ID_NO_294 | TKFFSLPLSE | KQKAGPL- | -PD | PLGYGNKQI G | PNGDVGWEY | 109 |
| SEQ_ID_NO_295 | KFFSLPLST | KEKAGPL- | -PN | PFGYGNKHI G | PNGDVGWEY | 101 |
| SEQ_ID_NO_296 | LKFFSSPLSE | KLKAGPL- | -PD | PFGYGNKRI G | KNGDVGWEY | 109 |
| SEQ_ID_NO_297 | LRFFSSPLSE | KDKAGPL- | -AD | PFGYGNKNVG | RNGDVGWEY | 110 |
| SEQ_ID_NO_298 | LKFFSSPLSE | KQKAGPL- | -PD | PFGYGNKRI G | ACGDI GWEY | 106 |
| SEQ_ID_NO_299 | INFFNLPQSE | KEKFGPL- | -AY | PFGYGNKQI G | PNGDI GWEY | 108 |
| SEQ_ID_NO_300 | KFFSLPQSE | KLKAGPL- | -GN | PFGYGNKKI G | PNGDI GWEY | 109 |
| SEQ_ID_NO_301 | LGFFKKPQSE | KERAGIT- | -GN | PFGYGNKRI G | PNGDVGWEY | 107 |
| SEQ_ID_NO_303 | TNFFNLPOPE | KDRAGPL- | -AY | PFGYGSKRI G | QSGDI GWEY | 110 |
| SEQ_ID_NO_305 | VKFFSLAQVE | KDRSGPL- | -AY | PFGYGSKRI G | PNGDVGWEY | 108 |
| SEQ_ID_NO_306 | VRFFSLPQAD | KDRSGPL- | -AN | PFGYGNKRI G | HTGDMGWLEY | 108 |
| SEQ_ID_NO_308 | VRFFSQTQPD | KDASAPAGAD | -- | PFGYGSKRI G | LNGDMGWLEY | 109 |
| SEQ_ID_NO_309 | VRFFGSSPAV | KDACGPL- | -AN | PLGYGSKRI G | LNGDMGWLEY | 109 |
| SEQ_ID_NO_310 | VRFFASPQAD | KNKA---- | ---A | PFGYGNKNI G | FNGDMGWLEY | 109 |
| SEQ_ID_NO_311 | | | | | RNGDMGWLEY | 111 |
| SEQ_ID_NO_313 | | | | | | 112 |
| SEQ_ID_NO_314 | LSFFKQPQNH | | | | BKGDTGWLEY | 104 |

| SEQ_ID_NO | | | | | | | |
|---|---|---|---|---|---|---|---|
| SEQ_ID_NO_287 | PCPL | SNKK | -TN- | GGKNVI | GFGEHTDPQI | ISVLRSNNTS | 212 |
| SEQ_ID_NO_288 | PCSE | LQAS- | -N-- | GKNMI | GFGEHTDPQI | ISVLRSNNTS | 220 |
| SEQ_ID_NO_290 | PCPE | LQAL- | -K-- | DHNMI | GFGEHTDPQI | ISVLRSNNTS | 220 |
| SEQ_ID_NO_291 | PCPE | VQSL- | -NG- | TSSNVI | GFGEHTDPQI | ISVLRSNNTT | 219 |
| SEQ_ID_NO_292 | PCPD | LQAL- | -K-- | GTNMI | GFGEHTDPQI | ISVLRSNNTS | 208 |
| SEQ_ID_NO_293 | PCPE | LQAL- | -S-- | GRNLI | GFGEHTDPQI | ISVLRSNNTS | 221 |
| SEQ_ID_NO_294 | PCPE | EQAL- | -E-- | GTNMI | GFGEHTDPQI | ISVLRSNNTT | 210 |
| SEQ_ID_NO_295 | PCPE | LQGL- | -SSA | GARNVI | GFGEHTDPQI | ISVLRSNNTS | 224 |
| SEQ_ID_NO_296 | PCPE | FQENE | -RN- | GRKLV | GFGEHTDPQI | ISVLRSNNTS | 224 |
| SEQ_ID_NO_297 | PCPE | LQEF- | -S-- | GKNLI | GFGEHTDPQI | ISVLRSNNAS | 215 |
| SEQ_ID_NO_298 | PCPE | LQLQ- | -PL- | DNNLI | GFGEHTDPQI | ISVLRSNNTS | 220 |
| SEQ_ID_NO_299 | PCPE | FQEKE | -RN- | SGRNLV | GFGEHTDPQI | ISVLRSNNTT | 223 |
| SEQ_ID_NO_300 | PCPE | QEF- | -N-- | GSKLV | GFGEHTDPQI | ISVLRSNNTS | 211 |
| SEQ_ID_NO_301 | PCPE | VQAL- | -N-- | AKNLI | GFGEHTDPQI | ISVLRSNNTS | 222 |
| SEQ_ID_NO_303 | PCSE | LQAL- | -S-- | GRNLV | GFGEHTDPQI | ISVLRSNNTS | 220 |
| SEQ_ID_NO_305 | PCPH | LPEL- | ---- | GGNLI | GFGEHTDPQL | ISVLRSNGTS | 219 |
| SEQ_ID_NO_306 | PCHA | LQGL- | ---- | DSSLT | GFGEHTDPQL | SILRSNNTS | 220 |
| SEQ_ID_NO_308 | PCHA | LQGL- | ---- | GCSAT | GFGEHTDPQL | ISVLRSNGTS | 217 |
| SEQ_ID_NO_309 | PCRA | LQGL- | -P-- | GCSVT | GFGEHTDPQL | VSVLRSNGTA | 217 |
| SEQ_ID_NO_310 | PCPL | LQRL- | -P-- | PSCSVT | GFGEHTDPQL | VSILHSNGTA | 217 |
| SEQ_ID_NO_311 | ACPL | LQGL- | ---- | DSCGVT | GFGEHTDPQL | VSVLRSNGTA | 222 |
| SEQ_ID_NO_313 | AS-- | ----- | ---- | DRNEL | GFGEHTDPQL | | 222 |
| SEQ_ID_NO_314 | | | | | GFGEHTDPQI | ISVLRSNNAS | 206 |

Figure 5F

| SEQ_ID_NO | | | | | |
|---|---|---|---|---|---|
| SEQ_ID_NO_287 | GLQINLND- | GSWMSVPPDH | TSFFENVGDS | LQVMTNGRFK | 250 |
| SEQ_ID_NO_288 | GLQISLGN- | GSWMSVPPDA | NSFFINVGDS | LQVMTNGRFK | 258 |
| SEQ_ID_NO_290 | GLQISLND- | GSWMSVPPDP | SSFFINVGDS | LQVMTNGRFK | 258 |
| SEQ_ID_NO_291 | GLQISLRD- | GTWMSVPPDQ | YSFFINVGDS | LQVMTNGRFK | 257 |
| SEQ_ID_NO_292 | GFQISLAD- | GNWMSVPPDQ | SSFFINIGDA | LQVMTNGRFK | 246 |
| SEQ_ID_NO_293 | GLQICLRD- | GTWMSVPPDQ | TSFFINVGDS | LQVMTNGRFR | 259 |
| SEQ_ID_NO_294 | GLQISLPD- | ANWMSVPPDQ | NSFFINVGDS | LQVLTNGRFK | 248 |
| SEQ_ID_NO_295 | GLQISLRD- | GSWMSVPPDQ | DSFFINVGDS | LQVMTNGRFE | 262 |
| SEQ_ID_NO_296 | GLEISLRD- | GSWVMSVPPDP | HSFFINVGDS | LQVMANGRFK | 262 |
| SEQ_ID_NO_297 | GLQIALLKN- | GSWVMSVPPDS | NSFFINVGDS | LQVMTNGRFK | 253 |
| SEQ_ID_NO_298 | GLEISLRD- | GHWSVPPDQ | ESFFINVGDS | LQVMTNGRFK | 258 |
| SEQ_ID_NO_299 | GLQILLKN- | GNWESVPPDQ | SSFFVNVGDS | LQVMTNGRFR | 261 |
| SEQ_ID_NO_300 | GLQICLTD- | GTWWSVPPDQ | TSFFINVGDT | LQVLTNGRFK | 249 |
| SEQ_ID_NO_301 | GLQICLKE- | GSWWSVPPDQ | DSFFINVGDA | LQVMTNGRFK | 260 |
| SEQ_ID_NO_303 | GLQIYLRD- | GQWWSVPPDR | DAFFVNVGDS | LQVLTNGRFR | 260 |
| SEQ_ID_NO_305 | GLQIALQN- | GHWWSVPSDR | DSFFVNVGDS | LQVLTNGRFK | 258 |
| SEQ_ID_NO_306 | GLQIALQS- | GQWWSVPPNR | DAFFVNVGDS | LQVLTNGRFK | 257 |
| SEQ_ID_NO_308 | GLQIALRD- | GRWWSVPPDR | DSFFVNVGDS | LQVMRNGRFK | 258 |
| SEQ_ID_NO_309 | GLQVALHD- | GRWWPVPPDR | DAFFVTVGDS | LQVLTNGRLK | 255 |
| SEQ_ID_NO_310 | GLQVALHDDG | GTWTQVPADP | SSFITVDDC | LQVMTNGRFR | 255 |
| SEQ_ID_NO_311 | GLEIALKD- | | | | 260 |
| SEQ_ID_NO_313 | | | | | 262 |
| SEQ_ID_NO_314 | | | | | 244 |

Figure 5G

| SEQ ID | Sequence | Pos |
|---|---|---|
| SEQ_ID_NO_287 | SVRHRVLANC - KKSRVSMIY FAGPSLTQRI APLTCLIDNE | 289 |
| SEQ_ID_NO_288 | SVRHRVLANS - IKSRISMIY FGGPPLNEKI APLPSLVELG | 296 |
| SEQ_ID_NO_290 | SVRHRVLANS - IKARISMIY FGGPPLREKI APLPSLMELG | 296 |
| SEQ_ID_NO_291 | SVKHRVLANS - VKSRLSMIY FCGPPLSEKI APLPSLMRGD | 296 |
| SEQ_ID_NO_292 | SVKHRVLTNS - SKSRVSMIY FGGPPLSEKI APLASLMQGE | 285 |
| SEQ_ID_NO_293 | SVKHRVLADD - MKSRISMIY FGGPPLSEKI APFPSLLAEG | 298 |
| SEQ_ID_NO_294 | SVRHRVLTNS - LKSRISMIY FGGPPLSEKI APLPSLMKG. | 286 |
| SEQ_ID_NO_295 | SVKHRVLANG - LKSRVSMIY FGGPPLSEKI APLQSVMNGE | 301 |
| SEQ_ID_NO_296 | SVKHRVLANS - TKSRLSMIY FGGPPLSEKI APLPSLIQGE | 301 |
| SEQ_ID_NO_297 | SVKHRVLANS - AKSRLSMIY FGGPPLSEKI APLPSLMEAE | 292 |
| SEQ_ID_NO_298 | SVRHRVLSNS - VKSRLSMIY FGGPPLSEKI APLASLMEL G | 296 |
| SEQ_ID_NO_299 | SVKHRVLANS - MRSRVSMIY FGGPPLSEKI APLPSVLREG | 300 |
| SEQ_ID_NO_300 | SVKHRVLADT - TKSRVSMIY FGGPPLSEKI APLPSLMQGE | 288 |
| SEQ_ID_NO_301 | SVKHRVANG - VKSRLSMIY FGGPPLSEKI APLPSLMEGE | 299 |
| SEQ_ID_NO_303 | SVKHRVLADP - TKSRLSMIF FGGPPLSEKI APLPSLMLKG | 297 |
| SEQ_ID_NO_305 | SVKHRVLADP - LKPRISMIY FGGPPLCEKI APLPSLMAER | 296 |
| SEQ_ID_NO_306 | SVKHRVLAHG - LKSRVSMIY FGGPPSGERL APLLMGEG | 297 |
| SEQ_ID_NO_308 | SVKHRVVANS - LKSRVSMIY FGGPAMTQRI APLPQLLGAG | 294 |
| SEQ_ID_NO_309 | SVKHRVVANS - LKSRVSMIE FGGPALTQRI APLPQLLREG | 294 |
| SEQ_ID_NO_310 | SVRHRVVAGS - LKSRVSMIY FGGPPLAQRI APLPQLLGEG | 294 |
| SEQ_ID_NO_311 | SVRHRVVANS - GLKSRVSMIY FGGPPLAPAQRI APLPQLLAG. | 299 |
| SEQ_ID_NO_313 | SVRHRVITES - LKPRVSMIY FAGPPLAQRI APLPQVLGHG | 301 |
| SEQ_ID_NO_314 | SVKHRVITES - LKERLSMIY FGGPPLSEKI APSTSLMQG. | 282 |

Figure 5H

| SEQ ID | Sequence | Pos |
|---|---|---|
| SEQ_ID_NO_287 | DERLYEEFTW SEYKNSIYNS RLSDNRLQQF ERK----TL | 324 |
| SEQ_ID_NO_288 | KESLYKEFTW FEYKRSAYKS RLGDNRLSQF ERT----A- | 330 |
| SEQ_ID_NO_290 | EESLYREFTW FEYKRSAYNS RLADNKLVLF ERI----TL | 330 |
| SEQ_ID_NO_291 | QQSLYKEFTW FEYKKSAYNS RLADNRLMHF EKI----V- | 330 |
| SEQ_ID_NO_292 | ERSLYKEFTW YEYKRSAYNS RLADNRLVPF ERI----A- | 319 |
| SEQ_ID_NO_293 | EEGLYEQFTW FEYKKSAYNS RLADYRLGLF EKKMQAILA- | 337 |
| SEQ_ID_NO_294 | EESLYKEFTW FEYKKSAYSS RLADNRLVHF ERI----A- | 320 |
| SEQ_ID_NO_295 | EESMYKEFTW FEYKKSAYKS RLADNRLGHF EKI----A- | 335 |
| SEQ_ID_NO_296 | EDSLYKEFTW FEFKKSAFNT RLADNRLGLF EKI----T- | 335 |
| SEQ_ID_NO_297 | QDSLYKEFTW FEYKKSAFSS RLAVNRLVPF EKI----A- | 326 |
| SEQ_ID_NO_298 | EESLYKEFTW CEYKKSAYKT RLADNRLVLF EKV----A- | 330 |
| SEQ_ID_NO_299 | EESLYKEFTW FEYKKSAFNS RL-------- ---------- | 321 |
| SEQ_ID_NO_300 | EDSLYKEFTW FEYKKSAFKS RLSDNRLGLF EKL----L- | 322 |
| SEQ_ID_NO_301 | ESSLYKEFTW MEYKKAAYAS RLAQNRLTLF EKF----G- | 333 |
| SEQ_ID_NO_303 | EESFYKEFTW FEYKRSAYKS RLADNRLGPF EKS----A- | 331 |
| SEQ_ID_NO_305 | GGSLYREFTW CEYKSEAHGT RLADYRLGLF EKT----A- | 330 |
| SEQ_ID_NO_306 | EESLYKEFTW GEYKKAAYNS RLTDNRLGQF QR------- | 329 |
| SEQ_ID_NO_308 | EQSLYKDFTW DEYKKAAYNS RLGDNRLAQF HR------- | 326 |
| SEQ_ID_NO_309 | EQSLYKDFTW GEYKKAAYKS RLGDNRLAHF HR------- | 326 |
| SEQ_ID_NO_310 | -LPLYREFTW GEYKKAAYRS RLGDNRLAQF EK------- | 326 |
| SEQ_ID_NO_311 | EQSLYRDFTW GDYKKAAYRS RLGDNRLAPF EEP----PV | 333 |
| SEQ_ID_NO_313 | EESLYKEFTW GEYKKAAENT KLAFNRISFE RL------- | 333 |
| SEQ_ID_NO_314 | ---------- ---------- ---------- EKS------ | 315 |

| SEQ ID NO | Sequence | Position |
|---|---|---|
| SEQ_ID_NO_287 | K-----NL---------------- | 329 |
| SEQ_ID_NO_288 | ------AT---------------- | 332 |
| SEQ_ID_NO_290 | ------AS---------------- | 332 |
| SEQ_ID_NO_291 | ------AS---------------- | 332 |
| SEQ_ID_NO_292 | ------AS---------------- | 321 |
| SEQ_ID_NO_293 | ------NI---------------- | 339 |
| SEQ_ID_NO_294 | --------AS-------------- | 322 |
| SEQ_ID_NO_295 | --------AS-------------- | 337 |
| SEQ_ID_NO_296 | --------AT-------------- | 337 |
| SEQ_ID_NO_297 | --------AS-------------- | 328 |
| SEQ_ID_NO_298 | --------AS-------------- | 332 |
| SEQ_ID_NO_299 | ------------AS---------- | 321 |
| SEQ_ID_NO_300 | ------------TS---------- | 324 |
| SEQ_ID_NO_301 | ------------AD---------- | 335 |
| SEQ_ID_NO_303 | ------------GQ---------- | 333 |
| SEQ_ID_NO_305 | ------------------------ | 332 |
| SEQ_ID_NO_306 | ------------------------ | 329 |
| SEQ_ID_NO_308 | ------------------------ | 326 |
| SEQ_ID_NO_309 | ------------------K----- | 326 |
| SEQ_ID_NO_310 | AAGH--------------H-VS-- | 327 |
| SEQ_ID_NO_311 | --------------------Q--- | 341 |
| SEQ_ID_NO_313 | ----------------------PS | 334 |
| SEQ_ID_NO_314 | ------------------------ | 317 |

| | | | | | | |
|---|---|---|---|---|---|---|
| SEQ_ID_NO_1429 | MSI E | N | M | | TSYAG | 12 |
| SEQ_ID_NO_1430 | M- | | | | TSYAG- | 7 |
| SEQ_ID_NO_1431 | MPQA- | | PA- | | -K | 9 |
| SEQ_ID_NO_1432 | MKHI- | D | -H- | | | 12 |
| SEQ_ID_NO_1433 | MSPS- | F | VMNF- IS- | | | 15 |
| SEQ_ID_NO_1434 | MLVK- | | L- FSLC | NMWDQ | | 13 |
| SEQ_ID_NO_1435 | MANP- | S | AT- PSSI | PSWMERLD | ELLEAPWAF | 19 |
| SEQ_ID_NO_1436 | MDHF- | N | LAGPESNTSI | TSL-EWLGIK | NSFTGSHWAH | 34 |
| SEQ_ID_NO_1437 | MARNL TVMAA | | QI- TGSL | PSWAQLPQLK | | 35 |
| SEQ_ID_NO_1438 | MANP- | S | AT- PSSI | PSWMERLD | -KVIAMPFTN | 19 |
| SEQ_ID_NO_1439 | MAVQ- | Q | LI- | TLEFFG- | | 12 |

| | | | | | | |
|---|---|---|---|---|---|---|
| SEQ_ID_NO_1429 | | S | QLL- PFYIA | FVFTLVPWA | -RF SWLEL | 39 |
| SEQ_ID_NO_1430 | | S | QPL- SFYVA | FIFTLVPWA | -RF SWPKL | 34 |
| SEQ_ID_NO_1431 | -MMP | | LPGVGVYVFT | VLW- -AAT | YI- ASSLL | 36 |
| SEQ_ID_NO_1432 | CS- WSKDSP | LY | -GF- VLL-S | LVI- LGS | VTFI PKCGR | 44 |
| SEQ_ID_NO_1433 | NS- TASASN | | PP- N-VTA | AALALLAVAA | LYL- SFPSQ | 42 |
| SEQ_ID_NO_1434 | KS- TDPSA | | RL- SYFVA | PLI A TVAC | FF- -FT | 43 |
| SEQ_ID_NO_1435 | TG- LSELHP | | TPF- SYLVT | AFLLAVVYS | LQ- VHL- | 50 |
| SEQ_ID_NO_1436 | -- MTTLWG | | TGF- LCLI A | GL- -I | -TR | 62 |
| SEQ_ID_NO_1437 | | | PV- PWVT | GLI AF CI LA | LVQ- EE | 64 |
| SEQ_ID_NO_1438 | S- TDPSA | | TPF- SYLVT | AFLLAVVYS | LQ- GP | 50 |
| SEQ_ID_NO_1439 | H- FPADS | | SW- PFVIA | VLLV FFVLT | TRN- FFSST | 43 |

Figure 6A

| SEQ_ID_NO_1429 | -----      | RKG-SV   | VPLANPPDSL | -FGTGKTRRS  | FVKLSREILA | 73  |
| SEQ_ID_NO_1430 | -----      | RKG-SV   | VPLANPPESL | -FGTGKTRRS  | FVKLSREILA | 68  |
| SEQ_ID_NO_1431 | RWSLDSL    | KH       | LPIVNNKEWY | SLSGRKAKLR  | FLAESKSLLE | 75  |
| SEQ_ID_NO_1432 | -----RSAF- | DA       | LPIVNKPKFG | PIFSTLARWR  | FIHQSKKILE | 80  |
| SEQ_ID_NO_1433 | -----RAHL- | KH       | LPLLNPSKGL | PLFNIESKRE  | FVFNSKELLA | 78  |
| SEQ_ID_NO_1434 | -----SK-   | PN       | APCLNPQGFF | DIASGRAKKQ  | FLFGLRSMLK | 77  |
| SEQ_ID_NO_1435 | -----RFP-  | KN       | TKHLNPKGPL | EFSDTRPKKE  | FVYGSRQMLA | 85  |
| SEQ_ID_NO_1436 | -----GPKP- | TV       | LPVVNPPGTF | ELTANRVKKE  | WLVDARQIIR | 98  |
| SEQ_ID_NO_1437 | ----DFPHT  | D        | YPLQNPRKFW | DVTAWKSKWD  | FIFGVRKILE | 100 |
| SEQ_ID_NO_1438 | -----RFP-  | KN       | TKHLNPKGPL | EFSDTRPKKE  | FVHGSRPMLA | 85  |
| SEQ_ID_NO_1439 | -----KAA-  | GH       | IPLVNPPKFY | DIGAIWAKID  | CLHARRLLA  | 78  |

| SEQ_ID_NO_1429 | KARSLFPNEP | FRLI  | TDWGE   | VLILPPDFAD  | EIRNDPRLSF | 112 |
| SEQ_ID_NO_1430 | KARNLFPDEP | FRLI  | TDWGE   | VLILPPEFAD  | EIRNDPRLSF | 107 |
| SEQ_ID_NO_1431 | EARKRYPQQP | FRIL  | SNWGV   | LLVLPSCFAD  | EIRNDQRLSF | 114 |
| SEQ_ID_NO_1432 | EGQKCYSNRP | FRIW- | TDWGE   | VLMLTPDYAH  | EIRNDPHLSF | 119 |
| SEQ_ID_NO_1433 | KGRKLFPKSP | YRMI- | TDLGE   | IVELPVEQTD  | EIRNDPRLSF | 117 |
| SEQ_ID_NO_1434 | TWFDANPHKP | ASVE- | SDDGP   | MTVLPPSMAN  | EIRSDPRLSF | 116 |
| SEQ_ID_NO_1435 | NWFKANPNKP | CRVI  | SDFGE   | AIVLPPRMAN  | EIKNDDRLSF | 124 |
| SEQ_ID_NO_1436 | RGFEKFPGKP | FNMI  | AADVGL  | TTVLPPEYAS  | EIRNNPSLSF | 138 |
| SEQ_ID_NO_1437 | KRIAEAPDQP | YRIL  | TDFGD   | MTILPPDYAN  | EIRNSDDLSF | 139 |
| SEQ_ID_NO_1438 | NWFKANPNKP | CRVI  | SDFGE   | AIVLPPRMAN  | EIKNDDRLSF | 124 |
| SEQ_ID_NO_1439 | RGV--SSGRP | FRLL  | TDLGE   | MIVLPAHFAT  | EIRSDPRLSF | 115 |

Figure 6B

| | | | | | |
|---|---|---|---|---|---|
| SEQ_ID_NO_1429 | SKAAMQDNHA | GIPGFETVAL | VGREDQLIQK | VARKQLTKHL | 152 |
| SEQ_ID_NO_1430 | SKAAMQDNHA | GIPGFETVAL | VGREDQLIQK | VARKQLTKHL | 147 |
| SEQ_ID_NO_1431 | SKAALQDSHG | HIPGLETVKL | VARDDQLIQT | VARKHLTKHL | 154 |
| SEQ_ID_NO_1432 | SGAVKIDGHA | DIPGFETVKL | LSHPDNLIQL | VARKQLTRHL | 159 |
| SEQ_ID_NO_1433 | GSAFGEDFHG | HLPGFQGAAV | DSYDDAVLQT | LVRKQLTKCI | 157 |
| SEQ_ID_NO_1434 | VEFSAKEFHT | SIPGFEAFNE | GTRDESITLT | VINKDLTKRL | 155 |
| SEQ_ID_NO_1435 | TRWTYKAFHG | HLPGFEGFGE | ASRESHIVQE | VIMRDLTKYL | 164 |
| SEQ_ID_NO_1436 | VAFMAHLFFS | ELPGFEPTRE | GMFDNDIGIT | VVHKYLTVNL | 178 |
| SEQ_ID_NO_1437 | DRVVEKNFQA | HLPGLDVFKE | ENLHKTVLRH | VIRTRLTQFL | 179 |
| SEQ_ID_NO_1438 | TRWTYKAFHG | HLPGFEGFGE | VSRESHIVQE | VIMRDLTKYL | 164 |
| SEQ_ID_NO_1439 | AEVIEQNFHS | RFPGFEGFRM | GTTDAHLSRD | LANNQLTHTL | 155 |

| | | | | | |
|---|---|---|---|---|---|
| SEQ_ID_NO_1429 | SAVIEPLSRE | STLAVSLNFG | E--ITEWRAI | RLKPAILDII | 190 |
| SEQ_ID_NO_1430 | SE-------- | ---------- | ---------- | ---LDII | 153 |
| SEQ_ID_NO_1431 | AKVIQPLSEE | TEFALDQNFG | H--NL----- | --PAILDII | 183 |
| SEQ_ID_NO_1432 | AAVIQPLSSV | TEEEALIKNL | KL-SQEWSEI | YLKYAVLDII | 197 |
| SEQ_ID_NO_1433 | AQIIEPVSAE | AAQALADKFG | DL-SEDWREM | EVKSVVLDTV | 195 |
| SEQ_ID_NO_1434 | AQVTQPLAEE | TTLAMQEIFT | DL-NKEWHLI | NVREKILHLV | 193 |
| SEQ_ID_NO_1435 | NKVTEPLAQE | TSMAMEANLP | KAANGEWSTI | NLRSKILPIV | 204 |
| SEQ_ID_NO_1436 | ARITEPLSRE | ATAALKDIFT | DF-NSEWHDA | NLKAINLALV | 216 |
| SEQ_ID_NO_1437 | SKVTAPLSNE | TALTLQDVFT | DL-QKEWHTI | ILKDEIVKIV | 217 |
| SEQ_ID_NO_1438 | NKVTEPLAQE | TSMAMEAILP | KAANGEWSTI | NLRSKILPIV | 204 |
| SEQ_ID_NO_1439 | AKVTEALSEE | CTAAMTDHFP | A--TKEWAEI | CLREHVLQLV | 193 |

Figure 6C

| SEQ_ID | Sequence | Pos |
|---|---|---|
| SEQ_ID_NO_1429 | ARISSRIYLG DQLCRNEAWL KITKTYTTNF YTASTNLRMF | 230 |
| SEQ_ID_NO_1430 | ARISSRIYLG DQLCRNEAWL KITKTYTTNF YTASTNLRMF | 193 |
| SEQ_ID_NO_1431 | ARISSRIYLG DELCRNTAWL ATTKVYTSAF FAAPVKLGLI | 223 |
| SEQ_ID_NO_1432 | ARLSARVFLG EDLYQNEEWL SIVKNYATHF FTASSDLRKV | 237 |
| SEQ_ID_NO_1433 | ARISSRVFLG EELCRNEDWL RATKEYTVNF FVAGTHLRMI | 235 |
| SEQ_ID_NO_1434 | ARLSSRVFLG EELCRDEAWL KITREHAMNG FVAADLLRAW | 233 |
| SEQ_ID_NO_1435 | ARLSSRIFLG EELCRNEEWL KVTQQYTIDG FGAAEDLRLW | 244 |
| SEQ_ID_NO_1436 | ARLSSRIFLG EELCRNEEWL KITVNYTVDV MKAAERLRRV | 256 |
| SEQ_ID_NO_1437 | SRISARVFTG EDLCRNPEWQ KITADYAMTC FLAADMVRMF | 257 |
| SEQ_ID_NO_1438 | ARISSRVFLG EELCRNVEWL KVTQQYTIDG FGAAEDLRLW | 244 |
| SEQ_ID_NO_1439 | ARLSSRVFLG DAGANNSAWL RITTEYTKTA YIAAYLLRLW | 233 |

| SEQ_ID | Sequence | Pos |
|---|---|---|
| SEQ_ID_NO_1429 | PRSIRPLAHW FLPECRKLRQ ERKDALGIIT PLIERRRELR | 270 |
| SEQ_ID_NO_1430 | PRSIRPLAHW FLPECRKLRQ ERKDAVGIIT PLIERRRELR | 233 |
| SEQ_ID_NO_1431 | PAPLRRLAHW LIPECKILRE QVQEARRIIE PLVRRRQALR | 263 |
| SEQ_ID_NO_1432 | PWAFRSLVHW FVPSCRALRL ERYNARRVLE PVIPYISQRRQLK | 277 |
| SEQ_ID_NO_1433 | PRPLRRVLHW FVPKCRELRA SFDEARRIIL PVIEKRRAAR | 275 |
| SEQ_ID_NO_1434 | PEALRPVVSW FMPHCRTARS QIREAEKIIG PVISKRREAK | 273 |
| SEQ_ID_NO_1435 | PAALRPIVHW FLPSCQRARA DVRVARSILD PVLKKRRQEK | 284 |
| SEQ_ID_NO_1436 | PGPLRRIVHW FLPEAQKCRD EVKRAGKVIR PVLEKRRREK | 296 |
| SEQ_ID_NO_1437 | PKPIRPLVHR ILPLSIKVRS DVKKARAIVE PVLAERKKIK | 297 |
| SEQ_ID_NO_1438 | PAALRPIVHW FLPSCQRARA DVRVARSILD PVLKKRRQEK | 284 |
| SEQ_ID_NO_1439 | PPVLRPFVHW FIPHCRKLRA QVAEARHILV GLIEQRHQGR | 273 |

Figure 6D

| SEQ_ID_NO | | | | | |
|---|---|---|---|---|---|
| SEQ_ID_NO_1429 | RAAI AAGQPL | PVFHDAI DWS | EQEAEAAGTG | ASFDPVI FQL | 310 |
| SEQ_ID_NO_1430 | RAAI AAGQPL | PVFHDAI DWS | EQEAEAAGSG | SAFDPVI FQL | 273 |
| SEQ_ID_NO_1431 | AKALAEGCPT | PQFNDALGWA | AEESAF- -KNG | KDYDPAI TQL | 301 |
| SEQ_ID_NO_1432 | EAAKTAGGTP | LHFEDAI EWA | EVEAR- - VKG | TKYDPVI FQL | 315 |
| SEQ_ID_NO_1433 | AAALAAGKKI | PEFHDAI DWA | DQEAAI - -ARG | VTYDPAI LQL | 313 |
| SEQ_ID_NO_1434 | DAALRAGREA | PLHNDAI EWF | EQAS- - - - KG | KPYNPALSQL | 309 |
| SEQ_ID_NO_1435 | AAN- GG- - K | AEHDDAI EWF | ERTAL- - - KG | KYYDPAVAQL | 316 |
| SEQ_ID_NO_1436 | ATMESEGKEA | LQYNDAI EWF | EQMAK- - SQG | TSYDPEVVQL | 334 |
| SEQ_ID_NO_1437 | EEARRRGEPI | PKFDDAI EWC | EELE- - - - QD | VGFDMATFQL | 333 |
| SEQ_ID_NO_1438 | AAN- GG- - K | AQHDDAI EWF | ERTAL- - - KG | EYYDPAVAQL | 316 |
| SEQ_ID_NO_1439 | VAAELASQPV | PQYNDAI EWF | EQDFAV- TRD | GRHDPAVAQL | 312 |

| SEQ_ID_NO | | | | | |
|---|---|---|---|---|---|
| SEQ_ID_NO_1429 | TLSLLAI HTT | YDLLQQTMI D | LGRHPEYI EP | LRQEVVQLLR | 350 |
| SEQ_ID_NO_1430 | TLSLLAI HTT | YDLLQQTMI D | LGRHPEYI EP | LRQEVVQLLR | 313 |
| SEQ_ID_NO_1431 | ALSMLAI HTT | YDLFQQCI LD | LAQNPHFI ED | LRQEAI EVI Q | 341 |
| SEQ_ID_NO_1432 | TLSLLAI HTT | YDLLEMCMI D | LAKRPDCI ED | LRKEVI TVLR | 355 |
| SEQ_ID_NO_1433 | MLAVAAI HTT | ADLVTEI VLQ | LALHPEHFGP | LRGEVLHI LR | 353 |
| SEQ_ID_NO_1434 | FLSTVAI HTT | TDLLCQTMI D | I ARHPEYFEP | LREEVTRVLA | 349 |
| SEQ_ID_NO_1435 | VLSLVAI HTT | SDLTCQVMTN | LMQNPEFI AP | LREEMI QVLS | 356 |
| SEQ_ID_NO_1436 | FLSTVAI HTT | SDLLTVMAD | LARNPED EP | LRAEI AAVLK | 374 |
| SEQ_ID_NO_1437 | AMAVAAI HTT | SDELTQI LLD | LAQHPEYI EP | LREEMI RVLS | 373 |
| SEQ_ID_NO_1438 | VLSLVAI HTT | SDLTCQVMTN | LMQNPEFI GP | LREEVAGAI Q | 356 |
| SEQ_ID_NO_1439 | I LAQAAI ETT | TDLLTQVI LD | LAQHPEL GT | LREEVAGAL Q | 352 |

Figure 6E

| SEQ_ID_NO | | | | | |
|---|---|---|---|---|---|
| SEQ_ID_NO_1429 | EEGWKKTTLF | KMKLLDSAIK | ESQRMKPGSI | VTMRRYVTED | 390 |
| SEQ_ID_NO_1430 | EEGWKKTTLF | KMKLLDSAIK | ESQRMKPGSI | VTMRRYVTED | 353 |
| SEQ_ID_NO_1431 | QYGWTKQGLY | HMKLLDSALK | ETQRLKPGSI | VTMRRYVLED | 381 |
| SEQ_ID_NO_1432 | KDGWTKNALY | NMKLLDSALK | ESQRLKPGSM | TSMRRYATSD | 395 |
| SEQ_ID_NO_1433 | SEGLKKSSLH | SMQLLDSVVK | EAQRHKPPGV | ASLRRRVEKP | 393 |
| SEQ_ID_NO_1434 | QDGWKKTSLH | NMKLLDSVIK | ESQRLKPLQL | ASMQRLAVKD | 389 |
| SEQ_ID_NO_1435 | EGGWKKTSLY | DMKLLDSVLK | ESQRVKPTGV | ASMRRYAEKD | 396 |
| SEQ_ID_NO_1436 | DGGWKKTSLT | KMRLLDSVLK | ESLRLKPIAV | VSMRRVAMDH | 414 |
| SEQ_ID_NO_1437 | EDGWDKLSLY | NMKLLDSVIK | ETQRLRPIGL | VAMHRELKD | 413 |
| SEQ_ID_NO_1438 | EGGWKKTSLY | NMKLLDSVIK | ESQRVKPIGV | ASMRRYAEKD | 396 |
| SEQ_ID_NO_1439 | EGGWRKSSLY | DMKLLDSVLK | ESQRLKPLAM | TSMHRLVLEE | 392 |

| SEQ_ID_NO | | | | | |
|---|---|---|---|---|---|
| SEQ_ID_NO_1429 | ITLSSGLTLK | KGTRLNVDNR | RLDDPKIYDN | PEVYNPYRFY | 430 |
| SEQ_ID_NO_1430 | ITLSSGLTLQ | KGTRLNVDNR | RLDDPKIYEN | PEVYNPYRFY | 393 |
| SEQ_ID_NO_1431 | QLSNGLILK | KGTRINIDTQ | RMRDPDLHED | PLKYDAFRFY | 421 |
| SEQ_ID_NO_1432 | VQLRDGVVLK | KGNRLNVLTL | H-RSPDLFPS | PDTYDPYRFY | 434 |
| SEQ_ID_NO_1433 | TLSNGLNLK | LGDRLAIDTY | RMGDPELHQD | PETWDPYRFL | 433 |
| SEQ_ID_NO_1434 | VQLSDGTFIP | KGTASCVSSH | ALWDPDVYEA | PDTWDGHRFL | 429 |
| SEQ_ID_NO_1435 | VTLSDGTFIP | KGGFVAVSAH | DMWNSEVYEQ | AEKWDGRRFL | 436 |
| SEQ_ID_NO_1436 | LKLSDGTFLP | KGTKMAVSSH | RMWDPDVYEN | PEQWDGFRYV | 454 |
| SEQ_ID_NO_1437 | DLAGGVHLP | KGTRIAISSH | RMRDPAYYPS | PNEYDGYRFL | 453 |
| SEQ_ID_NO_1438 | VTLSDGTFIP | KGGFVAVSAH | DMWNSEVYEQ | ADKWDGRRFL | 436 |
| SEQ_ID_NO_1439 | ITLSDGTILP | KGSVLGVSAD | RMWNPSVHEN | PAQFDGFRFQ | 432 |

Figure 6F

| SEQ_ID_NO | | | | | | |
|---|---|---|---|---|---|---|
| SEQ_ID_NO_1429 | DMRSEA-GK | DHGAQLVSTG | SNHMGFGHGQ | HSCPGRFFAA | 468 |
| SEQ_ID_NO_1430 | DMRSEA-GK | DHGAQLVSTG | SNHMGFGHGQ | HSCPGRFFAA | 431 |
| SEQ_ID_NO_1431 | KMRQQP--GG | EHTAQLVSTS | PDHLGFGHGE | HSCPGRFFAA | 459 |
| SEQ_ID_NO_1432 | NIRGQP--GK | ENWAQLVSTS | VEHMGFGHGE | HSCPGRFFAA | 472 |
| SEQ_ID_NO_1433 | RMAEQP--GK | ANYAQLVMTS | PDHLAFGHGD | HACPGRFFAA | 471 |
| SEQ_ID_NO_1434 | RQRGLPL-GK | ENFSQLVSTS | ENHLGFGHGK | HACPGRFFAA | 467 |
| SEQ_ID_NO_1435 | RMRETPGAGK | ENVAQLVSTA | PEHLGFGHGQ | HACPGRFFAA | 476 |
| SEQ_ID_NO_1436 | NLRETP--GQ | DKHAQFVSTS | ERHLGFGHGK | HACPGRFFAA | 492 |
| SEQ_ID_NO_1437 | RMRDELGAGK | DGDAHFVTTS | PQHLGFGHGK | HACPGRFFAS | 493 |
| SEQ_ID_NO_1438 | RMRETPGAGK | ENAAQLVSTA | PEHLGFGHGK | HACPGRFFAA | 476 |
| SEQ_ID_NO_1439 | RMRDQPGFGS | TNQAHLVSTS | VNHLAFGHGK | HACAGRFFVA | 471 |

| SEQ_ID_NO | | | | | | |
|---|---|---|---|---|---|---|
| SEQ_ID_NO_1429 | NEIKVALCHI | LVKYDWKLCP | DT-ETKPDTR | GMIAKSSPVT | 507 |
| SEQ_ID_NO_1430 | NEIKVALCHI | LVKYDWKLCP | DT-ETKPDTR | GMIAKSSPVT | 470 |
| SEQ_ID_NO_1431 | NEIKVAMAHM | LIKYEWKPAG | HS-SAGPDVK | GLLMKSGAGA | 498 |
| SEQ_ID_NO_1432 | NEIKVALAHI | LVKYDWKLSD | EA-GGCTEVK | GMVEKAGSKV | 511 |
| SEQ_ID_NO_1433 | YEIKIMCHL | LLKYEWEALP | AIT-DVSPMVL | GFTNASNPTA | 510 |
| SEQ_ID_NO_1434 | NEIKIALAHL | LLEYEWRLPE | GE-ALDVEDF | GITPIMNQTL | 506 |
| SEQ_ID_NO_1435 | NEIKIALVHL | LNYEWRLPE | GS-DPKIRTF | GFSMGVDPSL | 515 |
| SEQ_ID_NO_1436 | SELKVALCHI | LMKYDFELAP | GT-VVQHRYS | GASYYADPAI | 531 |
| SEQ_ID_NO_1437 | NEVKVALCHI | LLKYNWRLAP | GV-EPKIEQF | GLTIGCDPVA | 532 |
| SEQ_ID_NO_1438 | NEIKIALVHL | LNYEWRLPE | GS-DPKIRTF | GFSMGVDPSL | 515 |
| SEQ_ID_NO_1439 | HEAKIALTHL | LLKYDWKLAS | TSANAKPMEF | GLVLQANPKA | 511 |

Figure 6G

| | | | | |
|---|---|---|---|---|
| SEQ_ID_NO_1429 | DILIKRRESV | E- | ---------- | LDLEAI | 524 |
| SEQ_ID_NO_1430 | DILIKRRGSV | E- | ---------- | LDLEAI | 487 |
| SEQ_ID_NO_1431 | QIDIRRRETV | E- | ---------- | ----IA | 511 |
| SEQ_ID_NO_1432 | KILVRQRQDV | E- | ---------- | SVLDEA | 528 |
| SEQ_ID_NO_1433 | RVRVRRRKHV | E- | ---------- | LDMDCL | 527 |
| SEQ_ID_NO_1434 | KMEFRKRD-- | -- | ---------- | ------ | 514 |
| SEQ_ID_NO_1435 | KVEYKGRQPE | I- | ---------- | ---EL | 528 |
| SEQ_ID_NO_1436 | RVMLRRRNVA | L- | ---------- | PSWFER | 548 |
| SEQ_ID_NO_1437 | KVEIRRRDYH | LE | ALAGKEEI | DVRDLPVK | 560 |
| SEQ_ID_NO_1438 | KVEYKGRQPE | L- | ---------- | ---EL | 528 |
| SEQ_ID_NO_1439 | KICLRGRQEI | S- | ---------- | ---KSPF | 526 |

Figure 6H

| SEQ_ID_NO_1542 | MPHKDNLLES | PVGKSVTATI | AYHSGPALPT | SPIAGVTTLQ | 40 |
| --- | --- | --- | --- | --- | --- |
| SEQ_ID_NO_1543 | MPHKDTPLES | PVGKNVTATI | AYHSGPALPT | SPIAGVTTLQ | 40 |
| SEQ_ID_NO_1544 | MPHKDTPLEQ | PVGKNVTATI | AYHSGPALPT | SPIAGVTTLQ | 40 |
| SEQ_ID_NO_1545 | MSQQDTHHEP | PVGKNVTATI | AYHSGPALPT | SPIAGVTTLE | 40 |

| SEQ_ID_NO_1542 | DCTQQAVAVT | DIRPSVSSFT | LDGNGFQVVK | HTSAVGSPPY | 80 |
| --- | --- | --- | --- | --- | --- |
| SEQ_ID_NO_1543 | DCTQQVVAVT | DIRPSVSSFT | LDGNGFQVVK | HASAVGSPPY | 80 |
| SEQ_ID_NO_1544 | DCTQQVVAVT | DIRPSVSSFT | LDGNGFQVVK | HTSVVGSPPY | 80 |
| SEQ_ID_NO_1545 | DCTQQLVAVT | DIRPSVSSFT | LDGNGFQVVK | HTSAVSSPPY | 80 |

| SEQ_ID_NO_1542 | DHSSWTDPVV | RKEVYDPEII | ELAKSLTGAK | KVMILLASSR | 120 |
| --- | --- | --- | --- | --- | --- |
| SEQ_ID_NO_1543 | NHSSWTDPVV | RKEVYDPEII | ELAKSLTGAK | KVMILLASSR | 120 |
| SEQ_ID_NO_1544 | DHSSWTDPVV | RKEVYDPEII | ELAKSLTGAK | KVMILLASSR | 120 |
| SEQ_ID_NO_1545 | DHSSWTGPVV | RKEVYDPEII | ELAKSVTGAK | KVMILLASSR | 120 |

| SEQ_ID_NO_1542 | NVPFKEPELA | PPYPMPGKSS | SGSKERE---  | -AIPANELPT | 156 |
| --- | --- | --- | --- | --- | --- |
| SEQ_ID_NO_1543 | NVPFKEPELA | PPYPMPGKSN | SGSKEGG---  | -ANPANELPT | 156 |
| SEQ_ID_NO_1544 | NVPFKEPELA | PPYPMPSKSN | KGSKEEV---  | -AKPTDELPT | 156 |
| SEQ_ID_NO_1545 | NVPFKEPELA | PPYPMPSKSS | NGCNGGETGP | AVRPQHELPT | 160 |

| SEQ_ID_NO_1542 | TRAKGFQKGE | EEGPVRKPHK | DWGPSGAWNT | LRNWSQELID | 196 |
| --- | --- | --- | --- | --- | --- |
| SEQ_ID_NO_1543 | TRAKGFQKGE | EEGPVRKPHK | DWGPSGAWNT | LRNWSQELID | 196 |
| SEQ_ID_NO_1544 | TRAKGFQKGE | EEGPVRKPHK | DWGPSGAWNT | LRNWSQELID | 196 |
| SEQ_ID_NO_1545 | TRAKGFQKGE | EEGPVRKPHK | DWGPSGAWNT | LRNWSQELID | 200 |

| SEQ_ID_NO_1542 | EAGDIIKAGD | EAAKLPGGRA | KNYQGRRWAL | YTTWRPLKIV | 236 |
| --- | --- | --- | --- | --- | --- |
| SEQ_ID_NO_1543 | EAGDIIKAGD | EAAKLPGGRA | KNYQGRRWAL | YTTWRPLKPV | 236 |
| SEQ_ID_NO_1544 | EADDIIKAGD | EAAKLPGGRA | KNYQGRRWAL | YTPWRPLKPV | 236 |
| SEQ_ID_NO_1545 | EAGDIIKAGD | VAAELPGGRA | KNYQGRRWAL | YTTWRPLKPV | 240 |

Figure 7A

| | | | | | |
|---|---|---|---|---|---|
| SEQ_ID_NO_1542 | KRDPMAYVDY | WTADEEDGVS | FWRNPPGVHG | TFESDVLLTK | 276 |
| SEQ_ID_NO_1543 | KRDPMAYVDY | WTADGEDGVS | FWRNPPGVHG | TFESDVLLTK | 276 |
| SEQ_ID_NO_1544 | KRDPMAYVDY | WTADDEDGVS | LWRNPPGVHG | TFESDVLLTK | 276 |
| SEQ_ID_NO_1545 | KRDPMAYVDY | WTADEQDGVS | FWRNPPGVHG | TFESDVLLTK | 280 |

| | | | | | |
|---|---|---|---|---|---|
| SEQ_ID_NO_1542 | ANPKHKWYWM | SDQTPDEVLL | MKIMDTESEK | DGSEIAGGVH | 316 |
| SEQ_ID_NO_1543 | ANPKHKWYWM | SDQTPDEVLL | MKIMDTESEK | DGSGIAGGVH | 316 |
| SEQ_ID_NO_1544 | ANPKHKWYWM | SDQTPDEVLL | MKIMDTESEK | DGSDIAGGVH | 316 |
| SEQ_ID_NO_1545 | ANPKHKWYWM | SDQTPDEVLL | MKIMDTESEK | DGSDVAGGVH | 320 |

| | | | |
|---|---|---|---|
| SEQ_ID_NO_1542 | HCSFHLPGTE | KEEVRESIET | KFIAFW | 342 |
| SEQ_ID_NO_1543 | HCSFHLPGTE | KEEVRESIET | KFIAFW | 342 |
| SEQ_ID_NO_1544 | HCSFHLPGTE | KEEVRESIET | KFIAFW | 342 |
| SEQ_ID_NO_1545 | HCSFHLPGTE | DEEVRESIET | KFIAFW | 346 |

Figure 7B

| | | | | | |
|---|---|---|---|---|---|
| SEQ_ID_NO_1386 | MNHS- | SSY | YYEFYKDHSH | TFRRSMSENT | LI SSCLALAT | 38 |
| SEQ_ID_NO_1387 | MANHS- | SSY | YHEFYKDHSH | TVLTLMSEKP | VI LPSLI LGT | 38 |
| SEQ_ID_NO_1388 | MATLEPTTGY | I AELI S---- | -----TSNLP | SVTFVVTAVI | | 31 |

| | | | | | |
|---|---|---|---|---|---|
| SEQ_ID_NO_1386 | CAI LLSI QWL | KPQPLI MVNG | RKFGELSNVR | AKRDFTFGAR | 78 |
| SEQ_ID_NO_1387 | CAVLLCI QWL | KPQPLI MVNG | RKFGELSNVR | AKRDFTFGAR | 78 |
| SEQ_ID_NO_1388 | LAVFYTLQRR | KS- TVPLI NP | KRWFEFSDYR | I KQEFVHNAI | 70 |

| | | | | | |
|---|---|---|---|---|---|
| SEQ_ID_NO_1386 | QLLEKGFKMS | PDKPFRI MGD | VGELHI LPPK | YAYEVRNNEK | 118 |
| SEQ_ID_NO_1387 | QLLEKGLKMS | PDKPFRI MGD | VGELHI LPPK | YAYEVRNNEK | 118 |
| SEQ_ID_NO_1388 | PLVKQGFAAI | GNKPFRI LAD | SGELTVLPPD | VANEI KSNDH | 110 |

| | | | | | |
|---|---|---|---|---|---|
| SEQ_ID_NO_1386 | LSFTMAAFKW | FYAHLPGFEG | FREGTNESHI | MKLVARHQLT | 158 |
| SEQ_ID_NO_1387 | LSFTMAAFKW | FYAHLPGFEG | FREGTNESHI | MKLVARHQLT | 158 |
| SEQ_ID_NO_1388 | MSFELSI AKQ | FFGHLPGFEV | ENATGMNTKV | SKSLVQRQLT | 150 |

| | | | | | |
|---|---|---|---|---|---|
| SEQ_ID_NO_1386 | HQLTLVTGAV | SEECALVLKD | VYTDSPEWHD | TAKDANMKF | 198 |
| SEQ_ID_NO_1387 | HQLTLVTGAV | SEECALVLKD | VYTDSPEWHD | TAKDANMKL | 198 |
| SEQ_ID_NO_1388 | THLNKVTKPL | SDEASLSLQE | LTDNKEWHE | I TKNEVLQI | 190 |

| | | | | | |
|---|---|---|---|---|---|
| SEQ_ID_NO_1386 | MARI TERVFL | GKEMCRNPQW | LRI TSTYAVI | AFRAVEELRL | 238 |
| SEQ_ID_NO_1387 | MARI TSRVFL | GKEMCRNPQW | LRI TSTYAVI | AFRAVEELRL | 238 |
| SEQ_ID_NO_1388 | ARLSSKVFT | GDELCHDKRW | LDLTVNYTLM | AFAAADSLRM | 230 |

| | | | | | |
|---|---|---|---|---|---|
| SEQ_ID_NO_1386 | WPSWLRPVVQ | WFMPHCTQSR | ALVQEARDLI | NPLLERRREE | 278 |
| SEQ_ID_NO_1387 | WPSWLRPVVQ | WFMPHCTQSR | ALVQEARDLI | NPLLERRREE | 278 |
| SEQ_ID_NO_1388 | WPPYLRSLVH | WFLPKCRASR | AEVARARTVI | EPI LKRRAEQ | 270 |

Figure 8A

| SEQ_ID_NO_1386 | KAEAERTGEK | VL TYNDAVEW | LDDLAREKGV | GYDPACAQLS | 317 |
| --- | --- | --- | --- | --- | --- |
| SEQ_ID_NO_1387 | KAEAERTGEK | VL TYNDAVEW | LDDLAREKGV | GYDPACAQLS | 317 |
| SEQ_ID_NO_1388 | KA ALAAQGKK | APEI NDAI EW | FTTATTI EGF | TLDPVI AQLG | 310 |

| SEQ_ID_NO_1386 | LSVAALHSTT | DFFTQVMFDI | AQNPELI EPL | REEI I SVLGK | 357 |
| --- | --- | --- | --- | --- | --- |
| SEQ_ID_NO_1387 | LSVAALHSTT | DFFTQVMFDI | AQNPELI EPL | REEI I AVLGK | 357 |
| SEQ_ID_NO_1388 | LSLAAI HTTS | DL ST QVI L DI | AS HPEI I EPL | RKEMI ESLSE | 350 |

| SEQ_ID_NO_1386 | QGWSKNSLYN | LKLMDSVLKE | SQRLKPI AI A | SMRRFTTHNV | 397 |
| --- | --- | --- | --- | --- | --- |
| SEQ_ID_NO_1387 | QGWSKNSLYN | LKLI DSVLKE | SQRLKPI AI A | SMRRFTTHNV | 397 |
| SEQ_ID_NO_1388 | GGWKNSLYK | LKLLDSVI KE | SQRMKPI AS I | SMS RL TT NV | 390 |

| SEQ_ID_NO_1386 | ELSDGVI LPK | NKLTLVSAHQ | HWDPEYYKDP | LKFDGYRFFN | 437 |
| --- | --- | --- | --- | --- | --- |
| SEQ_ID_NO_1387 | KLSDGVI LPK | NKLTLVSAHQ | HWDPEYYKDP | LKFDGYRFFN | 437 |
| SEQ_ID_NO_1388 | SL SDGT FL PR | NTA A VSSHR | MWDPSTHTNP | DQWDGYRFYN | 430 |

| SEQ_ID_NO_1386 | MRREPGKESK | AQLVSATPDH | MGFGYGLHAC | PGRFFASEEI | 477 |
| --- | --- | --- | --- | --- | --- |
| SEQ_ID_NO_1387 | MRREPGKESK | AQLVSATPDH | MGFGYGLHAC | PGRFFASEEI | 477 |
| SEQ_ID_NO_1388 | KRQEPGQENL | SQLVST SPDH | LAF GHGQHAC | PGRFFAANEI | 470 |

| SEQ_ID_NO_1386 | KI ALSHI LLK | YDFKPVEGSS | MEPRKYGLNM | NANPTAKLSV | 517 |
| --- | --- | --- | --- | --- | --- |
| SEQ_ID_NO_1387 | KI ALSHI LLK | YDFKPVEGSS | MEPRKYGLNM | NANPTAKLSV | 517 |
| SEQ_ID_NO_1388 | KVFL CHLLLK | YDL KI VEGSM | KPF PYSFSM | NANPF APL M | 510 |

| SEQ_ID_NO_1386 | RRRKEEI A - - - - | 526 |
| --- | --- | --- |
| SEQ_ID_NO_1387 | RRRKEEI A - - - - | 526 |
| SEQ_ID_NO_1388 | RRREDVL DL D ALDA | 524 |

| SEQ_ID_NO | | | | | |
|---|---|---|---|---|---|
| SEQ_ID_NO_1274 | ---PPRVVLPMNL | ----------- | ----------- | ---IFLGKYTH-- | 23 |
| SEQ_ID_NO_1275 | PPLVVLPHCT | YQEVLHAPES | ELSFGAELYD | MFLSAHTK-- | 101 |
| SEQ_ID_NO_1276 | PELVVLPMST | HEEVRTLTEE | KVSFQEEVHR | VFEGKHTG-- | 113 |
| SEQ_ID_NO_1277 | SDILVIPNKY | HDEMRNLPED | KASFMQDLSH | NLLGKYSTTL | 113 |
| SEQ_ID_NO_1278 | SDILVIPNKY | VEELRSLPDE | KISAIRAHIK | NLLGKYSTTL | 195 |
| SEQ_ID_NO_1279 | | VEELRSLPDE | KISAIRAHIK | | 139 |

| SEQ_ID_NO | | | | | |
|---|---|---|---|---|---|
| SEQ_ID_NO_1274 | ---LGEPRMEVVE | --AIRVDMTRNL | ---SGILLPI | VKFAMKQMF- | 23 |
| SEQ_ID_NO_1275 | VGTDFPVVVK | TVKTDLTRHS | QEEGALEDE | TNYALDTEF- | 140 |
| SEQ_ID_NO_1276 | IGENTPPLIK | TIKADLTRHM | ASTVGALQDE | ARYALNEEF- | 152 |
| SEQ_ID_NO_1277 | LLESDLHTR | MLQTKLTPNL | ASTVEALQDE | LLFAMDQEIP | 151 |
| SEQ_ID_NO_1278 | LLESDLHTR | MLQTKLTPNL | GSFIEVIESE | LHFAMEKEIP | 235 |
| SEQ_ID_NO_1279 | | | GSFIEVIESE | | 179 |

| SEQ_ID_NO | | | | | |
|---|---|---|---|---|---|
| SEQ_ID_NO_1274 | PRTSKMSSVS | LYDMMLRTVA | LLSGRAFVGL | PLCRDEGWLQ | 63 |
| SEQ_ID_NO_1275 | GVLEDWKSFN | AYHLVRLVA | LMSGRVFVGL | PLSRDEEWM Q | 180 |
| SEQ_ID_NO_1276 | GTGESWTKVV | LFEKVVRIVA | LVSGRVFVGR | PLSRNEEWLQ | 192 |
| SEQ_ID_NO_1277 | GSCENWTKVD | LTKAIPRMVA | LLSGRAFVGK | PLSRNEEWM | 191 |
| SEQ_ID_NO_1278 | ANLDDWQSVN | VFHIVLRIVA | RISARVFLGV | PACRNEEWLQ | 275 |
| SEQ_ID_NO_1279 | ADLHDWQNVN | VFHIVLRIVA | RISARVFLGV | PACRNEEWLQ | 219 |

| SEQ_ID_NO | | | | | |
|---|---|---|---|---|---|
| SEQ_ID_NO_1274 | ASIGYTVQCV | SIRDQLFTWS | PVLRPIGPF | LPSVRSVRRH | 103 |
| SEQ_ID_NO_1275 | ASITFATDCG | KCRMAALEWN | PWWRPWLPF | LPEVRHMRRT | 220 |
| SEQ_ID_NO_1276 | ASIQYTIDCA | KARDAANEWP | VMTRYFVPF | LPEIKKVKSH | 232 |
| SEQ_ID_NO_1277 | ATVDYTVDTV | KAKDEVLQYP | ALIQNLAVSF | LSQIRTVKQH | 231 |
| SEQ_ID_NO_1278 | TSIHYTENVF | ATVMLLRRFP | KWMHPIVGHL | LPSYWAIHRN | 315 |
| SEQ_ID_NO_1279 | TSIHYTENVF | ATVMLLRRFP | KWMHPIVGHL | LPSYWAIHSN | 259 |

Figure 9B

| | | | | | |
|---|---|---|---|---|---|
| SEQ_ID_NO_1274 | LREAAEIMAP | LISQALQDEK | QHRA-DTLLA | DQ-TEGRGTF | 141 |
| SEQ_ID_NO_1275 | LQKANEWMRP | LVDEVLRNES | ALEE----K | PAKPGAPGAF | 255 |
| SEQ_ID_NO_1276 | TVKAAELLKP | LINQCIQRFK | EGKGIGGESG | DEFDDDDQGTF | 272 |
| SEQ_ID_NO_1277 | KSKVAKLLRP | IIEECMRKFK | EEKTADKESS | DGFDDNQGSF | 271 |
| SEQ_ID_NO_1278 | LRTAKRIISP | MVRQRRAEEA | KRN------ | -PDYVKPNDL | 347 |
| SEQ_ID_NO_1279 | LRTAKRIISP | MVRQRRAEEA | KI------G | DPTYEKPNDL | 291 |
| SEQ_ID_NO_1274 | ISWLLRHLPE | ELR-TPEQVG | LDQMLVSFAA | IHTTMALTK | 180 |
| SEQ_ID_NO_1275 | VSWMMKHTAP | QKK-TSENMG | TNQMLLSFAA | IHTTSSTATF | 294 |
| SEQ_ID_NO_1276 | VSWMKHTSP | ELRENPYSLA | INQLTLSFAS | IHTTMAVCH | 312 |
| SEQ_ID_NO_1277 | ISWLLKWTDE | KSREDPFALA | DTQLMLSFAA | IHTTSMALSH | 311 |
| SEQ_ID_NO_1278 | LQWMMDGANE | NDG-QPDKLA | HRQLLLSLAS | IHTTMAAAH | 386 |
| SEQ_ID_NO_1279 | LQWMMDGANE | NDG-QPDKLA | HRQLLLSLAS | IHTTMAAAH | 330 |
| SEQ_ID_NO_1274 | VVWELVKRPE | YIEPLRTEMQ | DVFGPDAVSP | DL----ICLNK | 216 |
| SEQ_ID_NO_1275 | ALYDLLSRPE | YIGPLREEIE | QVIAQDGAEK | DEDGQMFLSK | 334 |
| SEQ_ID_NO_1276 | LFDLASHPE | FIAPLREEIE | QVIAEDGFEV | DGSGKKCLKK | 352 |
| SEQ_ID_NO_1277 | ILYDIASHPE | FIEPLREEIE | QVIAEDGDEI | DGSGSTNLKK | 351 |
| SEQ_ID_NO_1278 | CFYDLCQHPE | YFEPLREEIN | DVIAQDGG- | -------WKK | 417 |
| SEQ_ID_NO_1279 | CFYDLCQHPE | YFEPLREEIN | DVIAQDGG- | -------WKK | 361 |
| SEQ_ID_NO_1274 | EALSRLHKLD | SFIREVQRWC | PSTFVTPSRR | VMKSMTLSNG | 256 |
| SEQ_ID_NO_1275 | VSLSKLKKLD | SFIKESQRMN | PLNFGGTSRR | LQKDQTESNG | 374 |
| SEQ_ID_NO_1276 | QSMAKLKKLD | SLKESQRVN | PPGIANSRI | TTAPLHLSTG | 392 |
| SEQ_ID_NO_1277 | QSEAKLKKLD | SFMKESQRFS | PPALVTNFRR | TTSTLHLSTG | 391 |
| SEQ_ID_NO_1278 | TTLNKMRKLD | SFLKESQRIN | PPSLLAFNRI | VSEDLTLSDG | 457 |
| SEQ_ID_NO_1279 | TTLNKMRKLD | SFLKESQRIN | PPSLLAFNRI | VSEDLTLSDG | 401 |

Figure 9C

| | | | | | |
|---|---|---|---|---|---|
| SEQ_ID_NO_1274 | IKLQRGTSIA | FPAHAHMSE | ETPTFSPLDF | SSDFENPSPR | 295 |
| SEQ_ID_NO_1275 | LKLPAGTPIS | FPLWGVYNSS | STNTFSD-AY | NEGTGNAPPT | 413 |
| SEQ_ID_NO_1276 | HTIPKGTRIG | YDAQVLNTAG | PNLSLLPHDP | STMPQLDPPS | 432 |
| SEQ_ID_NO_1277 | HTIPKGTRIC | YDTVSNMSN | PDLSSIPHDP | SNVTSLDPPT | 431 |
| SEQ_ID_NO_1278 | TLLPKGTHFS | MPSAAILQDN | GV-------- | ----EPGAD | 484 |
| SEQ_ID_NO_1279 | TLLPKGTHFS | MPSAAILQDN | AV-------- | ----EPDAD | 428 |

| | | | | | |
|---|---|---|---|---|---|
| SEQ_ID_NO_1274 | IFDGFRYLNL | RSIKGQGSQH | QAATTGPDYL | LFNHGKHACP | 335 |
| SEQ_ID_NO_1275 | EFDGFRFARL | REQPGRETKH | QAATTGPDAF | NFGHGPHACP | 453 |
| SEQ_ID_NO_1276 | VFSPFRFASI | RETPGNESKY | QFVTTSKEAM | NFGHGNHACP | 472 |
| SEQ_ID_NO_1277 | TFSPFRWSSL | RDTPGNESKF | QFVTTSKQSM | NFGHGNHACP | 471 |
| SEQ_ID_NO_1278 | QFDGFRYYKK | RLNPEEANKH | QFAMTDNNNL | HFGHGKYSCP | 524 |
| SEQ_ID_NO_1279 | QFDAFRYYKK | RLNPEEANKH | QFAMTDNNNL | HFGHGKYSCP | 468 |

| | | | | | |
|---|---|---|---|---|---|
| SEQ_ID_NO_1274 | GRFFAISEIK | MILIELLAKY | DFRLE----- | DGKPGPELMR | 370 |
| SEQ_ID_NO_1275 | GRFFAVYVIK | QIEIEFLLNY | DRLKGSGGK | DAGSRPPNT- | 493 |
| SEQ_ID_NO_1276 | GRFFAGVEIK | VILIELLRGW | DFRNVGDTEM | KGGGRPENFC | 512 |
| SEQ_ID_NO_1277 | GRFFAGLELK | VAIVELLRNW | EFRLVGDEGA | KGGERPKNLV | 511 |
| SEQ_ID_NO_1278 | GRFFASNEIK | IIMAHLLTDY | EFKYP----- | RGATRPRNLT | 559 |
| SEQ_ID_NO_1279 | GRFFASNEIK | IIMAHLLTDY | EFKYP----- | PGASRPRNLT | 503 |

| | | | | | |
|---|---|---|---|---|---|
| SEQ_ID_NO_1274 | VGTETRLDTK | AGLEMRRR-- | ---------- | -------A-- | 388 |
| SEQ_ID_NO_1275 | RKMIVMPDFG | REVEVRKRTG | ---------- | -------V-- | 514 |
| SEQ_ID_NO_1276 | VDTAINPNPV | AEIEFKRR-- | ---------- | ---------- | 531 |
| SEQ_ID_NO_1277 | YDVTIMPDPV | GQLEFRRRK- | ---------- | -------F-- | 531 |
| SEQ_ID_NO_1278 | ADENLYPDPS | ARLLMRRRVV | APPQASTPQ | LVSA | 593 |
| SEQ_ID_NO_1279 | ADENLYPDPS | ARLLMRRRMV | AEGQAQTPE | IVLV | 537 |

Figure 9D

TRANSGENIC PLANTS HAVING ALTERED BIOMASS COMPOSITION

CROSS-REFERENCE TO RELATED APPLICATIONS

This application is a divisional of U.S. application Ser. No. 16/406,702, filed May 8, 2019 (pending), which application is a divisional of U.S. application Ser. No. 14/363,151, filed Jun. 5, 2014 (now U.S. Pat. No. 10,323,256), which application is a National Stage Entry of PCT/US2012/068756, filed Dec. 10, 2012, which application claims priority to U.S. Application Ser. No. 61/568,747, filed on Dec. 9, 2011, the disclosures each of which is incorporated herein by reference.

TECHNICAL FIELD

This document relates to methods and materials involved in modulating biomass composition in plants. For example, this document provides plants having altered sugar content or conversion efficiency, as well as materials and methods for making plants and plant products having altered sugar content or conversion efficiency.

INCORPORATION-BY-REFERENCE OF SEQUENCE LISTING

The accompanying file, named 116960300WO1SEQLISTING is 2.82 MB. The file can be accessed using Microsoft Word on a computer that uses Windows OS.

BACKGROUND

Plants store energy from sunlight in the form of chemical bonds that compose plants. The energy stored in plant materials can be converted to forms of energy such as heat, electricity and liquid fuels, depending upon the plant material employed and the process applied to extract energy from it. Other processes can produce chemical intermediates from plant biomass that are useful in a variety of industrial processes, for instance lactic acid, succinic acid, etc.

Plant materials have been used for millennia by humans to generate heat by direct combustion in air. For building and process heating purposes, this heat is typically used to generate steam, which is a more transportable heat source used to heat buildings and public areas using heat exchangers of various design. The production of steam may also be used to drive turbines, which transform heat energy into electrical energy. These processes typically involve a simple, direct combustion process of the plant material alone, or a co-firing process with coal or other energy source.

Fuels such as ethanol can be produced from plant materials by a number of different processes. For example, the sucrose in sugarcane can be extracted from the plant material and directly fermented to ethanol using a microorganism, such as brewer's yeast. Brazil has converted a significant portion of its transportation sector over to ethanol derived from sugarcane, proving this can be done on a very large scale over broad geography. As another example, the starch from corn can be processed using α-amylase and glucoamylase to liberate free glucose that is subsequently fermented to ethanol. The US uses a significant portion of its corn crop to produce ethanol from starch. While these advances are significant, the ability to increase the amount of liquid transportation fuel obtained from plant material is limited because only a small fraction of the solar energy captured and transformed into chemical energy in plants is converted into biofuels in these industrial processes.

Plant material can be used for the production of cellulosic biofuels by biochemical processes employing enzymes and/or microorganisms or by thermochemical processes such as Biomass to Liquids (BtL) technology using high temperature and non-enzymatic catalysts. There are also examples of hybrid thermochemical/biochemical processes. Biochemical processes typically employ physical and chemical pretreatments, enzymes, and microorganisms to deconstruct the lignocellulose matrix of biomass in order to liberate the fermentable from cellulose, hemicellulose, and other cell wall carbohydrates, which are subsequently fermented to ethanol by a microorganism. Currently, many different processing methods are being developed for biofuel production that employ different strategies for pretreatment, enzyme cocktails, and microorganisms. Many of these processes are focused on the production of ethanol, but butanol and other useful molecules (e.g., lactic acid, succinic acid, polyalkanoates, etc.) can also be produced in this type of process. The conversion product molecule produced is usually defined by the microorganisms selected for fermentation.

Thermochemical processes employ very high temperatures in a low oxygen (i.e., $O_2$) environment to completely degrade the organic constituents of biomass to syngas, largely composed of molecular hydrogen ($H_2$) and carbon monoxide (CO) gas. These simple molecules are then re-formed into more useful and valuable molecules (fuels or chemical intermediates) utilizing a Fischer-Tropsch process or other methods usually employing a chemical catalyst of some sort. These processes are effective at producing biofuels that are similar to current petrochemical-based hydrocarbon fuels (i.e., gasoline, diesel, jet fuel), although other biofuel molecules can also be produced in these types of processes (i.e., ethanol, butanol, kerosene).

A variant form of thermochemical process uses pyrolysis (i.e., thermal degradation in the complete absence of oxygen) to partially degrade the organic constituents present in plant biomass to a chemically heterogeneous liquid bio-oil. This serves to increase the energy density of the biomass to facilitate transport to centralized processing facilities where the bio-oil is further processed to a desired product slate.

The economic viability of biomass conversion processes is significantly impacted by the composition of the plant material and its conversion efficiency to heat, electricity, biofuels or chemical intermediates under specific processing conditions. For biochemical processes producing biofuels or other chemicals, the recalcitrance of the lignocellulose matrix of the biomass is a major factor in conversion efficiency.

SUMMARY

The present invention relates to methods of altering biomass composition in plants. Plants having altered biomass composition are useful for agriculture, forage, horticulture, biomass to energy conversion, paper production, plant product production, and other industries. For example, this document features dedicated energy crops such as *Panicum virgatum* L. (switchgrass), *Miscanthus* sp., e.g. *Miscanthus* x *gigantus* (*Miscanthus*), *Sorghum* sp., *Saccharum* sp. (sugar cane), or *Arundo donax* having altered biomass composition.

Thus, in one aspect, this document features a sorghum, *Miscanthus*, *Panicum*, or sugarcane plant cell comprising an exogenous nucleic acid. The exogenous nucleic acid comprises a regulatory region operably linked to a nucleotide sequence encoding a polypeptide, wherein the HMM bit score of the amino acid sequence of the polypeptide is greater than about 65, based on the amino acid sequences depicted in one of FIG. 1, 2, 4, 6, 7, 8, or 9. Furthermore, a plant produced from the plant cell has a difference in biomass composition as compared to the corresponding composition of a control plant that does not comprise the nucleic acid. In another aspect, the exogenous nucleic acid in the sorghum, *Miscanthus, Panicum*, or sugarcane plant comprises a regulatory region operably linked to a nucleotide sequence encoding a polypeptide having 80 percent or greater sequence identity to an amino acid sequence selected from the group consisting of SEQ ID NO: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567. A plant produced from such a plant cell has a difference in biomass composition as compared to the corresponding composition of a control plant that does not comprise the nucleic acid. The difference in biomass composition in the plant can be an increase in the total sugar content, an increase in sugar availability from the cell wall, increase in total glucose released from pretreatment, an increase in total sugar content in juice, increased juice brix, increase in yield of juice, increase in sucrose purity in juice, increase in sugar yield in juice from the plant, a decrease in ash content, and/or an increase in total glucan content. The difference in biomass composition in the plant can be at least a 1.5 fold, 2.0 fold, or 2.5 fold increase in glucose from cell well as compared to that of a control plant that does not comprise the nucleic acid. The difference in biomass composition in the plant can be at least a 3 fold, 4 fold, or 6 fold increase in sugar yield as compared to that of a control plant that does not comprise the nucleic acid. The difference in biomass composition in the plant can be an increase in conversion efficiency as compared to that of a control plant that does not comprise said nucleic acid. This document also features methods of producing such sorghum, switchgrass, sugarcane or *Miscanthus* plants. The plant or plant cell can also contain a second exogenous nucleic acid that comprises a regulatory region operably linked to a sequence of interest.

The polypeptide can comprise a 2OG-Fe(II) oxygenase superfamily domain having 60 percent or greater sequence identity to residues 211-309 of SEQ ID NO: 471 or to residues 209-306 of SEQ ID NO:1. In some embodiments, the polypeptide comprises an alpha/beta hydrolase fold domain having 60 percent or greater sequence identity to residues 116-329 of SEQ ID NO: 99 and a carboxylesterase family domain having 60 percent or greater sequence identity to residues 110-210 of SEQ ID NO: 99. Such polypeptides include GA 20-oxidases. The polypeptide can comprise a cytochrome P450 domain having 60 percent or greater sequence identity to residues 142-500 of SEQ ID NO:1429, to residues 176-504 of SEQ ID NO:1386, or to residues 98-368 of SEQ ID NO:1274.

In another aspect, this document features a plant cell comprising an exogenous nucleic acid. The exogenous nucleic acid encodes a transcription product that inhibits expression of a polypeptide having 80 percent or greater sequence identity to an amino acid sequence selected from the group consisting of SEQ ID NO: 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1009, 1010, 1011, 1012, 1013, 1014, 1015, 1016, 1017, 1018, 1019, 1020, 1021, 1022, 1023, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273.

This document also features a plant cell that include an exogenous nucleic acid encoding a transcription product that inhibits expression of a polypeptide, wherein the HMM bit score of the amino acid sequence of the polypeptide is greater than about 65, the HMM based on the amino acid sequences depicted in one of FIGS. 1, 2, 4, 6, 7, 8, and 9.

A plant produced from the plant cell has a difference in biomass composition as compared to the corresponding composition of a control plant that does not comprise the nucleic acid. The transcription product can be an interfering RNA. The difference in biomass composition in the plant can be an increase in the total sugar content, an increase in sugar availability from the cell wall, increase in total glucose released from pretreatment, an increase in total sugar content in juice, increased juice brix, increase in yield of juice, increase in sucrose purity in juice, and/or increase in sugar yield in juice from the plant. The difference in biomass composition in the plant also can be selected from the group consisting of a decrease in ash content and an increase in the total glucan content.

This document features a method of producing biomass. Such a method comprises growing a plurality of the transgenic plants described herein; and harvesting biomass from the plants. The plurality of plants can be sorghum plants and the harvesting step can comprise harvesting stalks from the plants. The method can further comprise pretreating the harvested biomass. The method can further comprise the step of enzymatically processing the harvested biomass.

This document also features a method of processing biomass. Such a method comprises extracting sugars from biomass from a plurality of transgenic plants described herein. The method can further include the step of crystallizing the sugars (e.g., sucrose).

This document also features a method of altering biomass composition in sorghum, *Miscanthus, Panicum*, or sugarcane. Such a method comprises modifying an endogenous biomass composition-modulating nucleic acid in a sorghum, *Miscanthus, Panicum*, or sugarcane plant. The nucleic acid comprises a nucleotide sequence with an open reading frame having 80 percent or greater sequence identity to the nucleotide sequence selected from the group consisting of SEQ ID NO: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

This document also features methods of altering biomass composition in *Miscanthus* that comprise inhibiting an endogenous biomass composition-modulating nucleic acid in a *Miscanthus* plant. In such methods, an RNAi sequence may comprise a sequence having 80 percent or greater sequence identity to the nucleotide sequence selected from the group consisting of SEQ ID NO: 1568, 1569, 1570, 1571, 1572, 1573, 1574, 1575, 1576, 1577, 1578, 1579, and 1580, or a fragment thereof.

The plant has a difference in biomass composition as compared to the corresponding composition of a control plant in which the nucleic acid has not been modified. The difference in biomass composition in the plant can be an increase in total sugar content, an increase in sucrose content, a decrease in ash content or an increase in total glucan content. The modification can be effected by introducing a genetic modification in the locus comprising the nucleic acid. The method can further include selecting for plants having altered biomass composition.

This document also features a sorghum, *Miscanthus, Panicum*, or sugarcane plant cell containing a modified endogenous nucleic acid encoding a polypeptide. The HMM bit score of the amino acid sequence of the polypeptide is greater than about 65, with the HMM based on the amino acid sequences depicted in one of FIGS. 1-9. A plant produced from the plant cell has a difference in biomass composition as compared to the corresponding composition of a control plant where the nucleic acid has not been modified. The difference in biomass composition in the plant can be an increase in total sugar content, an increase in sucrose content, a decrease in ash content or an increase in total glucan content. This document also features a method of producing such sorghum, *Miscanthus, Panicum*, or sugarcane plants.

This document also features a sorghum, *Miscanthus, Panicum*, or sugarcane plant cell containing a modified biomass composition-modulating endogenous nucleic acid. The endogenous nucleic acid comprises a nucleotide sequence with an open reading frame having 80 percent or greater sequence identity to the nucleotide sequence selected from the group consisting of SEQ ID NO: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

This document also features a *Miscanthus* plant cell containing a modified biomass composition-modulating endogenous nucleic acid. In such methods, an RNAi sequence may comprise a sequence having 80 percent or greater sequence identity to the nucleotide sequence selected from the group consisting of SEQ ID NO: 1568, 1569, 1570, 1571, 1572, 1573, 1574, 1575, 1576, 1577, 1578, 1579, and 1580, or a fragment thereof.

A plant produced from such a sorghum, *Miscanthus, Panicum*, or sugarcane plant cell has a difference in biomass composition as compared to the corresponding composition of a control plant where the nucleic acid has not been modified. The difference in biomass composition in the plant can be an increase in total sugar content, an increase in sucrose content, a decrease in ash content or an increase in total glucan content.

In another aspect, this document features a method of modulating biomass composition of a plant. Such a method comprises introducing into a sorghum, *Miscanthus, Panicum*, or sugarcane plant an exogenous nucleic acid. The exogenous nucleic acid encodes or affects a polypeptide in the gibberellin (GA) biosynthesis or signaling pathway so as to increase levels of, or sensitivity to, active gibberellins. The plant has a difference in biomass composition as compared to the corresponding composition of a control plant that does not comprise the exogenous nucleic acid. The difference in biomass composition in the plant can be an increase in total sugar content, an increase in sucrose content, a decrease in ash content or an increase in total glucan content.

In another aspect, this document features a method of modulating biomass composition of a plant. Such a method comprises introducing into a plant first and second exogenous nucleic acids. The first exogenous nucleic acid encodes or affects a polypeptide in the GA biosynthesis or signaling pathway so as to increase levels of, or sensitivity to, active gibberellins and the second exogenous nucleic acid encodes a sequence of interest. The plant has a difference in biomass composition as compared to the corresponding composition of a control plant that does not comprise the exogenous nucleic acids. The difference in biomass composition in the plant can be an increase in total sugar content, an increase in sucrose content, a decrease in ash content or an increase in total glucan content.

This document also features a sorghum, *Miscanthus, Panicum*, or sugarcane plant cell or plant comprising an exogenous nucleic acid. The exogenous nucleic acid encodes or affects a polypeptide in the GA biosynthesis or signaling pathway so as to increase levels of, or sensitivity to, active gibberellins. The plant has a difference in biomass composition as compared to the corresponding level of a control plant that does not comprise the exogenous nucleic acid. The difference in biomass composition in the plant can be an increase in total sugar content, an increase in sucrose content, a decrease in ash content or an increase in total glucan content.

This document also features a sorghum plant containing an exogenous biomass composition-modulating nucleic acid. The plant has an increase in total sugar content in juice, increase in juice brix, and/or increase in yield of sugar from juice from the plant that is statistically significantly greater than that of a corresponding control plant that lacks the biomass composition-modulating nucleic acid. The plant can have a sucrose content that is statistically significantly greater than the sucrose content of a corresponding control plant that lacks the biomass composition-modulating nucleic acid.

This document also features a sorghum, *Panicum, Miscanthus*, or sugarcane plant containing an exogenous biomass composition-modulating nucleic acid. The plant has a biomass composition that is statistically significantly different from the biomass composition of a corresponding control plant that lacks the biomass composition-modulating nucleic acid. Biomass from the plant can have an increase in the total sugar content, an increase in sugar availability from the cell wall, increase in total glucose released from pretreatment, an increase in total sugar content in juice, increase in juice brix, increase in yield of juice, increase in sucrose purity in juice, and/or increase in sugar yield in juice from the plant relative to a corresponding control plant that lacks the biomass composition-modulating nucleic acid.

In another aspect, this document features a method of producing biomass, comprising applying a gibberellin (e.g., GA3) to a population of plants (e.g., sorghum, *Panicum, Miscanthus*, sugarcane, or *Arundo donax*), and harvesting cellulosic biomass from the plants.

This document also features a method of processing biomass. The method includes pretreating biomass harvested from a plurality of plants (e.g., sorghum, switchgrass, *Miscanthus*, sugarcane, or *Arundo donax* plants) to which a gibberellin has been applied; and extracting sugars from the pretreated biomass. The pretreating step can include a physical or chemical pretreatment of biomass harvested from plants to which a gibberellin has been applied a plurality of times. The method further can include the step of saccharifying the pretreated biomass before extracting cell wall-associated sugars. The total amount of sugar extracted from the biomass can be statistically significantly increased compared to that of biomass from corresponding control plants to which a gibberellin has not been applied.

In another aspect, this document features a method of processing biomass, comprising pretreating biomass harvested from a plurality of plants to which a gibberellin has been applied, fermenting the biomass and producing a fuel from the fermented biomass. The pretreating step can be a physical or chemical treatment of the harvested biomass. The method can further comprise the step of saccharifying the pretreated biomass before fermenting. The saccharifying step can comprise saccharifying biomass harvested from plants to which a gibberellin has been applied a plurality of times. The pretreating step releases a significant increase in cell wall associated sugars compared to pretreating biomass from corresponding control plants to which a gibberellin has not been applied. The biomass can have an increased yield of fuel compared to biomass from corresponding control plants to which a gibberellin has not been applied. The plants can be transgenic switchgrass, sorghum, sugarcane, or *Miscanthus* plants as described herein. The plants can be sugarcane plants. The gibberellin can be GA3.

In another aspect, this document features a method of processing biomass, comprising pyrolysing biomass harvested from a plurality of plants to which a gibberellin has been applied and producing a fuel from the pyrolysed biomass.

This document also features a method of processing biomass, comprising gasifying biomass harvested from a plurality of plants to which a gibberellin has been applied, and producing a fuel from the gasified biomass. The biomass can have a decreased ash content compared to biomass from corresponding control plants to which a gibberellin has not been applied.

This document also features a method of processing biomass, comprising pyrolysing biomass harvested from a plurality of transgenic plants described herein, and producing a fuel from the pyrolysed biomass.

This document also features a method of processing biomass, comprising gasifying biomass harvested from a plurality of transgenic plants described herein, and producing a fuel from the gasified biomass. The biomass can have a decreased ash content compared to biomass from corresponding control plants that lack the exogenous nucleic acid. The biomass can be harvested from plants to which a gibberellin has been applied.

This document also features a method of producing a forage product that includes growing a plurality of the plants described herein; harvesting biomass from the plants; chopping or cutting the harvested biomass; and ensiling the chopped or cut biomass to produce the forage product.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIGS. 1A-1K contain an alignment of the amino acid sequence of GI_115456701 (SEQ ID NO: 471) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes.

FIG. 1 and the other alignment figures provided herein were generated using the program MUSCLE version 3.52.

FIGS. 2A-2E contain an alignment of the amino acid sequence of GI_75324272 (SEQ ID NO: 99) with homologous and/or orthologous amino acid sequences.

Figure 3B:
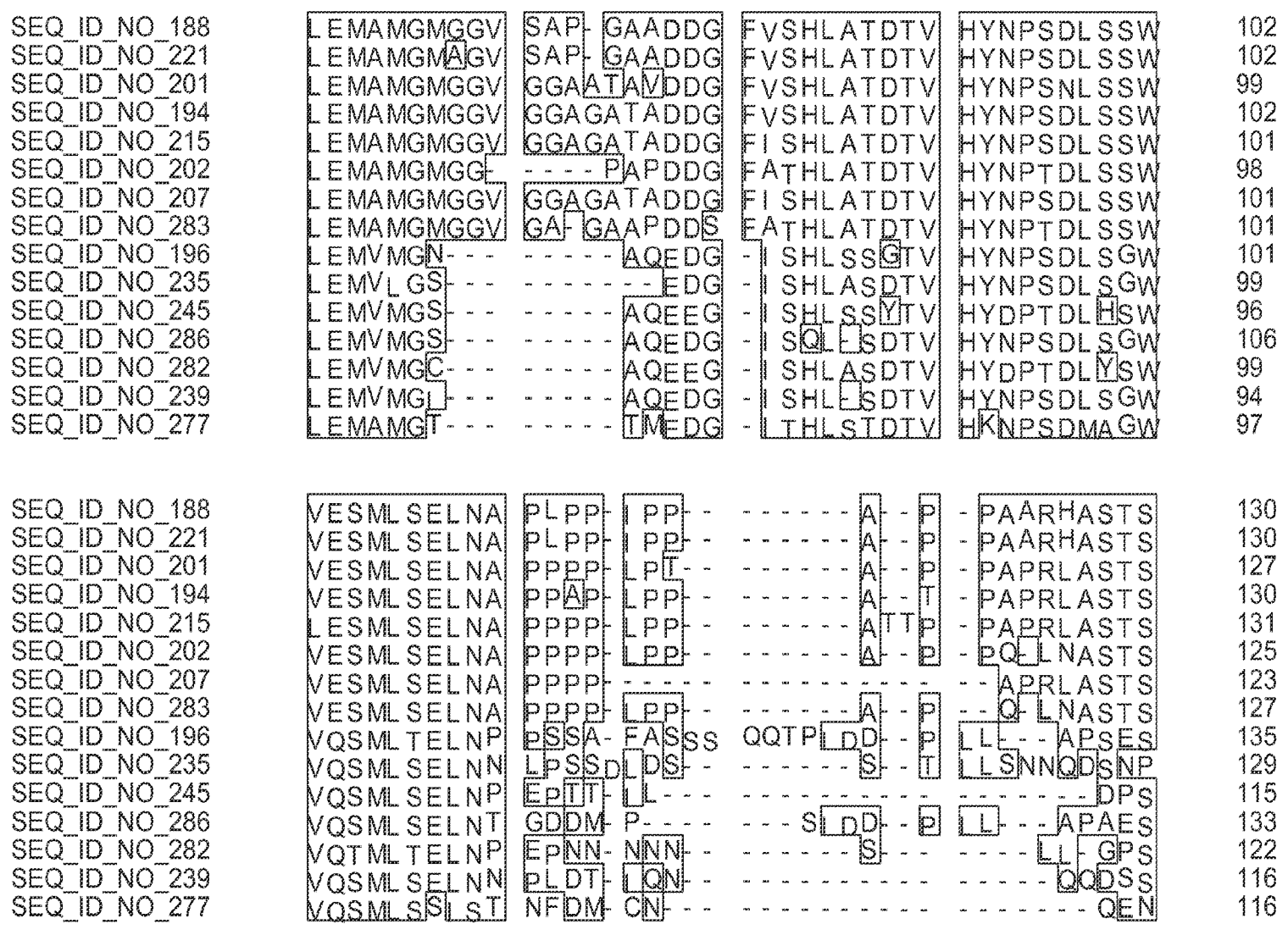
Figure 3I:
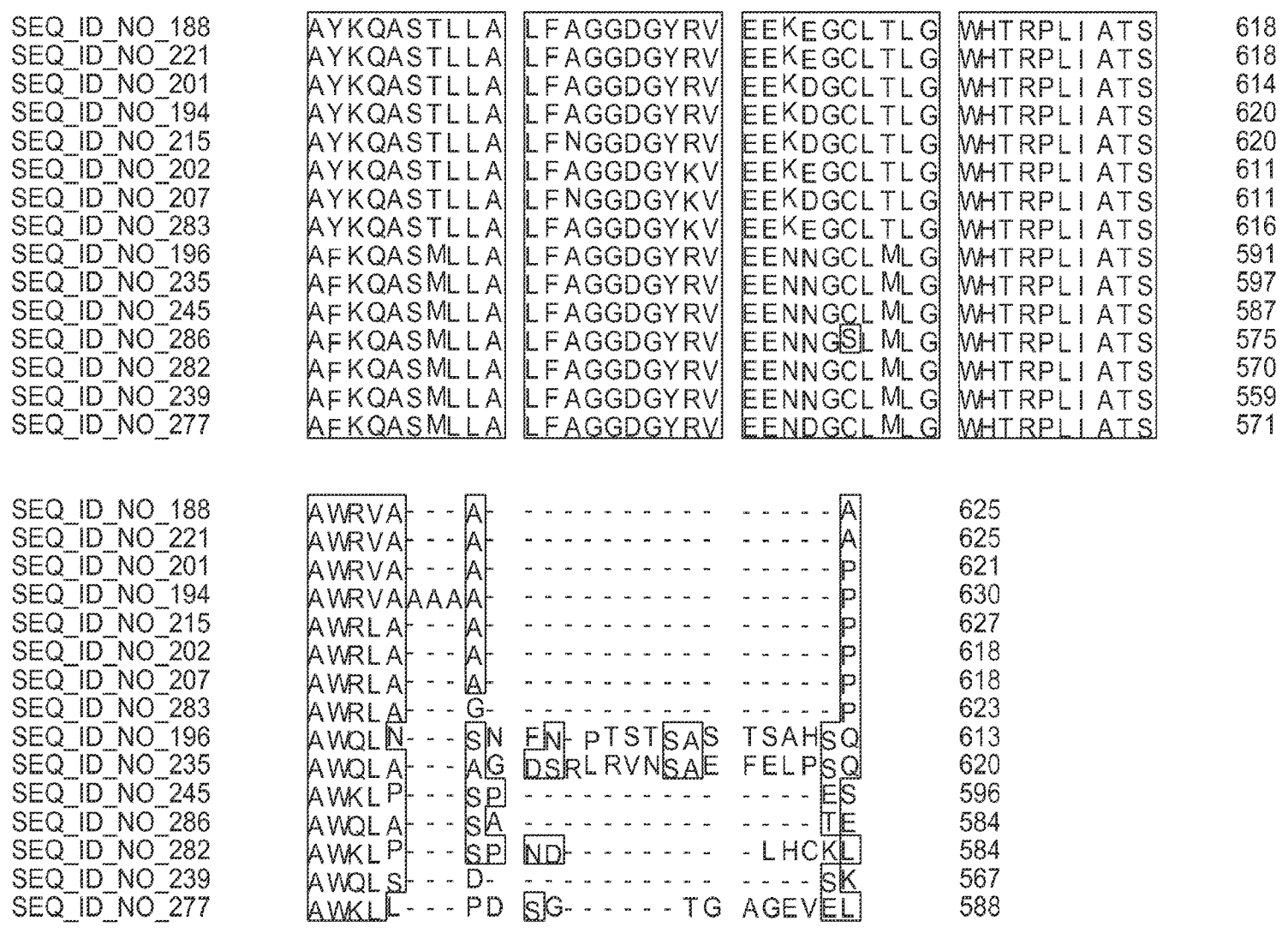

FIGS. 3A-3T contain an alignment of the amino acid sequence of GI_75139772 (SEQ ID NO: 188) with homologous and/or orthologous amino acid sequences.

Figure 4C:
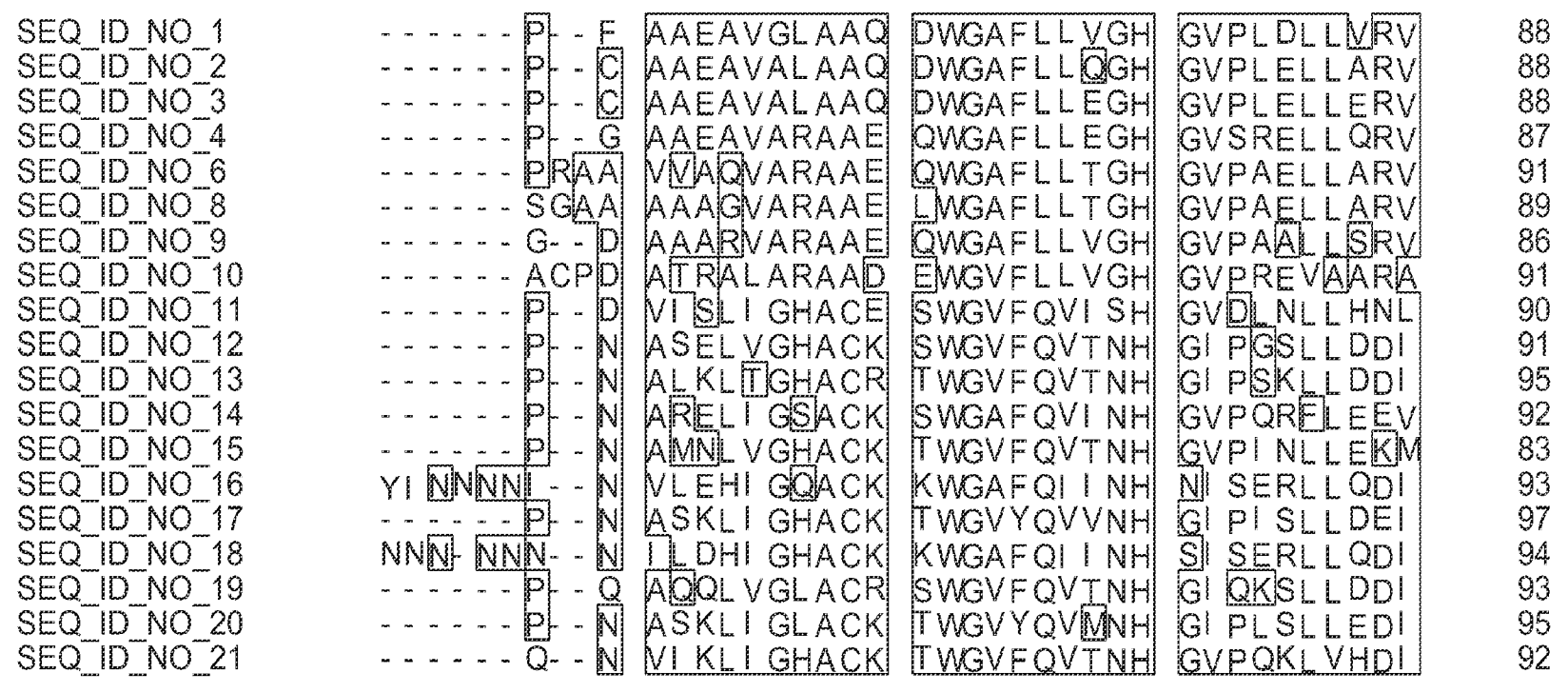

FIGS. 4A-4L contain an alignment of the amino acid sequence of GI_85540948 (SEQ ID NO:1) with homologous and/or orthologous amino acid sequences.

FIGS. 5A-5J contain an alignment of the amino acid sequence of G2OX1_ARATH (SEQ ID NO: 287) with homologous and/or orthologous amino acid sequences.

FIGS. 6A-6H contain an alignment of the amino acid sequence of Cytochrome P450 CYP68B1 GiGA20-oxidase (SEQ ID NO: 1429) with homologous and/or orthologous amino acid sequences.

FIGS. 7A-7B contain an alignment of the amino acid sequence of GA4 desaturase (SEQ ID NO: 1542) with homologous and/or orthologous amino acid sequences.

FIGS. 8A-8B contain an alignment of the amino acid sequence of Cytochrome P450 GA14-synthase (SEQ ID NO: 1386) with homologous and/or orthologous amino acid sequences.

FIGS. 9A-9D contain an alignment of the amino acid sequence of Cytochrome P450 CYP69A1 C13-oxidase (SEQ ID NO: 1274) with homologous and/or orthologous amino acid sequences.

DETAILED DESCRIPTION

Figure 4K:
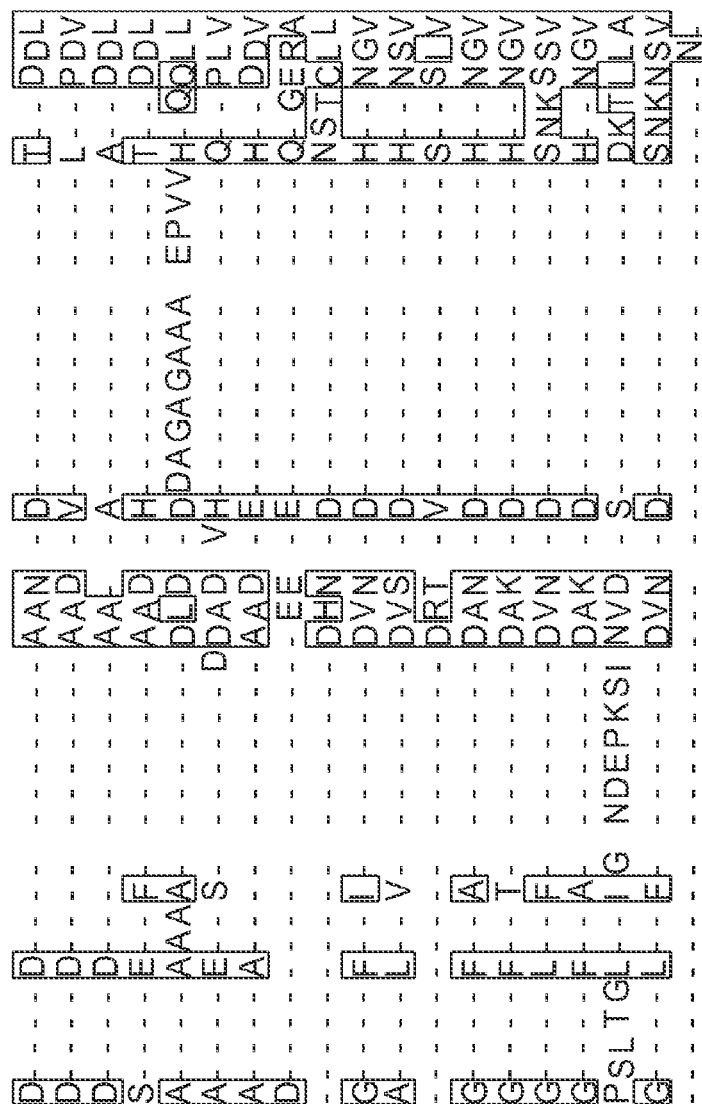

This document features methods and materials related to modulating biomass composition (e.g., one or more of total sugar content, sucrose content, ash content and total glucan content, an increase in sugar availability from the cell wall, increase in total glucose released from pretreatment, an increase in total sugar content in juice, increase in juice brix, increase in yield of juice, increase in sucrose purity in juice, increase in sugar yield in juice from the plant, or increase in conversion efficiency) in plants. For example, this document features methods and materials for increasing or decreasing total sugar content, ash content and/or total glucan content in plants. In some embodiments, a plant can have one or more of increased total sugar content, increased sucrose content, an increase in sugar availability from the cell wall, increase in total glucose released from pretreatment, an increase in total sugar content in juice, increase in juice brix, increase in yield of juice, increase in sucrose purity in juice, increase in sugar yield in juice from the plant, increased conversion efficiency, decreased ash content, and increased total glucan content. In some embodiments, the plants also may have modulated levels of, for example, lignin, modified root architecture, modified herbicide resistance, or modified carotenoid biosynthesis. The methods can include, for example, (i) transforming a plant cell with a nucleic acid encoding a biomass composition-modulating polypeptide, wherein expression of the polypeptide results in modulated biomass composition or (ii) transforming a plant cell with a nucleic acid encoding a transcription product that inhibits expression of a biomass composition-modulating polypeptide, wherein decreased expression of the polypeptide results in modulated biomass composition. Plant cells produced using such methods can be grown to produce plants having an increased or decreased sugar content and/or conversion efficiency. Such plants may produce more grazable forage. Increased brix levels and/or sugar content can result in increased palatability as a forage crop. Biomass harvested from such plants can be cut or chopped and ensiled, with or without additives, to produce a forage product. In addition, such plants, and the seeds of such plants, may be used to produce, for example, switchgrass, *Miscanthus, Sorghum* sp., and sugar cane plants having increased value as a biofuel feedstock.

I. Definitions

"Accessible Carbohydrate" refers to mono- and oligo-saccharides released into the aqueous phase after processing of a biomass feedstock. The amount of accessible carbohydrate in a feedstock is related to the pretreatment and enzymatic saccharification conditions chosen for the saccharification process and to the composition and structure of the initial biomass feedstock.

"Amino acid" refers to one of the twenty biologically occurring amino acids and to synthetic amino acids, including D/L optical isomers.

"Ash" refers to inorganic material that contributes to the dry weight of the feedstock. Ash content in biomass feedstocks can be determined using published, standard methods such as ASTM Standard E1755.

"Biochemical processing" refers to a primarily biological process where plant materials are converted to liquid products using enzymes and/or fermentation organisms. Biochemical processing may require thermochemical pretreatments.

"Biofuels" include, but are not limited to, biodiesel, methanol, ethanol, butanol, linear alkanes ($C_5$-$C_{20}$), branched-chain alkanes ($C_5$-$C_{26}$), mixed alkanes, linear alcohols ($C_1$-$C_{20}$), branched-chain alcohols ($C_1$-$C_{26}$), linear carboxylic acids ($C_2$-$C_{20}$), and branched-chain carboxylic acids ($C_2$-$C_{26}$). In addition, ethers, esters and amides of the aforementioned acids and alcohols, as well as other conjugates of these chemicals may be of interest. Many of these chemicals can be subsequently converted by chemical reactions to other high value, high volume chemicals.

"Biomass" refers to organic matter. Biomass includes plant matter derived from herbaceous and woody energy crops, agricultural food and feed crops, agricultural crop wastes and residues, wood wastes and residues, aquatic plants, and other plant-derived materials. Biomass may also include algae, yard wastes, and include some municipal wastes. Biomass is a heterogeneous and chemically complex renewable resource. Components of biomass include glucan, xylan, fermentable sugars, arabinan, sucrose, lignin, protein, ash, extractives, ferulate, and acetate.

In some embodiments, biomass primarily encompasses above ground plant parts. In some embodiments, biomass primarily encompasses stem plant parts. In some embodiments, biomass primarily encompasses those above ground plant parts other than inflorescence and seed parts of a plant. Biomass can be quantified as dry matter yield, which is the mass of biomass produced (usually reported in Tons/acre) if the contribution of water is subtracted from the fresh mater weight. Dry matter yield (DMY) yield is calculated using the fresh matter weight (FMW) and a measurement of weight percent moisture (M) in the following equation: DMY= (100−M)/100)*FMW. Biomass can be quantified as fresh matter yield, which is the mass of biomass produced (usually reported in Tons/acre) on an as-received basis, which includes the weight of moisture. Biomass can sometimes be quantified as juice yield, e.g., the volume of juice separated from bagasse or sorghum or sugarcane stalks, which can be reported per unit area.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Conversion efficiency" refers to the percentage of biomass feedstock converted to product relative to one or more inputs. The product can be energy, automotive fuel, jet fuel, free sugars, fermentable sugars, syngas, ethanol, heat, electricity, or energy, and the input can a parameter such as the amount of biomass, total carbohydrate, amount and type of saccharification enzyme(s), or accessible carbohydrate. The concept of conversion efficiency describes the yield of energy (in terms of biofuel, heat, and/or electricity) derived from a biomass starting material subjected to a particular process as compared to a theoretical yield of energy stored in the biomass starting material. The efficiency by which biomass can be converted into energy via these processes is dependent upon a number of compositional characteristics of the biomass. The relevant compositional characteristics differ based on the conversion process design.

Generally, the conversion efficiency of biochemical processes is most influenced by the concentration of carbohydrate in the biomass and the ease with which that carbohydrate can be hydrolyzed to fermentable sugars. In biochemical processing the lignin in the feedstock is typically converted to energy by burning to generate heat and electricity. Similarly, the efficiency and yield of thermochemical processes for the production of biofuels are most influenced by the overall amounts of carbon to hydrogen to oxygen (C:H:O weight percents) and ash content of the biomass. The efficiency of thermochemical combustion processes is most influenced by the higher heating value (HHV) and ash content of the biomass. The HHV of biomass is a function of carbon, hydrogen and oxygen content of the biomass. The relevant conversion efficiency parameters are dependent on the type of conversion process employed (biochemical, thermochemical to biofuel, or thermochemical to heat and electricity).

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Glucan," "Xylan" and "Arabinan" refer to the anhydro forms of glucose, xylose and arabinose that are found in cellulose and hemicellulose carbohydrate polymers. Thus, for example, "glucan" refers to a polysaccharide of D-glucose monomers linked by glycosidic bonds. The following are glucans: cellulose (β-1,4-glucan), dextran (α-1,6-glucan) and starch (α-1,4- and α-1,6-glucan). See, Technical Report NREL/TP-510-42618, Determination of Structural Carbohydrates and Lignin in Biomass.

"Hemicellulose" is a general term used to refer to cell wall polysaccharides that are not celluloses or pectins. Hemicelluloses contain repeating monomeric units of a five-carbon sugar (usually D-xylose or L-arabinose) and/or a six-carbon sugar (D-galactose, D-glucose, and D-mannose). See, U.S. Pat. No. 7,112,429. Hemicelluloses typically are shorter in length than cellulose and are highly branched. Xylan is often the structural backbone of hemicelluloses from hardwoods and grasses, and hydrolysis of these biomass types releases products high in the five-carbon sugar, xylose. Hemicelluloses from softwoods are most commonly gluco-galacto-mannans, which have a mannan backbone and yield mannose as the main product of hydrolysis. Hemicelluloses often contain side groups such as acetyl groups, uronic acids and ferulates.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Higher heating value" (HHV) refers to the amount of heat released by a specified quantity of a fuel at an initial temperature of 25° C., following combustion, and return of the combustion products to a temperature of 25° C. The HHV is also known as the gross calorific value or gross energy.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Lignin" refers to a polyphenolic polymeric substance of plant cells, with a complex, cross-linked, highly aromatic structure. Lignin is synthesized in plants principally from three monolignol monomers, which can be methoxylated to various degrees: sinapyl alcohol ($C_{11}H_{14}O_4$) that is incorporated into lignin as (S) syringyl units; coniferyl alcohol ($C_{10}H_{12}O_3$) that is incorporated into lignin as (G) guaiacyl units; and p-coumaryl alcohol ($C_9H_{10}O_2$) that is incorporated into lignin as (H) p-hydroxyphenyl units. These monomers can be synthesized into lignin by extensive condensation polymerization. The lignin present in different plant varieties can have different syringyl:guaiacyl:p-hydroxyphenyl weight percents (S:G:H weight percents). For example, certain grass varieties can have lignin composed almost entirely of guaiacyl (G). Lignin is a major structural constituent of plant cells in woody species.

"Modulation" of the level of biomass refers to the change in the level of the biomass that is observed as a result of expression of, or transcription from, an exogenous nucleic acid in a plant cell and/or plant. The change in level is measured relative to the corresponding level in control plants.

"NOX emissions" refers to mono-nitrogen oxides (NOx), such as NO and NO2, released into the atmosphere. While oxygen and nitrogen gases do not typically react at ambient temperatures, oxygen and nitrogen gases can react at higher temperatures to create various oxides of nitrogen, including mono-nitrogen oxides. Mono-nitrogen oxides can also be produced by combusting materials including elemental nitrogen. Mono-nitrogen oxides (NOx) released into the atmosphere can react with volatile organic compounds to produce smog. Accordingly, NOX emissions may be regulated by various governmental agencies. Oxides of sulfur (SOx), specifically sulfur dioxide, are often generated in the same processes. SOx emissions are known to contribute to acid rain.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Recalcitrant carbohydrate material" refers to mono- and oligo-saccharides that are not released into the aqueous phase after processing of a biomass feedstock. It is related to the pretreatment and enzymatic saccharification conditions chosen for the saccharification process.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Saccharification" refers to the hydrolysis of carbohydrate material to the mono- and disaccharides that constitute the polymer. For example, saccharification of xylan results in the production of xylose, the monosaccharide constituent of xylan. Saccharification occurs during the biochemical processing of biomass in biorefineries, ultimately leading to the production of biofuels such as ethanol.

"Saccharification efficiency" of a feedstock sample refers to the total amount of mono and disaccharides solubilized by a pretreatment/enzymatic saccharification process, divided by the theoretical maximum amount of mono and disaccharides in the biomass sample that could have been released based on compositional analysis, converted to a percentage by multiplying by 100.

"Sustainability indicators" refer to components of biomass processing byproducts, such as the expected ash composition and soil nutrients, which may be recycled.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Methods

This document features methods and materials related to modulating biomass composition. These methods and materials are based on the surprising discovery that biomass from plants overexpressing polypeptides in the GA pathway that increase levels of active gibberellins such as GA 20-oxidases can exhibit an altered compositional profile, such that biomass from such plants provides improved efficiency and/or has increased yield when used for biofuel or energy production. For example, transgenic plants overexpressing an exogenous nucleic acid encoding a GA 20-oxidase can exhibit an increased yield of glucose after pretreatment and enzymatic saccharification, and/or equivalent yields of glucose at lower amounts of saccharification enzymes relative to the enzyme amounts required for corresponding plants that do not overexpress the nucleic acid. Such plants can also exhibit modulation in the ash content and/or total glucan content.

Thus, this document features methods of producing biomass that involve growing a plurality of plants that overexpress a transgene encoding a polypeptide in the GA pathway that increase levels of active gibberellins such as GA 20-oxidase, GA 3-oxidase, GA 2-oxidase or a GA receptor, and harvesting biomass from such plants. Alternatively, such methods can comprise growing a plurality of plants that express an exogenous nucleic acid that downregulates genes such as DELLA. Suitable exogenous nucleic acids are described in more detail below, as well as techniques for increasing expression of endogenous genes. Suitable plants include sorghum plants, *Miscanthus* plants and switchgrass plants, as described in more detail below.

In some embodiments, methods for processing biomass from plants described herein include subjecting the biomass to a pretreatment and/or subjecting the biomass to enzymatic processing. Such methods are particularly suitable when biomass is to be fermented for biofuel production or to be used for energy production.

Typically, enzymatic processing conditions are defined by the type of enzymes used and the amount of each enzyme(s) used during the saccharification process in a biorefinery. For example, an enzymatic processing condition can entail the use of a single enzyme preparation such as Spezyme® CP (Genencor, USA) or Celluclast 1.5L (Novozymes, Franklinton, N.C.). Spezyme® CP and Celluclast 1.5L are commercially available enzyme mixtures containing cellulases that are prepared by submerged culture fermentation of the filamentous fungus, *Trichoderma reesei*. These cellulase preparations are deficient in β-glucosidase activity, so they are often supplemented with a β-glucosidase preparation such as Novozyme 188, obtained by submerged culture fermentation of *Aspergillus niger*. Novozyme 188 is available from Sigma (St. Louis, Mo., USA) as catalog number C6105.

Enzyme cocktails containing a plurality of enzymes are sometimes used in biomass processing, such cocktails differing from each other in the type and amount of each enzyme. In some embodiments, an enzymatic processing condition includes the use of two types or three types of enzyme, e.g., Spezyme® CP in combination with a xylanase, or an endo-β-(1,4)-glucanase (EC 3.2.1.4), an exo-β-(1,4)-glucanase (EC 3.2.1.91) and a β-D-glucosidase (EC 3.2.1.21). See, e.g., U.S. Pat. Nos. 5,874,274; 6,333,181; 7,059,993 and U.S. Patent Publication 2007/0092935. Other enzymes include ß-1,4-cellobiohydrolases (CBH I & CBH II); xylanases (XYN I & XYN II); ß-glucosidase; α-L-arabinofuranoside; acetyl xylan esterase; ß-mannanase; and α-glucuronidase.

Biomass processing sometimes includes a physical or chemical pretreatment before enzymatic processing. A typical pretreatment is a dilute-acid thermochemical pretreatment, which partially or completely hydrolyzes the hemicellulose and can also hydrolyze some of the lignin. See, e.g., U.S. Pat. No. 6,090,595. Other types of pretreatment include sulfite pretreatment and ozone pretreatment. Thus, in some embodiments, a method described herein involves pretreating biomass prior to enzymatic processing.

Biomass processing can also include a fermentation step, which typically results in the production of fuels such as ethanol. In some cases, the enzymatic saccharification and fermentation steps are carried out simultaneously. If enzymatic saccharification and fermentation are carried out sequentially, the product of the saccharification step can be separated into an aqueous mixture containing mono- and disaccharides, and residual materials, primarily lignin. The aqueous mixture is then subjected to fermentation. Suitable organisms for use in fermentation include *Saccharomyces* spp., *Zymomonas niobilis* and *Clostridium* spp.

In other embodiments, biomass from plants described herein can be processed by thermochemical techniques to produce fuels, energy or heat. Accordingly, a method of processing biomass can involve subjecting biomass from plants described herein to heat and/or pressure under reduced oxygen conditions, which results in the formation of syngas (primarily carbon monoxide and hydrogen). The gasification step typically uses temperatures from about 800° C. to 1400° C. The syngas is then conditioned to remove particulates, light hydrocarbons such as methane, and tar. The syngas can then be used to produce fuels such as gasoline, diesel or methanol. Alternatively, a method of processing biomass can involve subjecting biomass from plants described herein to pyrolysis, i.e., heat and/or pressure in the absence of oxygen. The pyrolysis step typically uses temperatures from about 400° C. to 800° C., and results in the formation of biomass tars. The resulting tars can be then used to produce products such as olefins, oils and specialty chemicals. Saccharification can be determined and saccharification efficiency can be calculated for individual monosaccharides, e.g., glucose conversion efficiency, for combinations of monosaccharides, e.g., glucose+xylose conversion efficiency, or for all monosaccharides. The choice of mono and disaccharide(s) for which saccharification efficiency is calculated in a method is based on factors such as the type of biomass to be processed, and the capability of the conversion process to use all or just some of the sugars made available for biofuel or energy production.

In some embodiments, sugars are extracted from plants described herein for use as a food. Alternatively, sugars can be extracted from plants described herein and further processed for other industrial uses. In these cases, a method can involve the steps of extracting sugars (mono- and disaccharides) from harvested biomass and, optionally, crystallizing the extracted sugars. For example, the stalks of sorghum plants described herein can be harvested by hand or mechanical harvesters, and the juice, containing mono- and disaccharides, extracted by crushing and pressing the stalks with a horizontal or vertical mill. Mono- and disaccharide solids can be produced by crystallization from the juice, which typically involves techniques such as filtering, clarifying, decolorizing, and repeated concentration.

Methods of producing biomass and methods of processing biomass disclosed herein can also involve the use of a gibberellin to facilitate modulation of biomass composition. Gibberellins are tetracyclic diterpene acids that function as plant hormones in dormancy and other aspects of germination. Gibberellins are named GA1 . . . GAn in the order of their discovery. One of the most potent is gibberellic acid, also called GA3. Other active GAs include GA4 and GA7. Thus, a method of producing biomass can comprise applying a gibberellin to a population of plants, either transgenic plants described herein or non-transgenic sorghum, switchgrass, sugarcane or *Miscanthus* plants. The gibberellin typically is applied to foliage in the mid- to late stages of a growing season by spraying, either with a mechanical sprayer or by airplane. A single treatment of a gibberellin can be applied, but more typically, multiple applications are made during a growing season, e.g., 2, 3, 4, 5 or 6 applications. Biomass is then harvested from such plants, which has a composition that differs from that of corresponding control plants to which a gibberellin has not been applied, e.g., such biomass has an increase in total sugar content, a decrease in ash content and/or an increase in total glucan content. Biomass from gibberellin-treated plants can be processed for fuel or energy production, e.g., can be subjected to a pretreatment, and/or enzymatic processing, and/or fermentation, to produce a biofuel. In some embodiments, biomass from gibberellin-treated plants such as sorghum or sugarcane is subjected to an extraction process to obtain sugars. In some embodiments, the resulting juice is purified to obtain sucrose, e.g., crystallized sucrose.

In some aspects the invention relates to methods for breeding plants with composition characteristics that make them more valuable as dedicated food, fuel or energy feedstocks. The $F_1$ or later generation progeny are selected for those plants having desirable attributes related to biomass composition and/or conversion efficiency. Conversion efficiency may be in terms of saccharification efficiency, the conversion of biomass feedstock to free sugars, fermentable sugars, syngas, or a biofuel. The relevant conversion efficiency parameter(s) are dependent on the type of conversion process employed (biochemical, thermochemical to biofuel, or thermochemical to biopower, heat and electricity). Thus, for example, a method of breeding a plant variety comprises crossing two or more parent plants and selecting progeny of the cross that have higher saccharification efficiency relative to the saccharification efficiency of at least one of the parents, or selecting progeny of the cross that have a higher sucrose content relative to the sucrose content of at least one of the parents.

Techniques suitable for use in a plant breeding program are known in the art and include, without limitation, backcrossing, polycrossing, mass selection, pedigree breeding, bulk selection, crossing to another population and recurrent selection. These techniques can be used alone or in combination with one or more other techniques in a breeding program.

The number of plants used in the initial cross is chosen based on the biology of the species to be used in the method and on breeding programs suitable for that species. The monocotyledonous and dicotyledonous plants mentioned herein can be used in the breeding methods described herein. Plants such as switchgrass, sorghum or sudangrass, and *Miscanthus* are particularly suitable. Breeding techniques applicable to various biomass species are known in the art.

See, e.g., Allard, Principles of Plant Breeding, John Wiley & Sons, Inc. (1960); Simmonds, Principles of Crop Improvement, Longman Group Limited (1979); and, Jensen, Plant Breeding Methodology, John Wiley & Sons, Inc. (1988). For example, breeding techniques applicable to open-pollinated species such as switchgrass are known. See, e.g., Vogel and Jung, *Critical Rev. Plant Sci.* 20:15-49 (2001).

Progeny of the cross of parental plants are screened for those that have a different biomass composition relative to corresponding control plants. Progeny that can be screened include descendants of $F_1$, $F_2$, $F_3$, $F_4$, $F_5$, $F_6$ and subsequent generation plants, $BC_1$, $BC_2$, $BC_3$, and subsequent generation plants, or $F_1BC_1$, $F_1BC_2$, $F_1BC_3$, and subsequent generation plants. Those progeny that have a difference in biomass composition are selected for further breeding.

Selection can be applied beginning with the $F_1$ generation progeny, or can be applied beginning with progeny of a subsequent generation. For example, an open-pollinated population can utilize a program of selection with progeny testing. Examples of selection with progeny testing breeding programs for switchgrass include Restricted Recurrent Phenotypic Selection (RRPS) and Between and Within Half-Sib Family Selection (B&WFS). Alternatively, a program of mass selection can be used. In mass selection, desirable individual plants are chosen, seed harvested, and the seed composited without testing to produce the next generation. Since selection is based on the maternal parent only, and there is no control over pollination, mass selection amounts to a form of random mating with selection. Mass selection typically increases the proportion of desired genotypes in the population.

As another alternative, plants of an open-pollinated species can be used as parents in an initial cross to generate a synthetic variety. A synthetic variety is produced by crossing several parental plants. The number of parental plant varieties, populations, wild accessions, ecotypes, and the like, that are used to generate a synthetic can vary from as little as 10 to as many as 500. Typically, about 100 to 300 varieties, populations, etc., are used parents to generate a synthetic variety. Seed from the parental seed production plot of a synthetic variety can subsequently undergo one or two generations of multiplication, depending on the amount of seed produced in the parental plot before being subjected to selection as discussed herein.

Selection and/or screening can be carried out over one or more generations, and/or in more than one geographic location. In addition, selection and/or screening can be applied during a particular developmental stage in which the phenotype is expected to be exhibited by the plant. Selection and/or screening is carried out to choose those plants having a statistically significant difference in biomass composition relative to a control plant or to the average of a control population and/or those plants having a statistically significant difference in conversion efficiency relative to a control plant or to the average of a control population.

Plant lines and varieties obtained by the methods described herein typically have a difference in biomass composition that is statistically significantly different relative to a control at $p \leq 0.05$ with an appropriate parametric or non-parametric statistic, e.g., Chi-square test, Student's t-test, Mann-Whitney test, or F-test. In some embodiments, the difference is statistically significant at $p<0.01$, $p<0.005$, or $p<0.001$.

In some cases, selection for other useful traits is also carried out, e.g., selection for fungal resistance or drought tolerance. Selection for such other traits can be carried out before, during or after identification of individual plants that possess a difference in biomass composition.

III. Polypeptides

Polypeptides described herein include biomass composition-modulating polypeptides. In some embodiments, biomass composition-modulating polypeptides are effective to modulate biomass composition when expressed in a plant or plant cell. In some embodiments, reduced expression of biomass composition-modulating polypeptides is effective to modulate biomass composition in a plant or plant cell. Such polypeptides typically contain at least one domain indicative of a biomass composition-modulating polypeptide, as described in more detail herein. Biomass composition-modulating polypeptides also typically have an HMM bit score that is greater than 65 as described in more detail herein. In some embodiments, biomass composition-modulating polypeptides have greater than 80% identity to SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567 as described in more detail herein.

A. Domains Indicative of Biomass Composition-Modulating Polypeptides

A biomass composition-modulating polypeptide can contain a 2OG-Fe(II) oxygenase superfamily domain, which is predicted to be characteristic of a biomass composition-modulating polypeptide. SEQ ID NO: 471 sets forth the amino acid sequence of a *Oryza sativa* clone, identified herein as GI_115456701, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 211 to 309 of SEQ ID NO: 471. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, and 976. The 2OG-Fe(II) oxygenase superfamily domains of such sequences are set forth in the Sequence Listing. The 2OG-Fe(II) oxygenase superfamily contains members of the 2-oxoglutarate (2OG) and Fe(II)-dependent oxygenase superfamily. See Aravind and Koonin, *Genome Biol.* 2(3): RESEARCH0007 (2001). Gibberellin (GA) 20-oxidases are a class of 2OG-dependent dioxygenases that catalyze the conversion of GA12 and GA53 to GA9 and GA20, respectively, via a three-step oxidation at C-20 of the GA skeleton, and uses iron, ascorbate, and 2-oxoglutarate as co-factors. See Oikawa, et al., *Plant Mol. Biol.* 55: 687-700 (2004).

A biomass composition-modulating polypeptide can contain an alpha/beta hydrolase fold (Abhydrolase_3) domain and a carboxylesterase (CO esterase) domain, which are predicted to be characteristic of a biomass composition-modulating polypeptide. A polypeptide containing such Abhydrolase_3 and CO esterase domains can be useful, for example, for modulating sugar content or conversion efficiency. SEQ ID NO: 99 sets forth the amino acid sequence of an *Oryza sativa* clone, identified herein as GI_75324272 that is predicted to encode a polypeptide containing Abhydrolase_3 and CO esterase domains. For example, a biomass composition-modulating polypeptide can comprise an Abhydrolase_3 domain having 60 percent or greater (e.g., 65, 70, 75, 80, 85, 90, 95, 97, 98, 99, or 100 percent) sequence identity to residues 116 to 329 of SEQ ID NO: 99 and a CO esterase domain having 60 percent or greater (e.g., 65, 70, 75, 80, 85, 90, 95, 97, 98, 99, or 100 percent) sequence identity to residues 110 to 210 of SEQ ID NO: 99. In some embodiments, a biomass composition-modulating polypeptide can comprise an Abhydrolase_3 domain and a CO esterase domain having 60 percent or greater (e.g., 65, 70, 75, 80, 85, 90, 95, 97, 98, 99, or 100 percent) sequence identity to the Abhydrolase 3 and CO esterase domains of one or more of the polypeptides set forth in SEQ ID NOs: 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, and 1139. The Abhydrolase_3 and CO esterase domains of such sequences are set forth in the Sequence Listing. The alpha/beta hydrolase fold is common to a number of hydrolytic enzymes of differing phylogenetic origin and catalytic function (e.g., proteases, lipases, peroxidases, esterases, epoxide hydrolases and dehalogenases). The core of each enzyme is an alpha/beta-sheet, rather than a barrel, containing 8 strands connected by helices. See, Ollis et al., *Protein Eng.* 5 (3): 197-211 (1992); and Nardini, et al., *Curr. Opin. Strutt. Biol.* 9 (6): 732-7 (1999). The CO esterases are in the family of proteins containing an Alpha/beta hydrolase fold.

A biomass composition-modulating polypeptide can be a GID1 GA receptor and can contain one or more N-terminal helical GID1 regions, DELLA protein-interacting sites, and GA-binding amino acids as described in Voegele et al., *J. Exp. Botany* 62(14):5131-5147 (2011). For example, a biomass composition-modulating polypeptide can be a GID1 GA receptor and can contain include an alpha-helix a corresponding to approximately residues 9 to 13 of SEQ ID NO:1072, an alpha-helix b corresponding to approximately residues 18 to 34 of SEQ ID NO:1072, an alpha-helix c corresponding to approximately residues 42 to 49 of SEQ ID NO:1072, DELLA protein-interacting sites corresponding to approximately residues 6 to 7, 9, 18 to 19, 21 to 23, 25 to 30, 32, 44 to 45, 48 to 49, 51, 125 to 126, 129, and/or 322 to 326 of SEQ ID NO: 1072, GA-binding amino acids corresponding to approximately residues 24, 27, 28, 31, 35, 113 to 116, 126, 127, 191, 238, 239, 243, 244, 247, 320, 322, and/or 323 of SEQ ID NO: 1072, and HGG GA-binding amino acid motif corresponding to approximately residues 114 to 116 of SEQ ID NO: 1072, and/or a GXSXG motif corresponding to approximately residues 189 to 193 of SEQ ID NO: 1072.

A biomass composition-modulating polypeptide can contain a GRAS family transcription factor domain (GRAS) and a transcriptional regulator DELLA protein N terminal domain (DELLA), which are predicted to be characteristic of a biomass composition-modulating polypeptide. Decreased expression of a polypeptide containing such domains can be useful, for example, for modulating sugar content and/or conversion efficiency. SEQ ID NO: 188 sets forth the amino acid sequence of an *Oryza saliva* clone, identified herein as GI_75139772 that is predicted to encode a polypeptide containing a GRAS domain and a DELLA domain. For example, a biomass composition-modulating polypeptide can comprise a GRAS domain having 60 percent or greater (e.g., 65, 70, 75, 80, 85, 90, 95, 97, 98, 99, or 100 percent) sequence identity to residues 168 to 528 of SEQ ID NO: 188 and a DELLA domain having 60 percent or greater (e.g., 65, 70, 75, 80, 85, 90, 95, 97, 98, 99, or 100 percent) sequence identity to residues 27 to 97 of SEQ ID NO: 188. In some embodiments, a biomass composition-modulating polypeptide can comprise a GRAS domain and a DELLA domain having 60 percent or greater (e.g., 65, 70, 75, 80, 85, 90, 95, 97, 98, 99, or 100 percent) sequence identity to the GRAS and DELLA domains of one or more of the polypeptides set forth in SEQ ID NOs: 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 1009, 1010, 1011, 1012, 1013, 1014, 1015, 1016, 1017, 1018, 1019, 1020, 1021, 1022, and 1023. Transcription factors in the GRAS family share a variable amino-terminus and a highly conserved carboxyl-terminus that contains five recognizable motifs. The transcription factors may be involved in development and other processes. See, e.g., Pysh et al., *Plant J.,* 18:111-119 (1999); and Bolle, et al., *Genes Dev.,* 14:1269-1278 (2000). DELLA proteins are transcriptional regulators that are down regulated when gibberellins bind to a nuclear receptor GIBBERELLIN INSENSITIVE DWARF1 (GID1). GID1 forms a complex with DELLA proteins and targets the DELLA proteins for degradation through the 26S protcasome. The N terminal of DELLA proteins contains conserved DELLA and VHYNP motifs that are important for GID1 binding and proteolysis of the DELLA proteins. See, Murase, et al., Nature, 456:459-463 (2008).

A biomass composition-modulating polypeptide can contain a 2OG-Fe(II) oxygenase superfamily domain, which is predicted to be characteristic of a biomass composition-modulating polypeptide. A polypeptide containing such a domain can be useful, for example, for modulating sugar content or conversion efficiency. SEQ ID NO: 1 sets forth the amino acid sequence of a *Triticum aestivum* clone, identified herein as GI_85540948, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 209 to 306 of SEQ ID NO: 1. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, and 1008. The 2OG-Fe(II) oxygenase superfamily domain of such sequences are set forth in the Sequence Listing. The 2OG-Fe(II) oxygenase superfamily is described above. GA 3-oxidases are a class of 2OG-dependent dioxygenases, classified under EC 1.14.11.15, that convert GA9 and GA20 to GA4 and GA1, respectively. See, Oikawa, et al., 2004, supra.

A biomass composition-modulating polypeptide can contain a 2OG-Fe(II) oxygenase superfamily domain, which is predicted to be characteristic of a biomass composition-modulating polypeptide. Decreased expression of a polypeptide containing such a domain can be useful, for example, for modulating sugar content or conversion efficiency. SEQ ID NO: 287 sets forth the amino acid sequence of a *Arabidopsis thaliana* clone, identified herein as G2OX1_ARATH, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 167 to 273 of SEQ ID NO: 287. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273. The 2OG-Fe(II) oxygenase superfamily domain of such sequences are set forth in the Sequence Listing. The 2OG-Fe(II) oxygenase superfamily is described above. GA 2-oxidases are a class of 2OG-dependent dioxygenases, classified under EC 1.14.11.13, that inactivate GAs by 2 beta-hydroxylation. See, Hedden and Phillips, *Trends Plant Sci.*, 5:523-530 (2000).

A biomass composition-modulating polypeptide can contain a cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1429 sets forth the amino acid sequence of a *Gibberella intermedia* clone, identified herein as cytochrome P450 or CYP68B1 or GiGA20-oxidase, that is predicted to encode a polypeptide containing a Cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 142 to 500 of SEQ ID NO: 1429. In some embodiments, a biomass composition-modulating polypeptide can comprise a cytochrome P450 domain having 60 percent or greater (e.g., 65, 70, 75, 80, 85, 90, 95, 97, 98, 99, or 100 percent) sequence identity to the cytochrome P450 domain of one or more of the polypeptides set forth in SEQ ID NOs: 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, and 1541. The cytochrome P450 domains of such sequences are set forth in the Sequence Listing. The Cytochrome P450 family is described by, for example, Pinot and Beisson, *FEBS J.*, 78(2):195-205 (2011).

A biomass composition-modulating polypeptide can contain a Cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1386 sets forth the amino acid sequence of a *Gibberella intermedia* clone, identified herein as cytochrome P450 or GA14-synthase, that is predicted to encode a polypeptide containing a cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 176 to 504 of SEQ ID NO: 1386. In some embodiments, a biomass composition-modulating polypeptide can comprise a Cytochrome P450 domain having 60 percent or greater (e.g., 65, 70, 75, 80, 85, 90, 95, 97, 98, 99, or 100 percent) sequence identity to the Cytochrome P450 domain of one or more of the polypeptides set forth in SEQ ID NOs: 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, and 1428. The cytochrome P450 domains of such sequences are set forth in the Sequence Listing. The Cytochrome P450 family is described, for example, by Pinot and Beisson, *FEBS J.*, 78(2):195-205 (2011).

A biomass composition-modulating polypeptide can contain a cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1274 sets forth the amino acid sequence of a *Gibberella intermedia* clone, identified herein as cytochrome P450 or CYP69A1 or C13-oxidase, that is predicted to encode a polypeptide containing a cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 98 to 368 of SEQ ID NO: 1274. In some embodiments, a biomass composition-modulating polypeptide can comprise a cytochrome P450 domain having 60 percent or greater (e.g., 65, 70, 75, 80, 85, 90, 95, 97, 98, 99, or 100 percent) sequence identity to the Cytochrome P450 domain of one or more of the polypeptides set forth in SEQ ID NOs: 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, and 1385. The cytochrome P450 domains of such sequences are set forth in the Sequence Listing. The Cytochrome P450 family is described, for example, by Pinot and Beisson, *FEBS J.*, 78(2):195-205 (2011).

In some embodiments, a biomass composition-modulating polypeptide is truncated at the amino- or carboxy-terminal end of a naturally occurring polypeptide.

A truncated polypeptide may retain certain domains of the naturally occurring polypeptide while lacking others. Thus, length variants that are up to 5 amino acids shorter or longer typically exhibit the biomass composition-modulating activity of a truncated polypeptide. In some embodiments, a truncated polypeptide is a dominant negative polypeptide. Expression in a plant of such a truncated polypeptide confers a difference in biomass composition of a plant as compared to the corresponding level of a control plant that does not comprise the truncation.

B. Functional Homologs Identified by Reciprocal BLAST

In some embodiments, one or more functional homologs of a reference biomass composition-modulating polypeptide defined by one or more of the Pfam descriptions indicated above are suitable for use as biomass composition-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a biomass composition-modulating polypeptide, or by combining domains from the coding sequences for different naturally-occurring biomass composition-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass composition-modulating polypeptides. Sequence analysis can involve BLAST, Reciprocal BLAST, or PSI-BLAST analysis of nonredundant databases using a biomass composition-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a biomass composition-modulating polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in biomass composition-modulating polypeptides, e.g., conserved functional domains.

Conserved regions can be identified by locating a region within the primary amino acid sequence of a biomass composition-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1A:
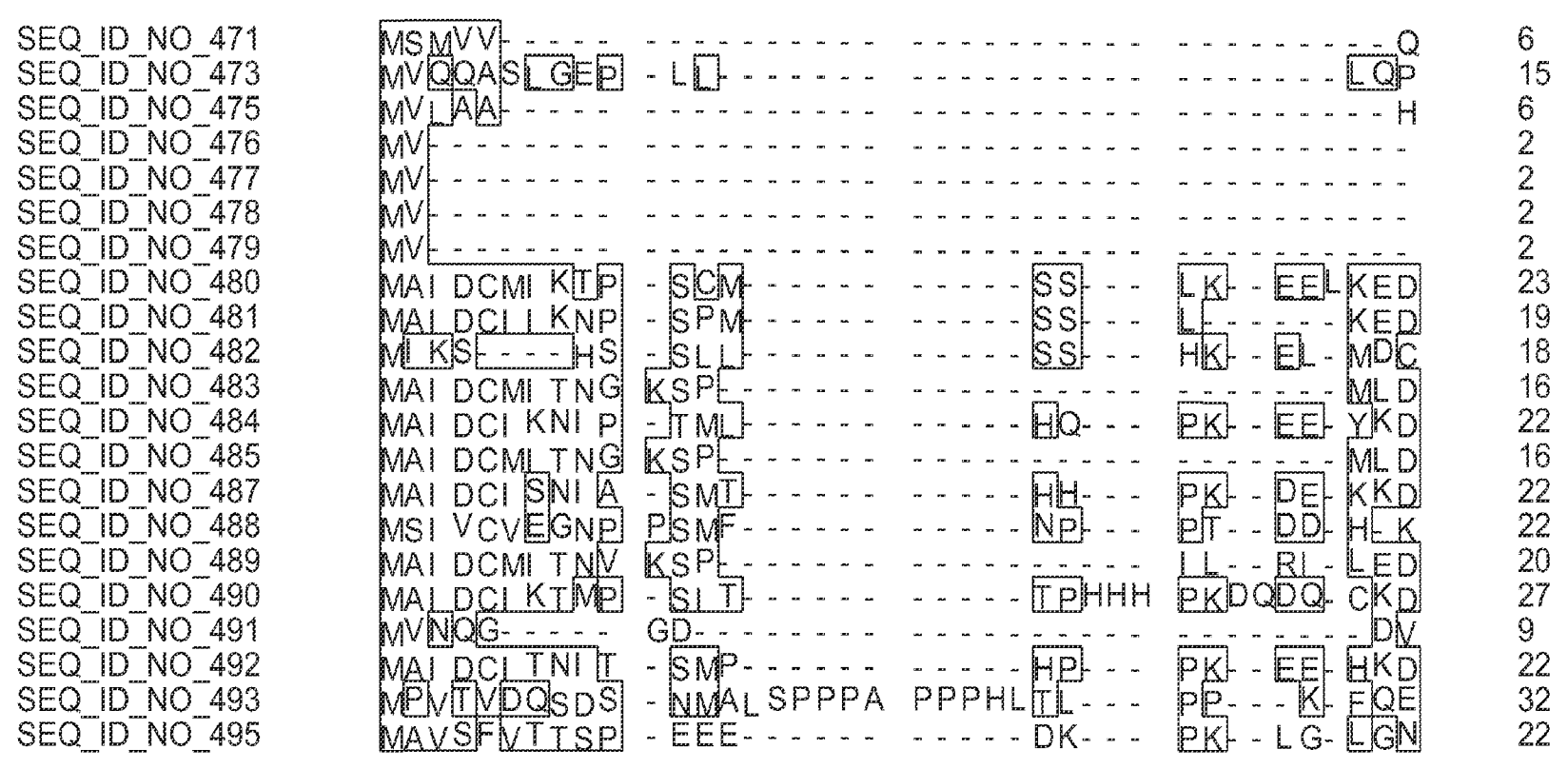
Figure 1C:
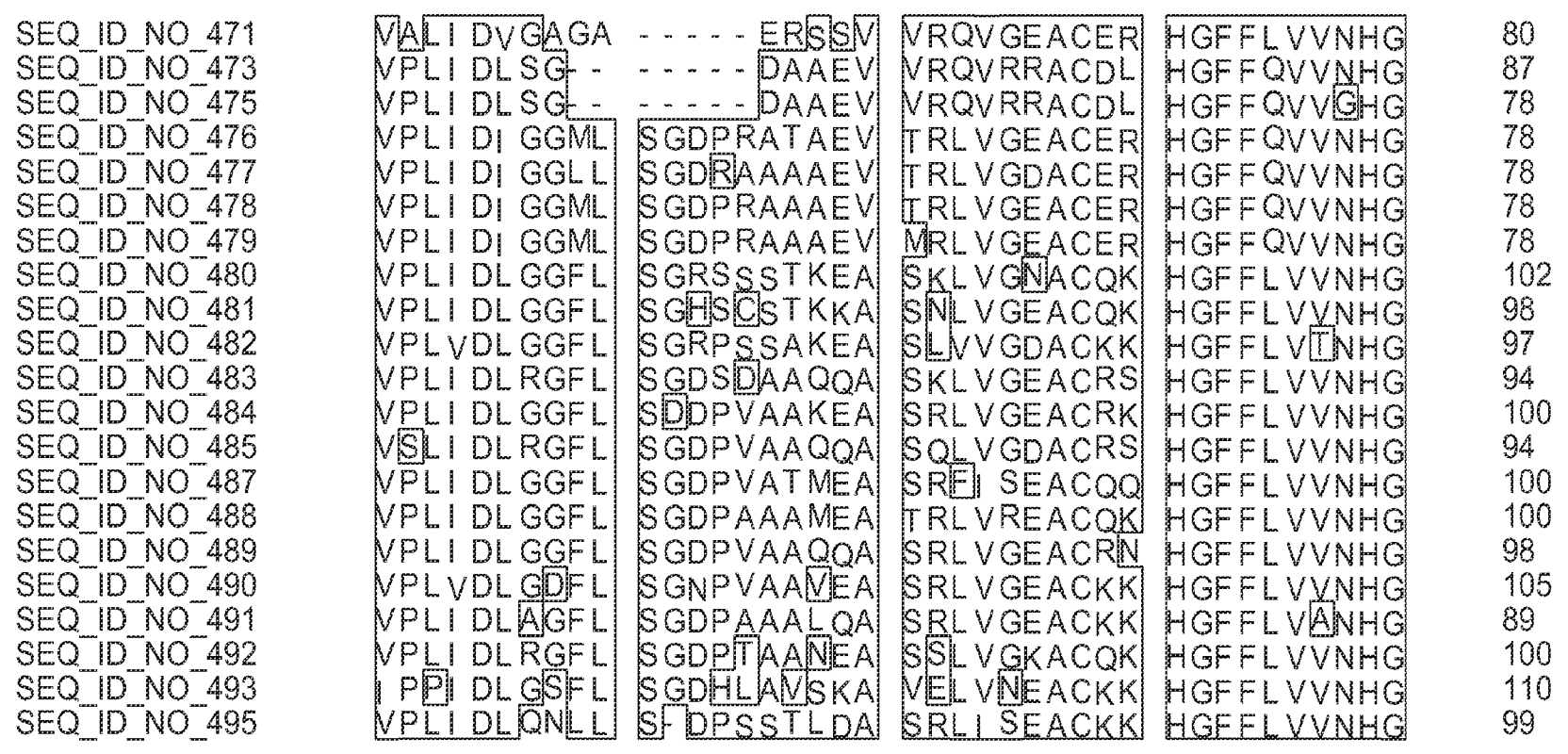

Examples of amino acid sequences of functional homologs of the polypeptide set forth in SEQ ID NO: 471 are provided in FIG. 1 and in the Sequence Listing. Such functional homologs include, for example, CeresAnnot_8631464_Sb (SEQ ID NO: 473), CeresClone_329121_Zm (SEQ ID NO: 475), GI_75276875_Ta (SEQ ID NO: 476), GI_13625523_Lp (SEQ ID NO: 477), GI_49065946_Hv (SEQ ID NO: 478), GI_157683559_Dasypyrum_villosum (SEQ ID NO: 479), GI_4164141_Lactuca_sativa (SEQ ID NO: 480), GI_187455574_Helianthus_annuus (SEQ ID NO: 481), GI_190192210_Chrysanthemum (SEQ ID NO: 482), GI_7328337_Solanum_dulcamara (SEQ ID NO: 483), GI_8919865_Citrus (SEQ ID NO: 484), GI_326581983_Capsicum_annuum (SEQ ID NO: 485), CeresClone_1842451_Gh (SEQ ID NO: 487), GI_99032729_Vitis_vinifera (SEQ ID NO: 488), GI_3327245_Nicotiana_tabacum (SEQ ID NO: 489), GI_34013374_Populus_alba (SEQ ID NO: 490), GI_303303656_Ipomoea_nil (SEQ ID NO: 491), GI_18496057_Fagus_sylvatica (SEQ ID NO: 492), GI_255541396_Ricinus_communis (SEQ ID NO: 493), CeresAnnot_878887_Arabidopsis_thaliana (SEQ ID NO: 495), GI_210142296 (SEQ ID NO: 496), CeresAnnot_8669917 (SEQ ID NO: 498), GI_15242189 (SEQ ID NO: 499), GI_255927093 (SEQ ID NO: 500), GI_67462129 (SEQ ID NO: 501), GI_10800974 (SEQ ID NO: 502), GI_6855711 (SEQ ID NO: 503), GI_223943497 (SEQ ID NO: 504), GI_210142300 (SEQ ID NO: 505), GI_255927115 (SEQ ID NO: 506), CeresAnnot_1497117 (SEQ ID NO: 508), GI_255927101 (SEQ ID NO: 509), GI_335056045 (SEQ ID NO: 510), GI_125546514 (SEQ ID NO: 511), GI_208609486 (SEQ ID NO: 512), GI_20149239 (SEQ ID NO: 513), GI_109452794 (SEQ ID NO: 514), GI_255927111 (SEQ ID NO: 515), CeresAnnot_881675 (SEQ ID NO: 517), GI_9791186 (SEQ ID NO: 518), GI_255927119 (SEQ ID NO: 519), GI_255927105 (SEQ ID NO: 520), GI_30102973 (SEQ ID NO: 521), GI_1854637 (SEQ ID NO: 522), GI_210142292 (SEQ ID NO: 523), GI_82568041 (SEQ ID NO: 524), GI_297795983 (SEQ ID NO: 525), GI_255927103 (SEQ ID NO: 526), GI_62320340 (SEQ ID NO: 527), GI_125546516 (SEQ ID NO: 528), GI_77632796 (SEQ ID NO: 529), GI_125528619 (SEQ ID NO: 530), GI_335056055 (SEQ ID NO: 531), GI_255927121 (SEQ ID NO: 532), GI_210142286 (SEQ ID NO: 533), GI_147782450 (SEQ ID NO: 534), GI_226492950 (SEQ ID NO: 535), GI_218196824 (SEQ ID NO: 536), GI_15219842 (SEQ ID NO: 537), GI_2108432 (SEQ ID NO: 538), GI_4164143 (SEQ ID NO: 539), GI_297724127 (SEQ ID NO: 540), GI_21322508 (SEQ ID NO: 541), GI_162458757 (SEQ ID NO: 542), CeresClone_100845866 (SEQ ID NO: 544), GI_242055211 (SEQ ID NO: 545), GI_210142298 (SEQ ID NO: 546), GI_326529611 (SEQ ID NO: 547), GI_1109695 (SEQ ID NO: 548), GI_169403818 (SEQ ID NO: 549), GI_2108428 (SEQ ID NO: 550), GI_1848146 (SEQ ID NO: 551), GI_210142288 (SEQ ID NO: 552), GI_13625525 (SEQ ID NO: 553), GI_188474853 (SEQ ID NO: 554), GI_75276876 (SEQ ID NO: 555), GI_335056059 (SEQ ID NO: 556), CeresClone_624633 (SEQ ID NO: 558), GI_210142302 (SEQ ID NO: 559), CeresClone_818172 (SEQ ID NO: 561), GI_297810833 (SEQ ID NO: 562), GI_115441469 (SEQ ID NO: 563), GI_27124556 (SEQ ID NO: 564), CeresClone_639483 (SEQ ID NO: 566), GI_255927091 (SEQ ID NO: 567), GI_48475183 (SEQ ID NO: 568), GI_13625519 (SEQ ID NO: 569), GI_210142290 (SEQ ID NO: 570), GI_30519873 (SEQ ID NO: 571), GI_225453833 (SEQ ID NO: 572), GI_297201566 (SEQ ID NO: 573), GI_159902527 (SEQ ID NO: 574), GI_302797527 (SEQ ID NO: 575), GI_168044400 (SEQ ID NO: 576), GI_233142142 (SEQ ID NO: 577), GI_330985521 (SEQ ID NO: 578), GI_225431689 (SEQ ID NO: 579), GI_168015263 (SEQ ID NO: 580), CeresAnnot_1474270 (SEQ ID NO: 582), GI_296089115 (SEQ ID NO: 583), GI_89574456 (SEQ ID NO: 584), GI_295691295 (SEQ ID NO: 585), GI_219362733 (SEQ ID NO: 586), GI_147865914 (SEQ ID NO: 587), GI_53139594 (SEQ ID NO: 588), GI_187455576 (SEQ ID NO: 589), GI_320462770 (SEQ ID NO: 590), CeresAnnot_1503804 (SEQ ID NO: 592), GI_198286468 (SEQ ID NO: 593), GI_4321498 (SEQ ID NO: 594), 18470389 (SEQ ID NO: 595), CeresClone_539430 (SEQ ID NO: 597), CeresClone_518341 (SEQ ID NO: 599), GI_89574455 (SEQ ID NO: 600), GI_330958505 (SEQ ID NO: 601), GI_254419812 (SEQ ID NO: 602), CeresAnnot_1452184 (SEQ ID NO: 604), GI_86605411 (SEQ ID NO: 605), GI_329847655 (SEQ ID NO: 606), GI_237682458 (SEQ ID NO: 607), GI_49065948 (SEQ ID NO: 608), GI_255558510 (SEQ ID NO: 609), GI_326332772 (SEQ ID NO: 610), CeresClone_473318 (SEQ ID NO: 612), GI_116785413 (SEQ ID NO: 613), GI_297242535 (SEQ ID NO: 614), GI_195976661 (SEQ ID NO: 615), CeresAnnot_8644543 (SEQ ID NO: 617), GI_125486693 (SEQ ID NO: 618), GI_53139630 (SEQ ID NO: 619), GI_109729787 (SEQ ID NO: 620), GI_53139646 (SEQ ID NO: 621), GI_53139614 (SEQ ID NO: 622), GI_12320815 (SEQ ID NO: 623), GI_256420048 (SEQ ID NO: 624), GI_255583171 (SEQ ID NO: 625), GI_159902523 (SEQ ID NO: 626), GI_213876865 (SEQ ID NO: 627), GI_195976665 (SEQ ID NO: 628), GI_1666094 (SEQ ID NO: 629), GI_9650811 (SEQ ID NO: 630), GI_2108434 (SEQ ID NO: 631), GI_167644154 (SEQ ID NO: 632), GI_302882991 (SEQ ID NO: 633), GI_160623443 (SEQ ID NO: 634), GI_311899282 (SEQ ID NO: 635), GI_125572881 (SEQ ID NO: 636), GI_53139590 (SEQ ID NO: 637), GI_55978167 (SEQ ID NO: 638), GI_331699132 (SEQ ID NO: 639), GI_325106136 (SEQ ID NO: 640), GI_53139664 (SEQ ID NO: 641), CeresClone_1827193 (SEQ ID NO: 643), GI_160623445 (SEQ ID NO: 644), GI_134075373 (SEQ ID NO: 645), GI_222875436 (SEQ ID NO: 646), GI_2224890 (SEQ ID NO: 647), GI_226305722 (SEQ ID NO: 648), GI_50428327 (SEQ ID NO: 649), GI_302797040 (SEQ ID NO: 650), GI_104295012 (SEQ ID NO: 651), GI_159043926 (SEQ ID NO: 652), GI_254253748 (SEQ ID NO: 653), GI_60498576 (SEQ ID NO: 654), GI_297852192 (SEQ ID NO: 655), GI_302141747 (SEQ ID NO: 656), GI_111224710 (SEQ ID NO: 657), GI_53139592 (SEQ ID NO: 658), GI_320324375 (SEQ ID NO: 659), GI_68509984 (SEQ ID NO: 660), GI_339470611 (SEQ ID NO: 661), CeresAnnot_1468944 (SEQ ID NO: 663), GI_330890071

(SEQ ID NO: 664), GI_225459697 (SEQ ID NO: 665), GI_239817805 (SEQ ID NO: 666), GI_195976667 (SEQ ID NO: 667), GI_51011360 (SEQ ID NO: 668), GI_255572455 (SEQ ID NO: 669), GI_189409355 (SEQ ID NO: 670), GI_302800904 (SEQ ID NO: 671), GI_168012845 (SEQ ID NO: 672), GI_217037949 (SEQ ID NO: 673), GI_312195518 (SEQ ID NO: 674), GI_4321496 (SEQ ID NO: 675), GI_5359492 (SEQ ID NO: 676), GI_53139608 (SEQ ID NO: 677), GI_320588046 (SEQ ID NO: 678), GI_53139640 (SEQ ID NO: 679), GI_333440997 (SEQ ID NO: 680), GI_325189696 (SEQ ID NO: 681), GI_4321494 (SEQ ID NO: 682), GI_53139588 (SEQ ID NO: 683), GI_325184325 (SEQ ID NO: 684), GI_255556241 (SEQ ID NO: 685), GI_302790077 (SEQ ID NO: 686), CeresAnnot_1444168 (SEQ ID NO: 688), GI_159902531 (SEQ ID NO: 689), GI_3402332 (SEQ ID NO: 690), GI_294011471 (SEQ ID NO: 691), GI_320462774 (SEQ ID NO: 692), GI_255556243 (SEQ ID NO: 693), CeresAnnot_1456250 (SEQ ID NO: 695), GI_320462772 (SEQ ID NO: 696), GI_187729689 (SEQ ID NO: 697), GI_114570248 (SEQ ID NO: 698), GI_74273643 (SEQ ID NO: 699), GI_317029127 (SEQ ID NO: 700), GI_1381673 (SEQ ID NO: 701), GI_317158331 (SEQ ID NO: 702), GI_168041562 (SEQ ID NO: 703), CeresClone_1647898 (SEQ ID NO: 705), GI_168004189 (SEQ ID NO: 706), GI_195976671 (SEQ ID NO: 707), GI_168033355 (SEQ ID NO: 708), GI_255637063 (SEQ ID NO: 709), GI_218764876 (SEQ ID NO: 710), GI_47499085 (SEQ ID NO: 711), GI_229489577 (SEQ ID NO: 712), GI_53139616 (SEQ ID NO: 713), GI_16124455 (SEQ ID NO: 714), GI_92115002 (SEQ ID NO: 715), GI_262200288 (SEQ ID NO: 716), GI_53139668 (SEQ ID NO: 717), GI_20149241 (SEQ ID NO: 718), GI_311109251 (SEQ ID NO: 719), GI_222875432 (SEQ ID NO: 720), GI_190192208 (SEQ ID NO: 721), CeresClone_1370404 (SEQ ID NO: 723), GI_298486918 (SEQ ID NO: 724), GI_53139624 (SEQ ID NO: 725), GI_40233167 (SEQ ID NO: 726), GI_301123383 (SEQ ID NO: 727), GI_48057695 (SEQ ID NO: 728), GI_168050680 (SEQ ID NO: 729), GI_29831348 (SEQ ID NO: 730), GI_115470777 (SEQ ID NO: 731), GI_255642379 (SEQ ID NO: 732), GI_302797547 (SEQ ID NO: 733), GI_53139648 (SEQ ID NO: 734), GI_326385638 (SEQ ID NO: 735), GI_147916856 (SEQ ID NO: 736), GI_486625 (SEQ ID NO: 737), GI_197090668 (SEQ ID NO: 738), GI_154705630 (SEQ ID NO: 739), GI_168032021 (SEQ ID NO: 740), GI_58700543 (SEQ ID NO: 741), GI_317454944 (SEQ ID NO: 742), GI_198286476 (SEQ ID NO: 743), GI_332531325 (SEQ ID NO: 744), GI_302821145 (SEQ ID NO: 745), GI_255927085 (SEQ ID NO: 746), GI_8778664 (SEQ ID NO: 747), GI_229490954 (SEQ ID NO: 748), GI_255927099 (SEQ ID NO: 749), GI_34013370 (SEQ ID NO: 750), GI_225455655 (SEQ ID NO: 751), GI_168046914 (SEQ ID NO: 752), CeresClone_156575 (SEQ ID NO: 754), CeresClone_1962928 (SEQ ID NO: 756), GI_37359180 (SEQ ID NO: 757), US20040010815-0080 (SEQ ID NO: 758), GI_308810887 (SEQ ID NO: 759), GI_296084082 (SEQ ID NO: 760), GI_102139962 (SEQ ID NO: 761), GI_46127407 (SEQ ID NO: 762), GI_255927107 (SEQ ID NO: 763), GI_13625521 (SEQ ID NO: 764), GI_224083474 (SEQ ID NO: 765), CeresAnnot_1509446 (SEQ ID NO: 767), GI_28316358 (SEQ ID NO: 768), GI_302821073 (SEQ ID NO: 769), GI_217037951 (SEQ ID NO: 770), CeresClone_526491 (SEQ ID NO: 772), GI_224082360 (SEQ ID NO: 773), CeresAnnot_835213 (SEQ ID NO: 775), GI_53139612 (SEQ ID NO: 776), GI_224120176 (SEQ ID NO: 777), GI_210142294 (SEQ ID NO: 778), GI_9971219 (SEQ ID NO: 779), GI_326475334 (SEQ ID NO: 780), GI_255539617 (SEQ ID NO: 781), GI_255927109 (SEQ ID NO: 782), GI_186695270 (SEQ ID NO: 783), GI_10800976 (SEQ ID NO: 784), GI_255927097 (SEQ ID NO: 785), CeresClone_100062984 (SEQ ID NO: 787), GI_115361480 (SEQ ID NO: 788), GI_2262201 (SEQ ID NO: 789), GI_3327247 (SEQ ID NO: 790), GI_335056001 (SEQ ID NO: 791), GI_111225835 (SEQ ID NO: 792), GI_317106632 (SEQ ID NO: 793), GI_255927087 (SEQ ID NO: 794), GI_9791188 (SEQ ID NO: 795), GI_9791187 (SEQ ID NO: 796), GI_146270975 (SEQ ID NO: 797), CeresAnnot_8732690 (SEQ ID NO: 799), GI_51011362 (SEQ ID NO: 800), GI_303283824 (SEQ ID NO: 801), GI_320589215 (SEQ ID NO: 802), GI_255927089 (SEQ ID NO: 803), GI_330992883 (SEQ ID NO: 804), GI_222875434 (SEQ ID NO: 805), GI_53139620 (SEQ ID NO: 806), GI_297799454 (SEQ ID NO: 807), GI_304570785 (SEQ ID NO: 808), GI_89574458 (SEQ ID NO: 809), GI_238507652 (SEQ ID NO: 810), CeresAnnot_1471005 (SEQ ID NO: 812), WO2011060920-24495 (SEQ ID NO: 813), GI_50428325 (SEQ ID NO: 814), GI_60390163 (SEQ ID NO: 815), GI_158392463 (SEQ ID NO: 816), GI_1144390 (SEQ ID NO: 817), GI_225431709 (SEQ ID NO: 818), CeresAnnot_8461546 (SEQ ID NO: 820), GI_255573359 (SEQ ID NO: 821), GI_302759260 (SEQ ID NO: 822), GI_16118889 (SEQ ID NO: 823), GI_217072494 (SEQ ID NO: 824), GI_340519930 (SEQ ID NO: 825), GI_301123381 (SEQ ID NO: 826), GI_53139652 (SEQ ID NO:827), GI_302790059 (SEQ ID NO:828), GI_257484083 (SEQ ID NO:829), GI_12231168 (SEQ ID NO:830), GI_82568007 (SEQ ID NO:831), GI_53139654 (SEQ ID NO: 832), GI_255927117 (SEQ ID NO: 833), GI_119501723 (SEQ ID NO: 834), GI_189206996 (SEQ ID NO: 835), GI_60498578 (SEQ ID NO: 836), GI_15422154 (SEQ ID NO: 837), GI_198286472 (SEQ ID NO: 838), GI_255927113 (SEQ ID NO: 839), CeresClone_1101515 (SEQ ID NO: 841), GI_208609488 (SEQ ID NO: 842), GI_197103783 (SEQ ID NO: 843), GI_53139600 (SEQ ID NO: 844), GI_1581592 (SEQ ID NO: 845), GI_302381882 (SEQ ID NO: 846), GI_198286480 (SEQ ID NO: 847), CeresAnnot_1522333 (SEQ ID NO: 849), GI:225465379 (SEQ ID NO: 850), GI:357114308 (SEQ ID NO: 851), GI:242076892 (SEQ ID NO: 852), GI:255548069 (SEQ ID NO: 853), GI:356521217 (SEQ ID NO: 854), GI:147865705 (SEQ ID NO: 855), GI:350540006 (SEQ ID NO: 856), GI:326491817 (SEQ ID NO: 857), GI:225426514 (SEQ ID NO: 858), GI:225453648 (SEQ ID NO: 859), GI:226498686 (SEQ ID NO: 860), GI:326494732 (SEQ ID NO: 861), GI:116311010 (SEQ ID NO: 862), GI:115460102 (SEQ ID NO: 863), GI:242040385 (SEQ ID NO: 864), GI:116783156 (SEQ ID NO: 865), 01:297808467 (SEQ ID NO: 866), GI:116791020 (SEQ ID NO: 867), GI:302769898 (SEQ ID NO: 868), GI:116793430 (SEQ ID NO: 869), GI:18402081 (SEQ ID NO: 870), GI:116792100 (SEQ ID NO: 871), GI:168014854 (SEQ ID NO: 872), GI:194703858 (SEQ ID NO: 873), GI:357475523 (SEQ ID NO: 874), GI:116784279 (SEQ ID NO: 875), GI:116793277 (SEQ ID NO: 876), GI:294463977 (SEQ ID NO: 877), GI:357468779 (SEQ ID NO: 878), GI:268638403 (SEQ ID NO: 879), GI:159902533 (SEQ ID NO: 880), GI:224286184 (SEQ ID NO: 881), GI:357475519 (SEQ ID NO: 882), GI:125562561 (SEQ ID NO: 883), 01:116780785 (SEQ ID NO: 884), GI:116786939 (SEQ ID NO: 885), GI:357461273 (SEQ ID NO: 886), GI:222613187 (SEQ ID NO: 887), GI:357475529 (SEQ ID NO: 888), GI:168003319 (SEQ ID NO: 889), GI:297809271 (SEQ ID NO: 890), GI:224284972 (SEQ ID NO: 891), GI:297809269 (SEQ ID NO: 892), GI:116794322 (SEQ ID NO: 893), GI:116792196 (SEQ ID NO: 894), GI:357475525 (SEQ ID NO: 895), 01:357440313 (SEQ ID NO: 896), 01:313471276 (SEQ ID NO: 897), GI:357492715 (SEQ ID NO: 898), GI:255557477 (SEQ ID NO: 899), GI:358347250 (SEQ ID NO: 900), GI:357111461 (SEQ ID NO: 901), GI:255575141 (SEQ ID NO: 902), CeresAnnot:8454419 (SEQ ID NO: 904), GI:297820344 (SEQ ID NO: 905), GI:110618325 (SEQ ID NO: 906), GI:166798287 (SEQ ID NO: 907), GI:60476845 (SEQ ID NO: 908), GI:51493449 (SEQ ID NO: 909), GI:326366179 (SEQ ID NO: 910), GI:42566572 (SEQ ID NO: 911), GI:378749126 (SEQ ID NO: 912), GI:219944305 (SEQ ID NO: 913), GI:366047645 (SEQ ID NO: 914), GI:237682460 (SEQ ID NO: 915), GI:333362482 (SEQ ID NO: 916), GI:169793771 (SEQ ID NO: 917), GI:729503 (SEQ ID NO: 918), GI:80973282 (SEQ ID NO: 919), GI:21392365 (SEQ ID NO: 920), GI:222478425 (SEQ ID NO: 921), GI:164454785 (SEQ ID NO: 922), GI:46850468 (SEQ ID NO: 923), GI:225194715 (SEQ ID NO: 924), GI:355645974 (SEQ ID NO: 925), GI:113205138 (SEQ ID NO: 926), GI:2570827 (SEQ ID NO: 927), GI:300834841 (SEQ ID NO: 928), GI:157169280 (SEQ ID NO: 929), GI:348686932 (SEQ ID NO: 930), GI:223997880 (SEQ ID NO: 931), GI:194371667 (SEQ ID NO: 932), GI:297306658 (SEQ ID NO: 933), GI:158515829 (SEQ ID NO: 934), GI:241898888 (SEQ ID NO: 935), GI:62824273 (SEQ ID NO: 936), GI:520802 (SEQ ID NO: 937), GI:307727667 (SEQ ID NO: 938), GI:359359094 (SEQ ID NO: 939), GI:145248559 (SEQ ID NO: 940), GI:227536376 (SEQ ID NO: 941), GI:339495204 (SEQ ID NO: 942), GI:334344062 (SEQ ID NO: 943), GI:145352595 (SEQ ID NO: 944), GI:354570727 (SEQ ID NO: 945), GI:66043929 (SEQ ID NO: 946), GI:302884057 (SEQ ID NO: 947), GI:379063357 (SEQ ID NO: 948), GI:153011110 (SEQ ID NO: 949), GI:19115385 (SEQ ID NO: 950), GI:30060226 (SEQ ID NO: 951), GI:169615517 (SEQ ID NO: 952), GI:149280311 (SEQ ID NO: 953), GI:322705051 (SEQ ID NO: 954), GI:88856654 (SEQ ID NO: 955), GI:117617896 (SEQ ID NO: 956), GI:381201565 (SEQ ID NO: 957), GI:170089053 (SEQ ID NO: 958), GI:379655258 (SEQ ID NO: 959), GI:321253745 (SEQ ID NO: 960), GI:343425662 (SEQ ID NO: 961), GI:226294156 (SEQ ID NO: 962), GI:169768582 (SEQ ID NO: 963), GI:380602393 (SEQ ID NO: 964), GI:315044917 (SEQ ID NO: 965), GI:332529892 (SEQ ID NO: 966), GI:116695054 (SEQ ID NO: 967), GI:346974225 (SEQ ID NO: 968), GI:361126689 (SEQ ID NO: 969), GI:226292680 (SEQ ID NO: 970), GI:119478814 (SEQ ID NO: 971), GI:347829892 (SEQ ID NO: 972), GI:150951140 (SEQ ID NO: 973), GI:149245084 (SEQ ID NO: 974), GI:156064337 (SEQ ID NO: 975), and 01:242780807 (SEQ ID NO: 976). In some cases, a functional homolog of SEQ ID NO: 471 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 471. In some cases, a functional homolog of SEQ ID NO: 471 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 471 described above or set forth in the Sequence Listing.

Figure 2A:
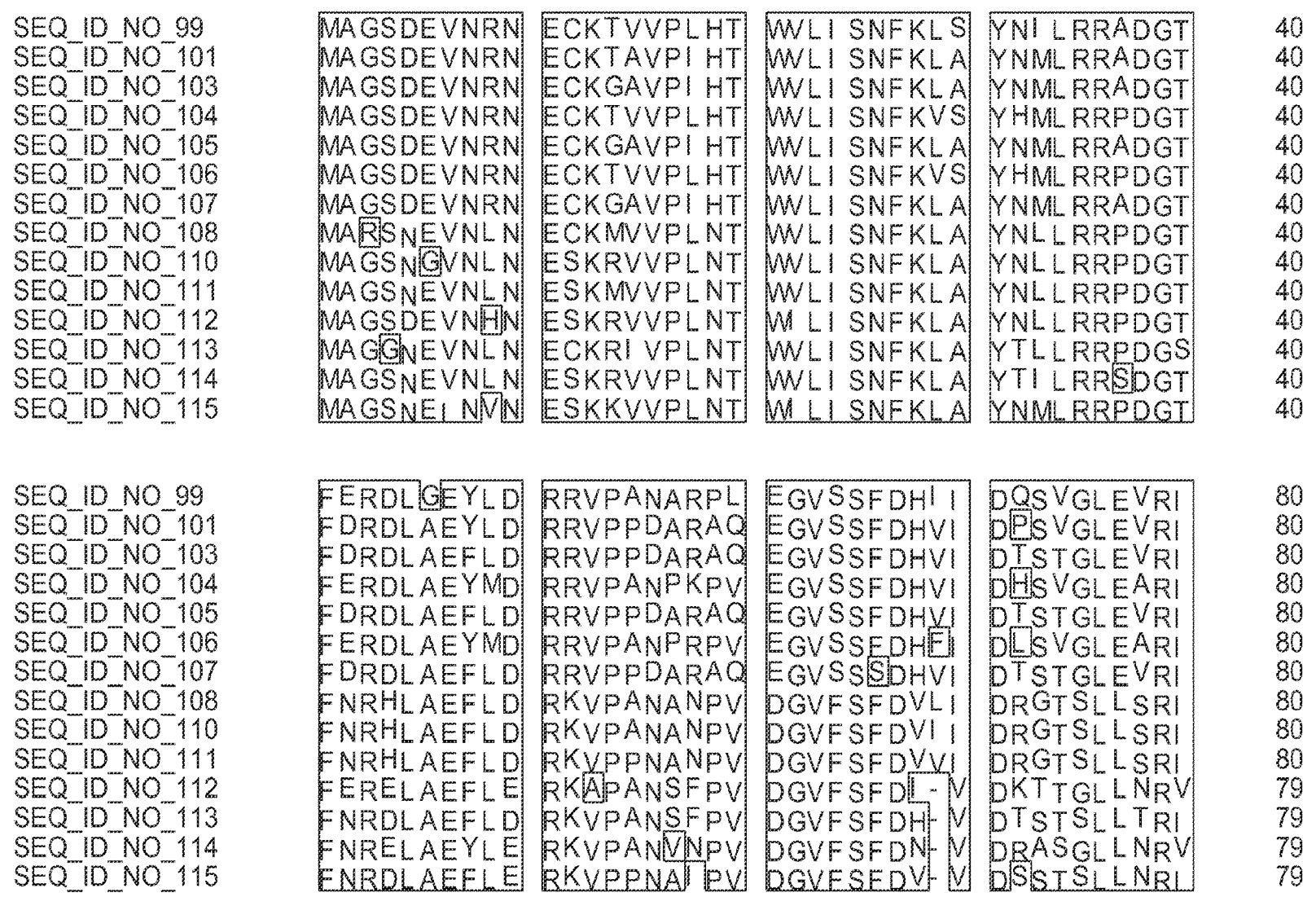
Figure 2B:
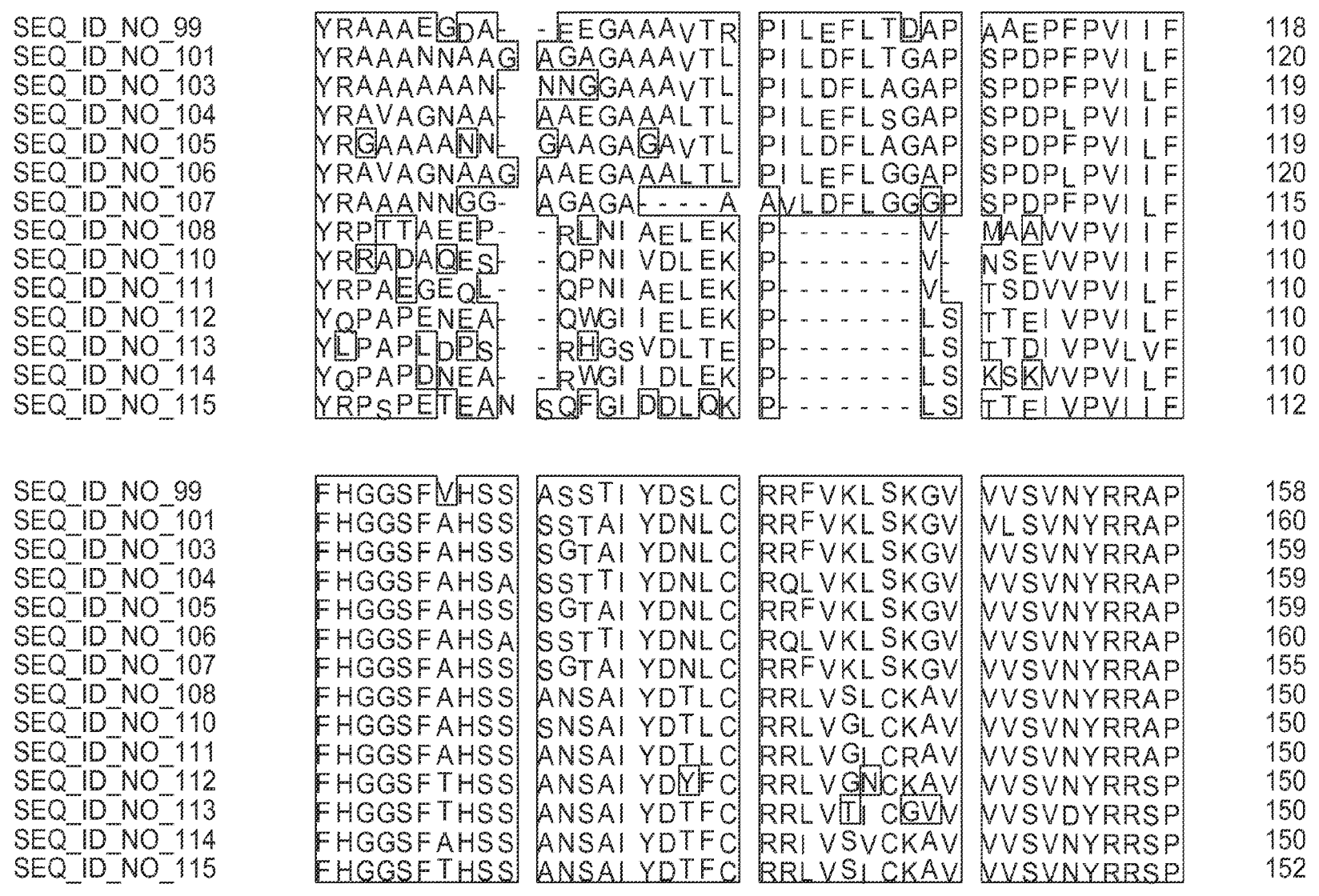

Examples of amino acid sequences of functional homologs of the polypeptide set forth in SEQ ID NO: 99 are provided in FIG. 2 and in the Sequence Listing. Such functional homologs include, for example, CeresClone_1857760 (SEQ ID NO: 101), CeresAnnot_8732528 (SEQ ID NO: 103), GI_156616217 (SEQ ID NO: 104), GI_169159254 (SEQ ID NO: 105), GI_169159270 (SEQ ID NO: 106), GI_169159256 (SEQ ID NO: 107), GI_225346677 (SEQ ID NO: 108), CeresAnnot_1488901 (SEQ ID NO: 110), GI_255542494 (SEQ ID NO: 111), GI_225436847 (SEQ ID NO: 112), GI_315075933 (SEQ ID NO: 113), GI_238654635 (SEQ ID NO: 114), GI_82697973 (SEQ ID NO: 115), GI_218196784 (SEQ ID NO: 116), GI_169159258 (SEQ ID NO: 117), CeresClone_1941624 (SEQ ID NO: 119), GI_225346675 (SEQ ID NO: 120), GI_148612415 (SEQ ID NO: 121), CeresAnnot_1522790 (SEQ ID NO: 123), GI_110747150 (SEQ ID NO: 124), CeresAnnot_1469390 (SEQ ID NO: 126), GI_225346679 (SEQ ID NO: 127), GI_224068739 (SEQ ID NO: 128), GI_225346671 (SEQ ID NO: 129), CeresAnnot_1471748 (SEQ ID NO: 131), GI_147774750 (SEQ ID NO: 132), GI_15240483 (SEQ ID NO: 133), GI_225346673 (SEQ ID NO: 134), GI_298205013 (SEQ ID NO: 135), GI_255567576 (SEQ ID NO: 136), GI_307752615 (SEQ ID NO: 137), GI_297817636 (SEQ ID NO: 138), GI_15229371 (SEQ ID NO: 139), GI_15229905 (SEQ ID NO: 140), GI_307752613 (SEQ ID NO: 141), GI_169159264 (SEQ ID NO: 142), GI_307752617 (SEQ ID NO: 143), GI_297812999 (SEQ ID NO: 144), GI_238654633 (SEQ ID NO: 145), GI_308220216 (SEQ ID NO: 146), CeresAnnot_1444948 (SEQ ID NO: 148), CeresClone_1172108 (SEQ ID NO: 150), GI_169159250 (SEQ ID NO: 151), GI_169159262 (SEQ ID NO: 152), CeresClone_1924067 (SEQ ID NO: 154), GI_169159252 (SEQ ID NO: 155), GI_116794075 (SEQ ID NO: 156), GI_169159248 (SEQ ID NO: 157), GI_169159246 (SEQ ID NO: 158), GI_256772632 (SEQ ID NO: 159), GI_302794147 (SEQ ID NO: 160), GI_296086662 (SEQ ID NO: 161), GI_302782397 (SEQ ID NO: 162), GI_302787771 (SEQ ID NO: 163), GI_156446298 (SEQ ID NO: 164), CeresClone_1843446 (SEQ ID NO: 166), GI_168008743 (SEQ ID NO: 167), CeresAnnot_1449351 (SEQ ID NO: 169), GI_125533918 (SEQ ID NO: 170), GI_297728173 (SEQ ID NO: 171), GI_159902513 (SEQ ID NO: 172), GI_225463177 (SEQ ID NO: 173), CeresClone_566899 (SEQ ID NO: 175), GI_294460127 (SEQ ID NO: 176), GI_147856212 (SEQ ID NO: 177), CeresClone_1647753 (SEQ ID NO: 179), GI_115473685 (SEQ ID NO: 180), GI_82697933 (SEQ ID NO: 181), GI_302788858 (SEQ ID NO: 182), GI_168013809 (SEQ ID NO: 183), GI_302788854 (SEQ ID NO: 184), GI_242068025 (SEQ ID NO: 185), GI_302769524 (SEQ ID NO: 186), GI_148270935 (SEQ ID NO: 187), GI:356535621 (SEQ ID NO: 1024), (SEQ ID NO: 1025), GI:225346669 (SEQ ID NO: 1026), GI:326517960 (SEQ ID NO: 1027), (SEQ ID NO: 1028), GI:168011953 (SEQ ID NO: 1029), GI:21618039_CeresClone:42187_CeresClone:9482 (SEQ ID NO: 1031), (SEQ ID NO: 1032), GI:297829024 (SEQ ID NO: 1033), GI:356576751 (SEQ ID NO: 1034), (SEQ ID NO: 1035), GI:125559352 (SEQ ID NO: 1036), GI:357116238 (SEQ ID NO: 1037), GI:326513536 (SEQ ID NO: 1038), GI:225314775 (SEQ ID NO: 1040), GI:359493559 (SEQ ID NO: 1041), GI:225451094 (SEQ ID NO: 1042), CeresAnnot:8657013 GI:242051064 (SEQ ID NO: 1044), (SEQ ID NO: 1045), GI:381218259 (SEQ ID NO: 1046), GI:357441531 (SEQ ID NO: 1047), (SEQ ID NO: 1048), GI:115467742 (SEQ ID NO: 1049), GI:357510077 (SEQ ID NO: 1050), GI:302823479 (SEQ ID NO: 1051), GI:357442625 (SEQ ID NO: 1052), GI:357498883 (SEQ ID NO: 1053), CeresClone:1911189 (SEQ ID NO: 1055), (SEQ ID NO: 1056), GI:356559967 (SEQ ID NO: 1057), (SEQ ID NO: 1058), GI:255574873 (SEQ ID NO: 1059), GI:225460002 (SEQ ID NO: 1060), (SEQ ID NO: 1061), GI:224056763 (SEQ ID NO: 1062), (SEQ ID NO: 1063), GI:297611539 (SEQ ID NO: 1064), CeresClone:1815446 (SEQ ID NO: 1066), GI:82697971 (SEQ ID NO: 1067), GI:255564916 (SEQ ID NO: 1068), (SEQ ID NO: 1069), GI:225459998 (SEQ ID NO: 1070), GI:169159268 (SEQ ID NO: 1071), GI:215261125 (SEQ ID NO: 1072), GI:356500238 (SEQ ID NO: 1073), (SEQ ID NO: 1074), CeresClone:1448852 (SEQ ID NO: 1076), GI:326532822 (SEQ ID NO: 1077), CeresClone:1991076 (SEQ ID NO: 1079), GI:326497909 (SEQ ID NO: 1080), GI:242068027 CeresAnnot:8684742 (SEQ ID NO: 1082), GI:225463175 (SEQ ID NO: 1083), (SEQ ID NO: 1084), GI:357498903 (SEQ ID NO: 1085), GI:125555059 (SEQ ID NO: 1086), GI:357133715_Bradi2g25600 (SEQ ID NO: 1087), CeresClone:892953 (SEQ ID NO: 1089), GI:226498284_CeresClone:330490 (SEQ ID NO: 1091), GI:169159266 (SEQ ID NO: 1092), GI:255564994 (SEQ ID NO: 1093), (SEQ ID NO: 1094), GI:15237783 (SEQ ID NO: 1095), GI:116781798 (SEQ ID NO: 1096), GI:380040722 (SEQ ID NO: 1097), CeresAnnot:1442123 (SEQ ID NO: 1099), GI:356504896 (SEQ ID NO: 1100), GI:356559969 (SEQ ID NO: 1101), (SEQ ID NO: 1102), CeresAnnot:8657010 (SEQ ID NO: 1104), GI:357152486 (SEQ ID NO: 1105), GI:357498895 (SEQ ID NO: 1106), CeresClone:1996207 (SEQ ID NO: 1108), GI:226504948_CeresClone:335133 (SEQ ID NO: 1110), GI:357116047 (SEQ ID NO: 1111), CeresClone:625081 (SEQ ID NO: 1113), (SEQ ID NO: 1114), GI:147820116 (SEQ ID NO: 1115), GI:380040720 (SEQ ID NO: 1116), GI:329756574 (SEQ ID NO: 1117), GI:225316828 (SEQ ID NO: 1119), GI:218185506 (SEQ ID NO: 1120), GI:302769530 (SEQ ID NO: 1121), GI:357152492 (SEQ ID NO: 1122), (SEQ ID NO: 1123), (SEQ ID NO: 1124), GI:168029383 (SEQ ID NO: 1125), GI:125559371 (SEQ ID NO: 1126), GI:357498899 (SEQ ID NO: 1127), GI:357116242 (SEQ ID NO: 1128), GI:380040724 (SEQ ID NO: 1129), (SEQ ID NO: 1130), GI:297812501 (SEQ ID NO: 1131), GI:210144144 (SEQ ID NO: 1133), CeresClone: 568611 (SEQ ID NO: 1135), GI:326527329 (SEQ ID NO: 1136), CeresAnnot:1483390 (SEQ ID NO: 1138), and GI:255553969 (SEQ ID NO: 1139). In some cases, a functional homolog of SEQ ID NO: 99 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 99. In some cases, a functional homolog of SEQ ID NO: 99 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 99 described above or set forth in the Sequence Listing.

Examples of amino acid sequences of functional homologs of the polypeptide set forth in SEQ ID NO: 188 are provided in FIG. 3 and in the Sequence Listing. Such functional homologs include, for example, GI_2569938 (SEQ ID NO: 189), GI_66816765 (SEQ ID NO: 190), GI_282759334 (SEQ ID NO: 191), CeresClone_1884375 (SEQ ID NO: 193), GI_75207626 (SEQ ID NO: 194), GI_115184057 (SEQ ID NO: 195), GI_225451399 (SEQ ID NO: 196), GI_20257430 (SEQ ID NO: 197), GI_20257459 (SEQ ID NO: 198), GI_20257428 (SEQ ID NO: 199), CeresClone_1776298 (SEQ ID NO: 201), GI_75161835 (SEQ ID NO: 202), GI_204022232 (SEQ ID NO: 203), GI_20257432 (SEQ ID NO: 204), GI_225424291 (SEQ ID NO: 205), GI_20257447 (SEQ ID NO: 206), GI_70797560 (SEQ ID NO: 207), GI_15219630 (SEQ ID NO: 208), GI_225457448 (SEQ ID NO: 209), CeresAnnot_1502385 (SEQ ID NO: 211), CeresClone_1809677 (SEQ ID NO: 213), CeresAnnot_8633163 (SEQ ID NO: 215), GI_302786358 (SEQ ID NO: 216), GI_204022230 (SEQ ID NO: 217), CeresAnnot_1463794 (SEQ ID NO: 219), GI_296804670 (SEQ ID NO: 220), GI_59800349 (SEQ ID NO: 221), GI_75121087 (SEQ ID NO: 222), CeresAnnot_870628 (SEQ ID NO: 224), GI_219964535 (SEQ ID NO: 225), GI_113171199 (SEQ ID NO: 226), CeresClone_1945971 (SEQ ID NO: 228), CeresAnnot_1440830 (SEQ ID NO: 230), GI_238821220 (SEQ ID NO: 231), GI_257219873 (SEQ ID NO: 232), GI_113206404 (SEQ ID NO: 233), CeresAnnot_1445496 (SEQ ID NO: 235), GI_147812753 (SEQ ID NO: 236), CeresAnnot_857982 (SEQ ID NO: 238), GI_255586838 (SEQ ID NO: 239), GI_15237971 (SEQ ID NO: 240), GI_20257436 (SEQ ID NO: 241), GI_225424293 (SEQ ID NO: 242), GI_297844400 (SEQ ID NO: 243), GI_75104298 (SEQ ID NO: 244), GI_148189864 (SEQ ID NO: 245), CeresClone_1884754 (SEQ ID NO: 247), GI_264688602 (SEQ ID NO: 248), GI_219886839 (SEQ ID NO: 249), GI_222154139 (SEQ ID NO: 250), GI_20257420 (SEQ ID NO: 251), GI_119214959 (SEQ ID NO: 252), GI_119214959 (SEQ ID NO: 254), GI_75104297 (SEQ ID NO: 255), GI_66816755 (SEQ ID NO: 256), GI_238821222 (SEQ ID NO: 257), GI_26451075 (SEQ ID NO: 258), GI_152968454 (SEQ ID NO: 259), GI_75121086 (SEQ ID NO: 260), GI_242058173 (SEQ ID NO: 261), GI_225451401 (SEQ ID NO: 262), CeresAnnot_832619 (SEQ ID NO: 264), GI_171702837 (SEQ ID NO: 265), GI_75148243 (SEQ ID NO: 266), GI_20257457 (SEQ ID NO: 267), GI_20257422 (SEQ ID NO: 268), GI_312281569 (SEQ ID NO: 269), GI_125545440 (SEQ ID NO: 270), CeresAnnot_1449379 (SEQ ID NO: 272), GI_290988843 (SEQ ID NO: 273), GI_224032153 (SEQ ID NO: 274), GI_225451515 (SEQ ID NO: 275), GI_339779229 (SEQ ID NO: 276), GI_75146039 (SEQ ID NO: 277), GI_115184074 (SEQ ID NO: 278), GI_321442634 (SEQ ID NO: 279), GI_63054405 (SEQ ID NO: 280), CeresClone_479467 (SEQ ID NO: 282), GI_75207630 (SEQ ID NO: 283), GI_297817754 (SEQ ID NO: 284), GI_2339978 (SEQ ID NO: 285), GI_66816747 (SEQ ID NO: 286), GI:119713908 (SEQ ID NO: 1009), GI:15866400 (SEQ ID NO: 1010), GI:20257442 (SEQ ID NO: 1011), GI:380504012 (SEQ ID NO: 1012), GI:380503998 (SEQ ID NO: 1013), GI:380504056 (SEQ ID NO: 1014), GI:15866316 (SEQ ID NO: 1015), GI:20257440 (SEQ ID NO: 1016), GI:20257463 (SEQ ID NO: 1017), GI:20257451 (SEQ ID NO: 1018), GI:380503968 (SEQ ID NO: 1019), GI:15866328 (SEQ ID NO: 1020), GI:15866334 (SEQ ID NO: 1021), GI:15866348 (SEQ ID NO: 1022), and GI:157154012 (SEQ ID NO: 1023). In some cases, a functional homolog of SEQ ID NO: 188 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 188. In some cases, a functional homolog of SEQ ID NO: 188 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 188 described above or set forth in the Sequence Listing.

Examples of amino acid sequences of functional homologs of the polypeptide set forth in SEQ ID NO: 1 are provided in FIG. 4 and in the Sequence Listing. Such functional homologs include, for example, GI_49065952 (SEQ ID NO: 2), GI_157683561 (SEQ ID NO: 3), GI_291586147 (SEQ ID NO: 4), CeresAnnot_8658260 (SEQ ID NO: 6), CeresClone_1784588 (SEQ ID NO: 8), GI_15005015 (SEQ ID NO: 9), GI_194700302 (SEQ ID NO: 10), GI_188035730 (SEQ ID NO: 11), GI_147852208 (SEQ ID NO: 12), GI_61651585 (SEQ ID NO: 13), GI_109729785 (SEQ ID NO: 14), GI_190192212 (SEQ ID NO: 15), GI_6691485 (SEQ ID NO: 16), GI_145206857 (SEQ ID NO: 17), GI_225421147 (SEQ ID NO: 18), GI_27261175 (SEQ ID NO: 19), GI_2316018 (SEQ ID NO: 20), GI_77632798 (SEQ ID NO: 21), GI_302811181 (SEQ ID NO: 22), GI_20149245 (SEQ ID NO: 23), GI_15004943 (SEQ ID NO: 24), GI_297849984 (SEQ ID NO: 25), GI_145206861 (SEQ ID NO: 26), GI_225421145 (SEQ ID NO: 27), GI_2289032 (SEQ ID NO: 28), GI_27123661 (SEQ ID NO: 29), GI_49065950 (SEQ ID NO: 30), GI_226508364 (SEQ ID NO: 31), GI_312197436 (SEQ ID NO: 32), GI_218196191 (SEQ ID NO: 33), CeresClone_1045013 (SEQ ID NO: 35), GI_134303282 (SEQ ID NO: 36), GI_14780049 (SEQ ID NO: 37), GI_340796369 (SEQ ID NO: 38), GI_4164147 (SEQ ID NO: 39), GI_9971221 (SEQ ID NO: 40), GI_3982753 (SEQ ID NO: 41), GI_85540947 (SEQ ID NO: 42), CeresAnnot_8725416 (SEQ ID NO: 44), GI_50428333 (SEQ ID NO: 45), GI_50428331 (SEQ ID NO: 46), GI_340796371 (SEQ ID NO: 47), GI_219887767 (SEQ ID NO: 48), GI_15418962 (SEQ ID NO: 49), GI_320462776 (SEQ ID NO: 50), GI_225430186 (SEQ ID NO: 51), GI_2314805 (SEQ ID NO: 52), GI_224070877 (SEQ ID NO: 53), GI_50428329 (SEQ ID NO: 54), GI_297743334 (SEQ ID NO: 55), GI_8247213 (SEQ ID NO: 56), GI_255040357 (SEQ ID NO: 57), GI_297839907 (SEQ ID NO: 58), GI_8894936 (SEQ ID NO: 59), GI_114329242 (SEQ ID NO: 60), GI_304636271 (SEQ ID NO: 61), GI_4164145 (SEQ ID NO: 62), GI_255549086 (SEQ ID NO: 63), GI_224141841 (SEQ ID NO: 64), GI_194459446 (SEQ ID NO: 65), sp_Q39103_G3OX1_ARATH (SEQ ID NO: 66), GI_85540946 (SEQ ID NO: 67), CeresClone_442759 (SEQ ID NO: 69), GI_115462397 (SEQ ID NO: 70), GI_190192214 (SEQ ID NO: 71), GI_304636273 (SEQ ID NO: 72), CeresClone_476411 (SEQ ID NO: 74), GI_2291080 (SEQ ID NO: 75), GI_304636275 (SEQ ID NO: 76), GI_255549006 (SEQ ID NO: 77), CeresClone_1653303 (SEQ ID NO: 79), CeresAnnot_1508682 (SEQ ID NO: 81), GI_294471308 (SEQ ID NO: 82), GI_3834350 (SEQ ID NO: 83), GI_2316102 (SEQ ID NO: 84), GI_11034551 (SEQ ID NO: 85), GI_15418964 (SEQ ID NO: 86), GI_71532877 (SEQ ID NO: 87), GI_40714039 (SEQ ID NO: 88), GI_3834352 (SEQ ID NO: 89), GI_255546615 (SEQ ID NO: 90), GI_38154346 (SEQ ID NO: 91), GI_145206859 (SEQ ID NO: 92), CeresAnnot_1438976 (SEQ ID NO: 94), GI_115434856 (SEQ ID NO: 95), sp_Q9ZT84_G3OX2_ARATH (SEQ ID NO: 96), GI_40714037 (SEQ ID NO: 97), GI_20149243 (SEQ ID NO: 98), CeresClone:1787734 (SEQ ID NO: 978), CeresClone:704370 (SEQ ID NO: 980), GI:357136088 (SEQ ID NO: 981), GI:326502098 (SEQ ID NO: 982), GI:357152716 (SEQ ID NO: 983), GI:242089739 (SEQ ID NO: 984), GI:225442751 (SEQ ID NO: 985), GI:357455059 (SEQ ID NO: 986), GI:365176184 (SEQ ID NO: 987), GI:356522371 (SEQ ID NO: 988), GI:356550578 (SEQ ID NO: 989), GI:357436835 (SEQ ID NO: 990), GI:356563832 (SEQ ID NO: 991), GI:297839909 (SEQ ID NO: 992), GI:356518262 (SEQ ID NO: 993), GI:301332976 (SEQ ID NO: 994), GI:301332946 (SEQ ID NO: 995), GI:301332982 (SEQ ID NO: 996), GI:301332866 (SEQ ID NO: 997), GI:301332872 (SEQ ID NO: 998), GI:356552539 (SEQ ID NO: 999), GI:301332918 (SEQ ID NO: 1000), GI:301332984 (SEQ ID NO: 1001), GI:301332974 (SEQ ID NO: 1002), GI:301332896 (SEQ ID NO: 1003), GI:301332906 (SEQ ID NO: 1004), GI:301333008 (SEQ ID NO: 1005), GI:116831381 (SEQ ID NO: 1006), GI:93007346 (SEQ ID NO: 1007), and GI:255552993 (SEQ ID NO: 1008). In some cases, a functional homolog of SEQ ID NO: 1 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1. In some cases, a functional homolog of SEQ ID NO: 1 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1 described above or set forth in the Sequence Listing.

Figure 5A:
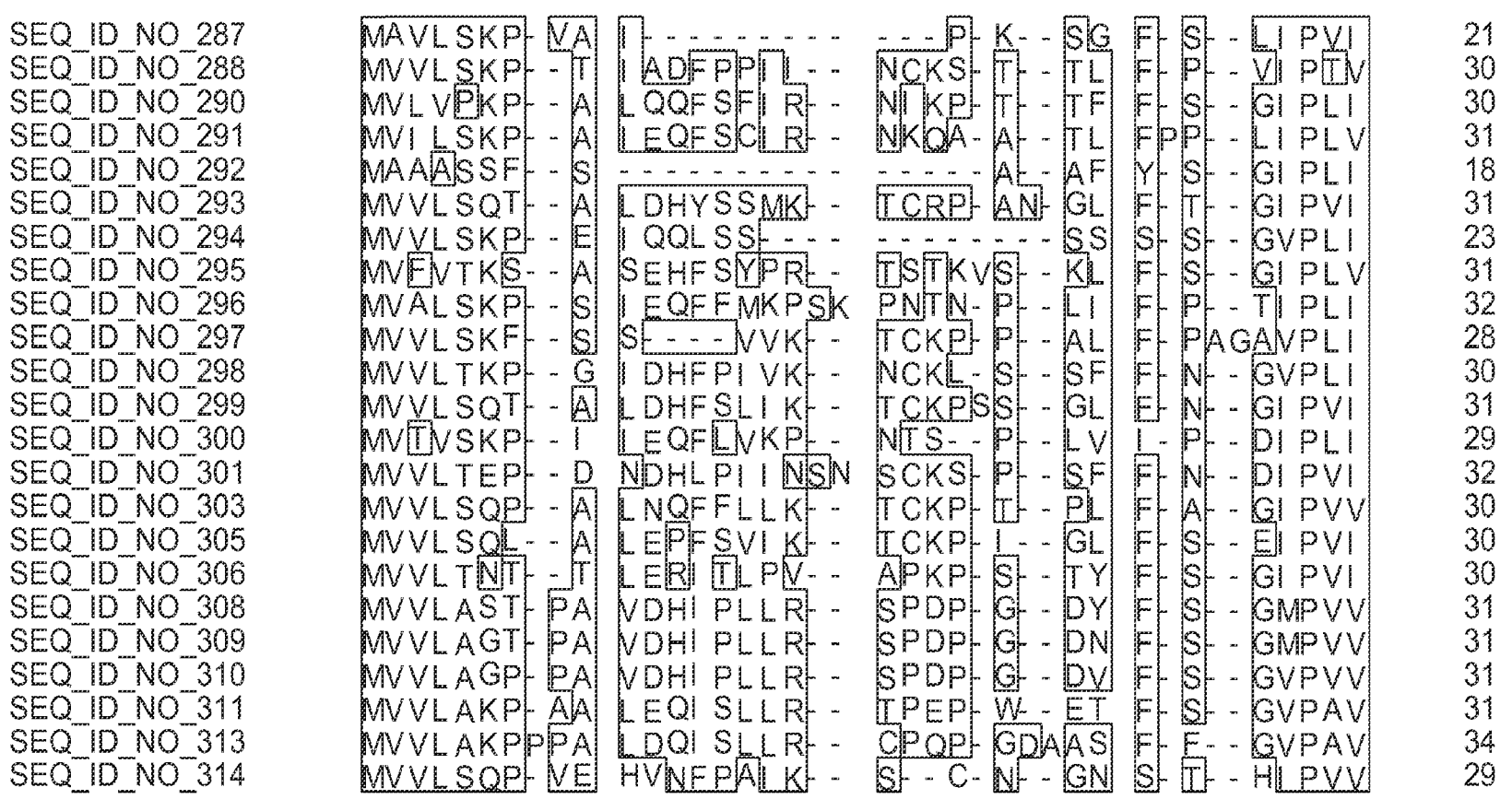
Figure 5D:
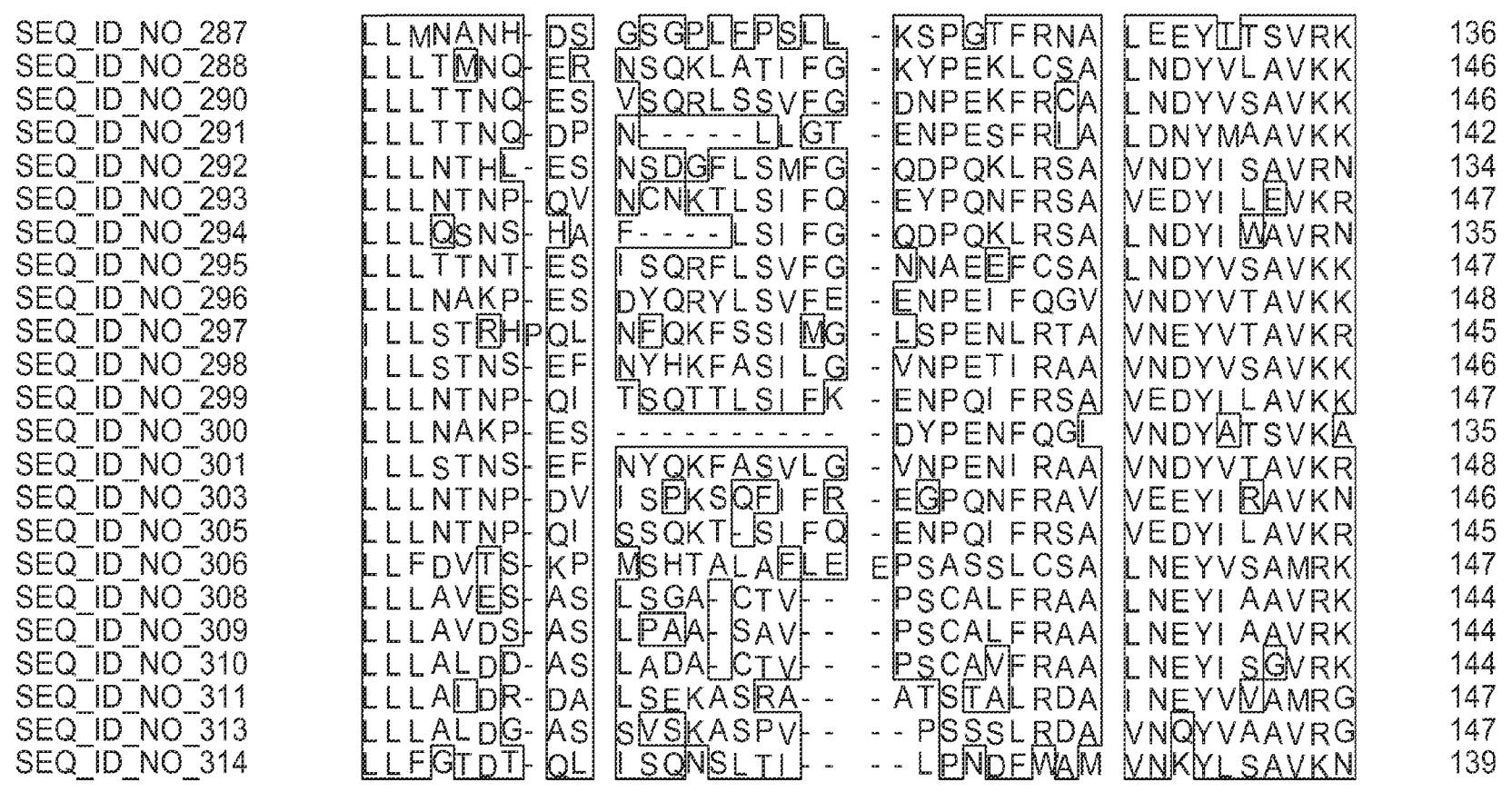
Figure 5E:
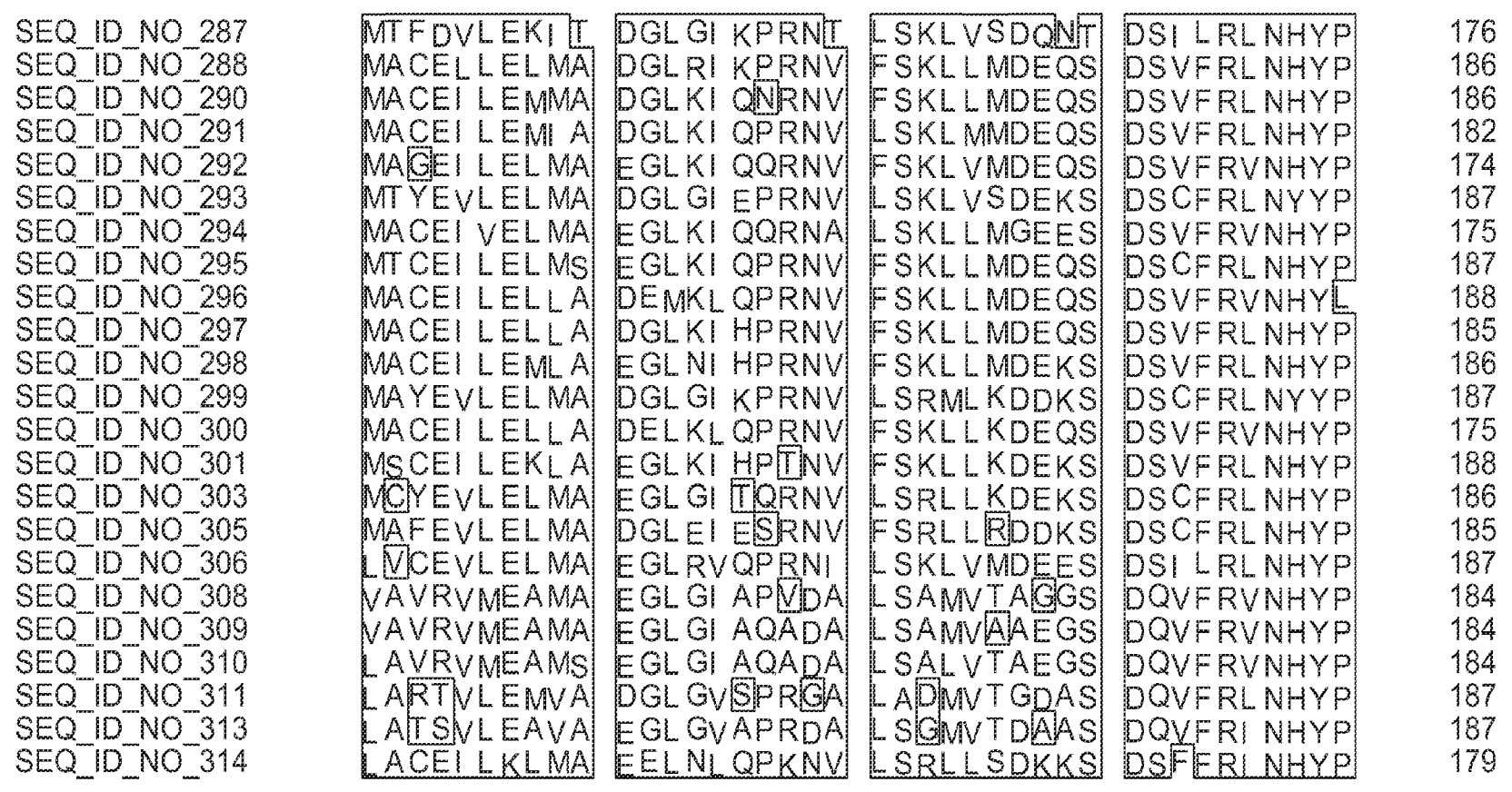

Examples of amino acid sequences of functional homologs of the polypeptide set forth in SEQ ID NO: 287 are provided in FIG. 5 and in the Sequence Listing. Such functional homologs include, for example, GI_147838135 (SEQ ID NO: 288), CeresAnnot_1466321 (SEQ ID NO: 290), GI_340796359 (SEQ ID NO: 291), GI_27123665 (SEQ ID NO: 292), GI_254935149 (SEQ ID NO: 293), GI_1666096 (SEQ ID NO: 294), GI_255040359 (SEQ ID NO: 295), GI_9971227 (SEQ ID NO: 296), GI_305677553 (SEQ ID NO: 297), GI_46849529 (SEQ ID NO: 298), GI_255557309 (SEQ ID NO: 299), GI_213032421 (SEQ ID NO: 300), GI_126843239 (SEQ ID NO: 301), CeresClone_572987 (SEQ ID NO: 303), CeresAnnot_1501920 (SEQ ID NO: 305), GI_192910888 (SEQ ID NO: 306), CeresClone_704889 (SEQ ID NO: 308), GI_326511994 (SEQ ID NO: 309), GI_125527760 (SEQ ID NO: 310), GI_84180617 (SEQ ID NO: 311), CeresAnnot_8733572 (SEQ ID NO: 313), GI_50428335 (SEQ ID NO: 314), GI_46576018 (SEQ ID NO: 315), GI_15221037 (SEQ ID NO: 316), GI_168044732 (SEQ ID NO: 317), CeresAnnot_8734027 (SEQ ID NO: 319), GI_67077820 (SEQ TD NO: 320), GI_67077812 (SEQ ID NO: 321), GI_212721130 (SEQ ID NO: 322), GI_49065954 (SEQ ID NO: 323), GI_320462780 (SEQ ID NO: 324), GI_297847044 (SEQ ID NO: 325), GI_190192216 (SEQ ID NO: 326), CeresAnnot_1497828 (SEQ ID NO: 328), GI_51011366 (SEQ ID NO: 329), GI_9971229 (SEQ ID NO: 330), CeresClone_615793 (SEQ ID NO: 332), GI_119477815 (SEQ ID NO: 333), GI_126843206 (SEQ ID NO: 334), GI_226505220 (SEQ ID NO: 335), GI_49035968 (SEQ ID NO: 336), GI_242057261 (SEQ ID NO: 337), GI_15226777 (SEQ ID NO: 338), GI_147838315 (SEQ ID NO: 339), GI_108755538 (SEQ ID NO: 340), GI_224064641 (SEQ ID NO: 341), GI_152003423 (SEQ ID NO: 342), CeresAnnot_1448918 (SEQ ID NO: 344), CeresClone_909614 (SEQ ID NO: 346), GI_297845928 (SEQ ID NO: 347), GI_225470621 (SEQ ID NO: 348), GI_115462223 (SEQ ID NO: 349), GI_327179117 (SEQ ID NO: 350), GI_15220645 (SEQ ID NO: 351), GI_327179119 (SEQ ID NO: 352), GI_6446413 (SEQ ID NO: 353), GI_297823239 (SEQ ID NO: 354), GI_27261179 (SEQ ID NO: 355), GI_49035760 (SEQ ID NO: 356), GI_297843038 (SEQ ID NO: 357), GI_168063557 (SEQ ID NO: 358), CeresClone_829454 (SEQ ID NO: 360), sp_Q9C6I4_G2OX7_ARATH (SEQ ID NO: 361), GI_125552976 (SEQ ID NO: 362), GI_79318890 (SEQ ID NO: 363), GI_60202574 (SEQ ID NO: 364), GI_67077818 (SEQ ID NO: 365), CeresClone_900331 (SEQ ID NO: 367), GI_222630276 (SEQ ID NO: 368), CeresAnnot_8657905 (SEQ ID NO: 370), GI_126843224 (SEQ ID NO: 371), CeresClone_313261 (SEQ ID NO: 373), GI_32127337 (SEQ ID NO: 374), GI_51011364 (SEQ ID NO: 375), GI_330752217 (SEQ ID NO: 376), sp_O49561_G2OX8_ARATH (SEQ ID NO: 377), GI_251821339 (SEQ ID NO: 378), GI_37544101 (SEQ ID NO: 379), GI_225432055 (SEQ ID NO: 380), CeresClone_1076347 (SEQ ID NO: 382), GI_46849531 (SEQ ID NO: 383), GI_225468310 (SEQ ID NO: 384), CeresAnnot_1441748 (SEQ ID NO: 386), GI_223953574 (SEQ ID NO: 387), GI_49035759 (SEQ ID NO: 388), GI_327179113 (SEQ ID NO: 389), CeresClone_1239118 (SEQ ID NO: 391), GI_125550923 (SEQ ID NO: 392), GI_326520938 (SEQ ID NO: 393), GI_297804032 (SEQ ID NO: 394), GI_27261177 (SEQ ID NO: 395), GI_312196334 (SEQ ID NO: 396), GI_23491590 (SEQ ID NO: 397), GI_168024874 (SEQ ID NO: 398), GI_261863286 (SEQ ID NO: 399), GI_134303284 (SEQ ID NO: 400), CeresClone_1856391 (SEQ ID NO: 402), GI_242054465 (SEQ ID NO: 403), GI_157382968 (SEQ ID NO: 404), GI_15217753 (SEQ ID NO: 405), GI_109729789 (SEQ ID NO: 406), GI_126843214 (SEQ ID NO: 407), GI_327179125 (SEQ ID NO: 408), GI_340796367 (SEQ ID NO: 409), GI_312195240 (SEQ ID NO: 410), CeresAnnot_1511928 (SEQ ID NO: 412), GI_226501026 (SEQ ID NO: 413), GI_224108798 (SEQ ID NO: 414), GI_119475961 (SEQ ID NO: 415), CeresClone_539037 (SEQ ID NO: 417), GI_50293061 (SEQ ID NO: 418), GI_50428337 (SEQ ID NO: 419), GI_225437645 (SEQ ID NO: 420), GI_115440025 (SEQ ID NO: 421), GI_326522773 (SEQ ID NO: 422), GI_218187724 (SEQ ID NO: 423), GI_340796363 (SEQ ID NO: 424), GI_67077816 (SEQ ID NO: 425), CeresClone_156482 (SEQ ID NO: 427), GI_340796365 (SEQ ID NO: 428), GI_242086999 (SEQ ID NO: 429), GI_226501846 (SEQ ID NO: 430), CeresAnnot_1444853 (SEQ ID NO: 432), GI_29825611 (SEQ ID NO: 433), GI_125572075 (SEQ ID NO: 434), GI_297842621 (SEQ ID NO: 435), GI_320462782 (SEQ ID NO: 436), GI_340796361 (SEQ ID NO: 437), GI_225443855 (SEQ ID NO: 438), CeresClone_1860822 (SEQ ID NO: 440), GI_126843218 (SEQ ID NO: 441), CeresClone_1831422 (SEQ ID NO: 443), GI_255548359 (SEQ ID NO: 444), GI_115465423 (SEQ ID NO: 445), GI_255644878 (SEQ ID NO: 446), GI_6478200 (SEQ ID NO: 447), CeresClone_1831239 (SEQ ID NO: 449), CeresClone_1918532 (SEQ ID NO: 451), GI_49065956 (SEQ ID NO: 452), GI_326532306 (SEQ ID NO: 453), GI_327179123 (SEQ ID NO: 454), CeresAnnot_1471538 (SEQ ID NO: 456), GI_284468804 (SEQ ID NO: 457), GI_67077814 (SEQ ID NO: 458), GI_224101511 (SEQ ID NO: 459), GI_87240601 (SEQ ID NO: 460), CeresClone_467671 (SEQ ID NO: 462), GI_134303286 (SEQ ID NO: 463), GI_109729791 (SEQ ID NO: 464), GI_338733586 (SEQ ID NO: 465), GI_125553301 (SEQ ID NO: 466), GI_116672836 (SEQ ID NO: 467), GI_327359295 (SEQ ID NO: 468), GI_297744020 (SEQ ID NO: 469), GI_93115317 (SEQ ID NO: 470), GI:124829 (SEQ ID NO: 1140), GI:7595984 (SEQ ID NO: 1141), GI:356571007 (SEQ ID NO: 1142), GI:357134283 (SEQ ID NO: 1143), GI:356660541 (SEQ ID NO: 1144), GI:218188130 (SEQ ID NO: 1145), GI:356558109 (SEQ ID NO: 1146), GI:365872403 (SEQ ID NO: 1147), GI:379749536 (SEQ ID NO: 1148), GI:6016387 (SEQ ID NO: 1149), GI:66735505 (SEQ ID NO: 1150), GI:356532490 (SEQ ID NO: 1151), GI:356533324 (SEQ ID NO: 1152), CeresClone:1724110 (SEQ ID NO: 1154), GI:171680612 (SEQ ID NO: 1155), GI:358380091 (SEQ ID NO: 1156), GI:357447293 (SEQ ID NO: 1157), GI:125532930 (SEQ ID NO: 1158), GI:357127374 (SEQ ID NO: 1159), GI:126724682 (SEQ ID NO: 1160), GI:53139660 (SEQ ID NO: 1161), GI:225555204 (SEQ ID NO: 1162), GI:14916565 (SEQ ID NO: 1163), GI:380851109 (SEQ ID NO: 1164), GI:222632219 (SEQ ID NO: 1165), GI:357128141 (SEQ ID NO: 1166), GI:356564662 (SEQ ID NO: 1167), GI:3779220 (SEQ ID NO: 1168), GI:113202132 (SEQ ID NO: 1169), GI:50261845 (SEQ ID NO: 1170), GI:356549549 (SEQ ID NO: 1171), GI:169631509 (SEQ ID NO: 1172), GI:114562664 (SEQ ID NO: 1173), GI:116783364 (SEQ ID NO: 1174), GI:116788048 (SEQ ID NO: 1175), GI:125575676 (SEQ ID NO: 1176), GI:225680969 (SEQ ID NO: 1177), CeresAnnot:8668753 (SEQ ID NO: 1179), GI:359473878 (SEQ ID NO: 1180), GI:357488573 (SEQ ID NO: 1181), GI:58269616 (SEQ ID NO: 1182), GI:365848372 (SEQ ID NO: 1183), GI:217385866 (SEQ ID NO: 1184), GI:342868843 (SEQ ID NO: 1185), GI:350637890 (SEQ ID NO: 1186), GI:259487966 (SEQ ID NO: 1187), GI:77360864 (SEQ ID NO: 1188), GI:350285025 (SEQ ID NO: 1189), CeresAnnot:550021 (SEQ ID NO: 1191), GI:126726302 (SEQ ID NO: 1192), GI:377560209 (SEQ ID NO: 1193), GI:356549099 (SEQ ID NO: 1194), GI:125569479 (SEQ ID NO: 1195), GI:145607820 (SEQ ID NO: 1196), GI:344231610 (SEQ ID NO: 1197), GI:224130932 (SEQ ID NO: 1198), GI:322693186 (SEQ ID NO: 1199), GI:37698286 (SEQ ID NO: 1200), CeresAnnot:1517584 (SEQ ID NO: 1202), CeresAnnot:8670458 (SEQ ID NO: 1204), GI:357448799 (SEQ ID NO: 1205), GI:154296822 (SEQ ID NO: 1206), CeresAnnot:1458668 (SEQ ID NO: 1208), GI:357117693 (SEQ ID NO: 1209), GI:1527191 (SEQ ID NO: 1210), GI:115442079 (SEQ ID NO: 1211), CeresAnnot:8725147 (SEQ ID NO: 1213), GI:357136506 (SEQ ID NO: 1214), GI:302759861 (SEQ ID NO: 1215), GI:168058603 (SEQ ID NO: 1216), GI:356510794 (SEQ ID NO: 1217), GI:159149180 (SEQ ID NO: 1218), GI:331700025 (SEQ ID NO: 1219), GI:117586718 (SEQ ID NO: 1220), GI:41323935 (SEQ ID NO: 1221), GI:297830340 (SEQ ID NO: 1222), GI:53792534 (SEQ ID NO: 1223), GI:54260396 (SEQ ID NO: 1224), GI:357128775 (SEQ ID NO: 1225), GI:327179115 (SEQ ID NO: 1226), GI:327306431 (SEQ ID NO: 1227), GI:356499745 (SEQ ID NO: 1228), GI:358368242 (SEQ ID NO: 1229), GI:254583526 (SEQ ID NO: 1230), GI:115435212 (SEQ ID NO: 1231), GI:255557479 (SEQ ID NO: 1232), GI:357476439 (SEQ ID NO: 1233), GI:356555146 (SEQ ID NO: 1234), GI:83033890 (SEQ ID NO: 1235), GI:358348748 (SEQ ID NO: 1236), GI:261251140 (SEQ ID NO: 1237), GI:297829900 (SEQ ID NO: 1238), GI:39950534 (SEQ ID NO: 1239), GI:356503948 (SEQ ID NO: 1240), GI:343794766 (SEQ ID NO: 1241), GI:347758670 (SEQ ID NO: 1242), GI:357488575 (SEQ ID NO: 1243), GI:7108579 (SEQ ID NO: 1244), GI:327348464 (SEQ ID NO: 1245), CeresAnnot:1464270 (SEQ ID NO: 1247), GI:169777699 (SEQ ID NO: 1248), GI:297803592 (SEQ ID NO: 1249), GI:357127376 (SEQ ID NO: 1250), GI:357128527 (SEQ ID NO: 1251), GI:357485645 (SEQ ID NO: 1252), CeresClone:387918 (SEQ ID NO: 1254), GI:363807830 (SEQ ID NO: 1255), GI:317031438 (SEQ ID NO: 1256), GI:326534020 (SEQ ID NO: 1257), GI:146292853 (SEQ ID NO: 1258), GI:343925590 (SEQ ID NO: 1259), GI:123906 (SEQ ID NO: 1260), GI:357129744 (SEQ ID NO: 1261), GI:356556910 (SEQ ID NO: 1262), GI:5579094 (SEQ ID NO: 1263), GI:86197901 (SEQ ID NO: 1264), CeresAnnot:8660515 (SEQ ID NO: 1266), GI:169781970 (SEQ ID NO: 1267), GI:357128523 (SEQ ID NO: 1268), GI:261363611 (SEQ ID NO: 1269), GI:356528126 (SEQ ID NO: 1270), GI:380448148 (SEQ ID NO: 1271), GI:125525840 (SEQ ID NO: 1272), and GI:327179111 (SEQ ID NO: 1273). In some cases, a functional homolog of SEQ ID NO: 287 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 287. In some cases, a functional homolog of SEQ ID NO: 287 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 287 described above or set forth in the Sequence Listing.

Examples of amino acid sequences of functional homologs of the polypeptide set forth in SEQ ID NO: 1429 are provided in FIG. 6 and in the Sequence Listing. Such functional homologs include, for example, GI:342877779 (SEQ ID NO: 1430), GI:197724593 (SEQ ID NO: 1431), GI:115334279 (SEQ ID NO: 1432), GI:310799037 (SEQ ID NO: 1433), GI:302893705 (SEQ ID NO: 1434), GI:85110002 (SEQ ID NO: 1435), GI:169783174 (SEQ ID NO: 1436), GI:242815592 (SEQ ID NO: 1437), GI:336468679 (SEQ ID NO: 1438), GI:255956889 (SEQ ID NO: 1439), GI:346970804 (SEQ ID NO: 1440), GI:315047883 (SEQ ID NO: 1441), GI:239609926 (SEQ ID NO: 1442), GI:310799765 (SEQ ID NO: 1443), GI:322697028 (SEQ ID NO: 1444), GI:351639827 (SEQ ID NO: 1445), GI:310801951 (SEQ ID NO: 1446), GI:317035847 (SEQ ID NO: 1447), GI:317033079 (SEQ ID NO: 1448), GI:39975659 (SEQ ID NO: 1449), GI:312212422 (SEQ ID NO: 1450), GI:145606901 (SEQ ID NO: 1451), GI:336263834 (SEQ ID NO: 1452), GI:350636399 (SEQ ID NO: 1453), GI:119485937 (SEQ ID NO: 1454), GI:46118584 (SEQ ID NO: 1455), GI:116203015 (SEQ ID NO: 1456), GI:351648588 (SEQ ID NO: 1457), GI:327350850 (SEQ ID NO: 1458), GI:134082570 (SEQ ID NO: 1459), GI:238507153 (SEQ ID NO: 1460), GI:350631552 (SEQ ID NO: 1461), GI:261198797 (SEQ ID NO: 1462), GI:351640230 (SEQ ID NO: 1463), GI:342887718 (SEQ ID NO: 1464), GI:115391085 (SEQ ID NO: 1465), GI:255950818 (SEQ ID NO: 1466), GI:67903086 (SEQ ID NO: 1467), GI:346973227 (SEQ ID NO: 1468), GI:310791795 (SEQ ID NO: 1469), GI:46111581 (SEQ ID NO: 1470), GI:302912247 (SEQ ID NO: 1471), GI:302890983 (SEQ ID NO: 1472), GI:325095532 (SEQ ID NO: 1473), GI:310801736 (SEQ ID NO: 1474), GI:169786189 (SEQ ID NO: 1475), GI:322704477 (SEQ ID NO: 1476), GI:296809607 (SEQ ID NO: 1477), GI:358384333 (SEQ ID NO: 1478), GI:380486688 (SEQ ID NO: 1479), GI:380485723 (SEQ ID NO: 1480), GI:380493657 (SEQ ID NO: 1481), GI:310801960 (SEQ ID NO: 1482), GI:380493536 (SEQ ID NO: 1483), GI:380485117 (SEQ ID NO: 1484), GI:367046496 (SEQ ID NO: 1485), GI:358378098 (SEQ ID NO: 1486), GI:328671361 (SEQ ID NO: 1487), GI:328671376 (SEQ ID NO: 1488), GI:328671358 (SEQ ID NO: 1489), GI:328671355 (SEQ ID NO: 1490), GI:342883913 (SEQ ID NO: 1491), GI:328671364 (SEQ ID NO: 1492), GI:27368044 (SEQ ID NO: 1493), GI:242800740 (SEQ ID NO: 1494), GI:15054396 (SEQ ID NO: 1495), GI:351648133 (SEQ ID NO: 1496), GI:28975428 (SEQ ID NO: 1497), GI:380471186 (SEQ ID NO: 1498), GI:270160636 (SEQ ID NO: 1499), GI:326482954 (SEQ ID NO: 1500), GI:115385677 (SEQ ID NO: 1501), GI:351649667 (SEQ ID NO: 1502), GI:358369247 (SEQ ID NO: 1503), GI:39969835 (SEQ ID NO: 1504), GI:327309580 (SEQ ID NO: 1505), GI:169612674 (SEQ ID NO: 1506), GI:269856265 (SEQ ID NO: 1507), GI:269978413 (SEQ ID NO: 1508), GI:270160664 (SEQ ID NO: 1509), GI:346325649 (SEQ ID NO: 1510), GI:134079537 (SEQ ID NO: 1511), GI:46102962 (SEQ ID NO: 1512), GI:270160658 (SEQ ID NO: 1513), GI:270160632 (SEQ ID NO: 1514), GI:270160623 (SEQ ID NO: 1515), GI:145606494 (SEQ ID NO: 1516), GI:358367412 (SEQ ID NO: 1517), GI:270160641 (SEQ ID NO: 1518), GI:270160627 (SEQ ID NO: 1519), GI:358372883 (SEQ ID NO: 1520), GI:339469697 (SEQ ID NO: 1521), GI:270160647 (SEQ ID NO: 1522), GI:380479505 (SEQ ID NO: 1523), GI:169769747 (SEQ ID NO: 1524), GI:212536382 (SEQ ID NO: 1525), GI:310800499 (SEQ ID NO: 1526), GI:310801547 (SEQ ID NO: 1527), GI:115398866 (SEQ ID NO: 1528), GI:146324413 (SEQ ID NO: 1529), GI:159124267 (SEQ ID NO: 1530), GI:317032179 (SEQ ID NO: 1531), GI:121699333 (SEQ ID NO: 1532), GI:134078874 (SEQ ID NO: 1533), GI:242795502 (SEQ ID NO: 1534), GI:71002914 (SEQ ID NO: 1535), GI:380473273 (SEQ ID NO: 1536), GI:255948452 (SEQ ID NO: 1537), GI:302500503 (SEQ ID NO: 1538), GI:121714683 (SEQ ID NO: 1539), GI:23574644 (SEQ ID NO: 1540), and GI:339469460 (SEQ ID NO: 1541). In some cases, a functional homolog of SEQ ID NO: 1429 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1429. In some cases, a functional homolog of SEQ ID NO: 1429 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1429 described above or set forth in the Sequence Listing.

Examples of amino acid sequences of functional homologs of the polypeptide set forth in SEQ ID NO: 1542 are provided in FIG. 7 and in the Sequence Listing. Such functional homologs include, for example, GI:42661490 (SEQ ID NO: 1543), GI:211970313 (SEQ ID NO: 1544), GI:342877776 (SEQ ID NO: 1545), GI:350295800 (SEQ ID NO: 1546), GI:46139765 (SEQ ID NO: 1547), GI:242809430 (SEQ ID NO: 1548), GI:169619475 (SEQ ID NO: 1549), GI:339467588 (SEQ ID NO: 1550), GI:380495415 (SEQ ID NO: 1551), GI:255955071 (SEQ ID NO: 1552), GI:322704192 (SEQ ID NO: 1553), GI:367036275 (SEQ ID NO: 1554), GI:378732306 (SEQ ID NO: 1555), GI:238497964 (SEQ ID NO: 1556), GI:296803841 (SEQ ID NO: 1557), GI:378731760 (SEQ ID NO: 1558), GI:322696305 (SEQ ID NO: 1559), GI:310795092 (SEQ ID NO: 1560), GI:317141690 (SEQ ID NO: 1561), GI:156043835 (SEQ ID NO: 1562), GI:346978982 (SEQ ID NO: 1563), GI:380482210 (SEQ ID NO: 1564), GI:212545757 (SEQ ID NO: 1565), GI:115399682 (SEQ ID NO: 1566), and GI:302417990 (SEQ ID NO: 1567). In some cases, a functional homolog of SEQ ID NO: 1542 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1542. In some cases, a functional homolog of SEQ ID NO: 1542 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1542 described above or set forth in the Sequence Listing.

Examples of amino acid sequences of functional homologs of the polypeptide set forth in SEQ ID NO: 1386 are provided in FIG. 8 and in the Sequence Listing. Such functional homologs include, for example, GI:122938156 (SEQ ID NO: 1387), GI:240282093 (SEQ ID NO: 1388), GI:3549879 (SEQ ID NO: 1389), GI:380486272 (SEQ ID NO: 1390), (SEQ ID NO: 1391), GI:317030883 (SEQ ID NO: 1392), GI:239614263 (SEQ ID NO: 1393), GI:270160669 (SEQ ID NO: 1394), GI:119469260 (SEQ ID NO: 1395), GI:242795506 (SEQ ID NO: 1396), GI:226291700 (SEQ ID NO: 1397), GI:4959945 (SEQ ID NO: 1398), GI:74275563 (SEQ ID NO: 1399), (SEQ ID NO: 1400), GI:159124063 (SEQ ID NO: 1401), GI:367035976 (SEQ ID NO: 1402), GI:159130277 (SEQ ID NO: 1403), GI:67904522 (SEQ ID NO: 1404), (SEQ ID NO: 1405), GI:225679929 (SEQ ID NO: 1406), GI:67902304 (SEQ ID NO: 1407), GI:342877778 (SEQ ID NO: 1408), GI:295667161 (SEQ ID NO: 1409), GI:270160618 (SEQ ID NO: 1410), GI:134076920 (SEQ ID NO: 1411), (SEQ ID NO: 1412), GI:302423784 (SEQ ID NO: 1413), GI:270160651 (SEQ ID NO: 1414), GI:197724589 (SEQ ID NO: 1415), GI:269978406 (SEQ ID NO: 1416), GI:115385431 (SEQ ID NO: 1417), GI:302657172 (SEQ ID NO: 1418), GI:380480560 (SEQ ID NO: 1419), GI:146324548 (SEQ ID NO: 1420), GI:339469066 (SEQ ID NO: 1421), GI:154273751 (SEQ ID NO: 1422), GI:145616804 (SEQ ID NO: 1423), (SEQ ID NO: 1424), GI:328671370 (SEQ ID NO: 1425), GI:350629557 (SEQ ID NO: 1426), GI:261204397 (SEQ ID NO: 1427), and GI:255939330 (SEQ ID NO: 1428). In some cases, a functional homolog of SEQ ID NO: 1386 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1386. In some cases, a functional homolog of SEQ ID NO: 1386 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1386 described above or set forth in the Sequence Listing.

Figure 9A:
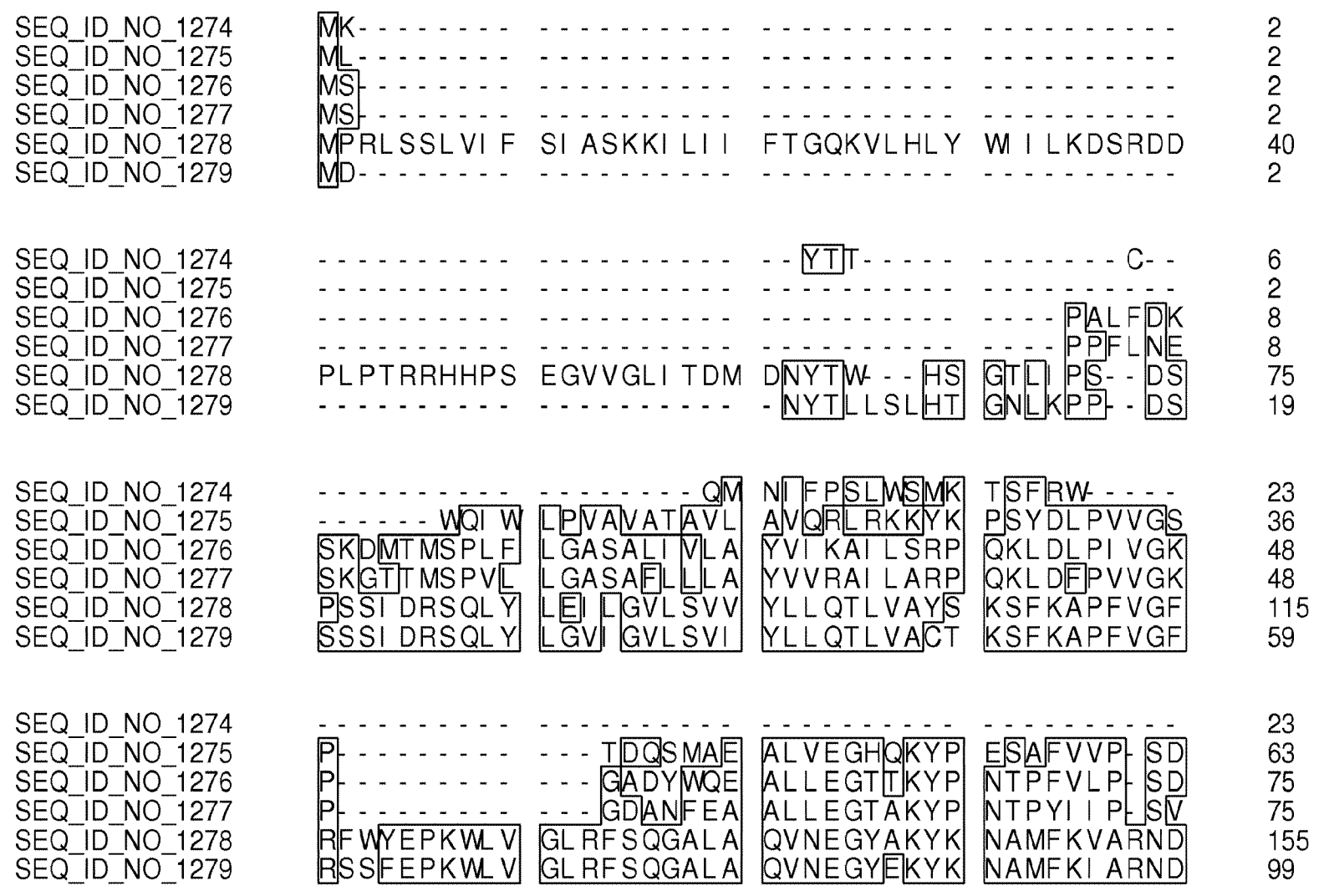

Examples of amino acid sequences of functional homologs of the polypeptide set forth in SEQ ID NO: 1274 are provided in FIG. 9 and in the Sequence Listing. Such functional homologs include, for example, GI:310790427 (SEQ ID NO: 1275), GI:347831214 (SEQ ID NO: 1276), GI:156047892 (SEQ ID NO: 1277), GI:67522282 (SEQ ID NO: 1278), GI:119494789 (SEQ ID NO: 1279), GI:212539424 (SEQ ID NO: 1280), GI:327343381 (SEQ ID NO: 1281), GI:302404826 (SEQ ID NO: 1282), GI:326484980 (SEQ ID NO: 1283), GI:358384361 (SEQ ID NO: 1284), GI:242804557 (SEQ ID NO: 1285), GI:346979790 (SEQ ID NO: 1286), GI:258578343 (SEQ ID NO: 1287), GI:326483893 (SEQ ID NO: 1288), GI:212542733 (SEQ ID NO: 1289), GI:367032834 (SEQ ID NO: 1290), GI:326470143 (SEQ ID NO: 1291), GI:164428375 (SEQ ID NO: 1292), GI:342886866 (SEQ ID NO: 1293), GI:270124461 (SEQ ID NO: 1294), GI:299744611 (SEQ ID NO: 1295), GI:320036821 (SEQ ID NO: 1296), GI:327343267 (SEQ ID NO: 1297), GI:302890139 (SEQ ID NO: 1298), GI:315039401 (SEQ ID NO: 1299), GI:74691493 (SEQ ID NO: 1300), GI:350631590 (SEQ ID NO: 1301), GI:46109972 (SEQ ID NO: 1302), GI:302502806 (SEQ ID NO: 1303), GI:327292707 (SEQ ID NO: 1304), GI:353240577 (SEQ ID NO: 1305), GI:326484981 (SEQ ID NO: 1306), GI:296416849 (SEQ ID NO: 1307), GI:119186083 (SEQ ID NO: 1308), GI:296818735 (SEQ ID NO: 1309), GI:342877777 (SEQ ID NO: 1310), GI:70992027 (SEQ ID NO: 1311), GI:315040165 (SEQ ID NO: 1312), GI:296420744 (SEQ ID NO: 1313), GI:336371322 (SEQ ID NO: 1314), GI:115390288 (SEQ ID NO: 1315), GI:299740695 (SEQ ID NO: 1316), GI:296818393 (SEQ ID NO: 1317), GI:74676162 (SEQ ID NO: 1318), GI:326475322 (SEQ ID NO: 1319), GI:312212946 (SEQ ID NO: 1320), GI:62318475 (SEQ ID NO: 1321), GI:296422933 (SEQ ID NO: 1322), GI:361126544 (SEQ ID NO: 1323), GI:238487930 (SEQ ID NO: 1324), GI:341599458 (SEQ ID NO: 1325), GI:336369617 (SEQ ID NO: 1326), GI:339475687 (SEQ ID NO: 1327), GI:327343373 (SEQ ID NO: 1328), GI:327343325 (SEQ ID NO: 1329), GI:336365283 (SEQ ID NO: 1330), GI:303318042 (SEQ ID NO: 1331), GI:336382397 (SEQ ID NO: 1332), GI:378728369 (SEQ ID NO: 1333), GI:255955605 (SEQ ID NO: 1334), GI:380489258 (SEQ ID NO: 1335), GI:358389174 (SEQ ID NO: 1336), GI:14278967 (SEQ ID NO: 1337), GI:322705205 (SEQ ID NO: 1338), GI:354952198 (SEQ ID NO: 1339), GI:154289961 (SEQ ID NO: 1340), GI:154290109 (SEQ ID NO: 1341), GI:211970315 (SEQ ID NO: 1342), GI:380481111 (SEQ ID NO: 1343), GI:302897901 (SEQ ID NO: 1344), GI:169635726 (SEQ ID NO: 1345), GI:367046821 (SEQ ID NO: 1346), GI:354961647 (SEQ ID NO: 1347), GI:171679136 (SEQ ID NO: 1348), (SEQ ID NO: 1349), GI:145254738 (SEQ ID NO: 1350), GI:327292709 (SEQ ID NO: 1351), GI:170109428 (SEQ ID NO: 1352), GI:340521233 (SEQ ID NO: 1353), GI:302502804 (SEQ ID NO: 1354), GI:350630566 (SEQ ID NO: 1355), GI:320586089 (SEQ ID NO: 1356), GI:326475321 (SEQ ID NO: 1357), GI:380490852 (SEQ ID NO: 1358), GI:330928050 (SEQ ID NO: 1359), GI:302690250 (SEQ ID NO: 1360), GI:350631043 (SEQ ID NO: 1361), GI:255931839 (SEQ ID NO: 1362), GI:336466767 (SEQ ID NO: 1363), GI:328796058 (SEQ ID NO: 1364), GI:296420105 (SEQ ID NO: 1365), GI:302667711 (SEQ ID NO: 1366), GI:351642318 (SEQ ID NO: 1367), GI:119470770 (SEQ ID NO: 1368), GI:340514420 (SEQ ID NO: 1369), GI:56609350 (SEQ ID NO: 1370), GI:367046496 (SEQ ID NO: 1371), GI:121718870 (SEQ ID NO: 1372), GI:240274084 (SEQ ID NO: 1373), GI:154290200 (SEQ ID NO: 1374), GI:302693088 (SEQ ID NO: 1375), GI:296804446 (SEQ ID NO: 1376), GI:302682570 (SEQ ID NO: 1377), GI:156045924 (SEQ ID NO: 1378), GI:336377080 (SEQ ID NO: 1379), GI:336365177 (SEQ ID NO: 1380), GI:156045918 (SEQ ID NO: 1381), GI:116178810 (SEQ ID NO: 1382), GI:169609220 (SEQ ID NO: 1383), GI:347829721 (SEQ ID NO: 1384), and GI:159124430 (SEQ ID NO: 1385). In some cases, a functional homolog of SEQ ID NO: 1274 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1274. In some cases, a functional homolog of SEQ ID NO: 1274 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1274 described above or set forth in the Sequence Listing.

The identification of conserved regions in a biomass composition-modulating polypeptide facilitates production of variants of biomass composition-modulating polypeptides. Variants of biomass composition-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, FIG. 4, FIG. 5, FIG. 6, FIG. 7, FIG. 8, or FIG. 9, and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful biomass composition-modulating polypeptides include those that fit a Hidden Markov Model based on the polypeptides set forth in any one of FIGS. 1-9. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMer 3.0 with default program parameters, using the sequences of the group of functional homologs as input. In some instances, the input files can be in FASTA format. HMMer is provided by the Howard Hughes Medical Institute (http://hmmeer.janelia.org).

The multiple sequence alignment is generated by Prob-Cons (Do et al., *Genome Res.*, 15(2):330-40 (2005)) version 1.12 using default parameters: ProbCons is a public domain software program. ProbCons and HMMer can be found on the world wide web at fr.com/probcons/.

The HMM for a group of functional homologs can be used to determine the likelihood that a candidate biomass composition-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMer hmmsearch program. The following parameter is used when running hmmsearch: the E-value cutoff for reporting is set to 1 ("-E 1"). A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The biomass composition-modulating polypeptides discussed below fit the indicated HMM with an HMM bit score greater than to 65 (e.g., greater than 70, 80, 90, 100, 120, 140, 200, 300, 500, 1000, 1500, or 2000). In some embodiments, the HMM bit score of a biomass composition-modulating polypeptide discussed below is about 50%, 60%, 70%, 80%, 90%, or 95% of the HMM bit score of a functional homolog provided in the Sequence Listing of this application. In some embodiments, a biomass composition-modulating polypeptide discussed below fits the indicated HMM with an HMM bit score greater than 210, and has a domain indicative of a biomass composition-modulating polypeptide. In some embodiments, a biomass composition-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-9.

Examples of polypeptides are shown in the sequence listing that have HMM bit scores greater than 65 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 620, 640, 660, 680, 700, 710, 720, or 730) when fitted to an HMM generated from the amino acid sequences set forth in FIG. 1 are identified in the Sequence Listing of this application. Such polypeptides include, for example, SEQ ID NOs: 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, and 976.

Examples of polypeptides are shown in the sequence listing that have HMM bit scores greater than 199 (e.g., greater than 200, 210, 220, 230, 240, 250, 260, 270, 280, 290, 300, 320, 340, 260, 380, 400, 420, 440, 460, 480, 500, 520, 540, 560, 580, 600, 620, 640, 660, 680, or 690) when fitted to an HMM generated from the amino acid sequences set forth in FIG. 2 are identified in the Sequence Listing of this application. Such polypeptides include, for example, SEQ ID NOs: 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, and 1139.

Examples of polypeptides are shown in the sequence listing that have HMM bit scores greater than 303 (e.g., greater than 310, 320, 340, 260, 380, 400, 420, 440, 460, 480, 500, 520, 540, 560, 580, 600, 620, 640, 660, 680, 700, 725, 750, 775, 800, 825, 850, 875, 900, 925, 950, 975, 1000, 1025, 1050, 1075, 1100, 1125, 1150, or 1175) when fitted to an HMM generated from the amino acid sequences set forth in FIG. 3 are identified in the Sequence Listing of this application. Such polypeptides include, for example, SEQ ID NOs: 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 1009, 1010, 1011, 1012, 1013, 1014, 1015, 1016, 1017, 1018, 1019, 1020, 1021, 1022, and 1023.

Examples of polypeptides are shown in the sequence listing that have HMM bit scores greater than 79 (e.g., greater than 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, or 620) when fitted to an HMM generated from the amino acid sequences set forth in FIG. 4 are identified in the Sequence Listing of this application. Such polypeptides include, for example, SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, and 1008.

Examples of polypeptides are shown in the sequence listing that have HMM bit scores greater than 65 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 5 are identified in the Sequence Listing of this application. Such polypeptides include, for example, SEQ ID NOs: 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273.

Examples of polypeptides are shown in the sequence listing that have HMM bit scores greater than 352 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 6 are identified in the Sequence Listing of this application. Such polypeptides include, for example, SEQ ID NOs: 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, and 1541.

Examples of polypeptides are shown in the sequence listing that have HMM bit scores greater than 57 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 7 are identified in the Sequence Listing of this application. Such polypeptides include, for example, SEQ ID NOs: 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567.

Examples of polypeptides are shown in the sequence listing that have HMM bit scores greater than 399 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 8 are identified in the Sequence Listing of this application. Such polypeptides include, for example, SEQ ID NOs: 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, and 1428.

Examples of polypeptides are shown in the sequence listing that have HMM bit scores greater than 259 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 9 are identified in the Sequence Listing of this application. Such polypeptides include, for example, SEQ ID NOs: 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, and 1385.

D. Percent Identity

In some embodiments, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567.

Polypeptides having such a percent sequence identity often have a domain indicative of a biomass composition-modulating polypeptide and/or have an HMM bit score that is greater than 65, as discussed above Amino acid sequences of biomass composition-modulating polypeptides having at least 80% sequence identity to one of the amino acid sequences set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567 are provided in FIGS. 1-9 and in the Sequence Listing.

"Percent sequence identity" refers to the degree of sequence identity between any given reference sequence, e.g., SEQ ID NO: 1, and a candidate biomass composition-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 471. Amino acid sequences of polypeptides having greater than 45% sequence identity to the polypeptide set forth in SEQ ID NO: 471 are provided in FIG. 1 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 99. Amino acid sequences of polypeptides having greater than 45% sequence identity to the polypeptide set forth in SEQ ID NO: 99 are provided in FIG. 2 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 188. Amino acid sequences of polypeptides having greater than 45% sequence identity to the polypeptide set forth in SEQ ID NO: 188 are provided in FIG. 3 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1. Amino acid sequences of polypeptides having greater than 45% sequence identity to the polypeptide set forth in SEQ ID NO: 1 are provided in FIG. 4 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 287. Amino acid sequences of polypeptides having greater than 45% sequence identity to the polypeptide set forth in SEQ ID NO: 287 are provided in FIG. 5 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1429. Amino acid sequences of polypeptides having greater than 45% sequence identity to the polypeptide set forth in SEQ ID NO: 1429 are provided in FIG. 6 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1542. Amino acid sequences of polypeptides having greater than 45% sequence identity to the polypeptide set forth in SEQ ID NO: 1542 are provided in FIG. 7 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1386. Amino acid sequences of polypeptides having greater than 45% sequence identity to the polypeptide set forth in SEQ ID NO: 1386 are provided in FIG. 8 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1274. Amino acid sequences of polypeptides having greater than 45% sequence identity to the polypeptide set forth in SEQ ID NO: 1274 are provided in FIG. 9 and in the Sequence Listing.

E. Other Sequences

It should be appreciated that a biomass composition-modulating polypeptide can include additional amino acids that are not involved in biomass modulation, and thus such a polypeptide can be longer than would otherwise be the case. For example, a biomass composition-modulating polypeptide can include a purification tag, a chloroplast transit peptide, a mitochondrial transit peptide, an amyloplast peptide, or a leader sequence added to the amino or carboxy terminus. In some embodiments, a biomass composition-modulating polypeptide includes an amino acid sequence that functions as a reporter, e.g., a green fluorescent protein or yellow fluorescent protein.

IV. Nucleic Acids

Nucleic acids described herein include nucleic acids that are effective to modulate biomass composition when transcribed in a plant or plant cell. Such nucleic acids include, without limitation, those that encode a biomass composition-modulating polypeptide and those that can be used to inhibit expression of a biomass composition-modulating polypeptide via a nucleic acid based method.

A. Nucleic Acids Encoding Biomass Composition-Modulating Polypeptides

Nucleic acids encoding biomass composition-modulating polypeptides are described herein. Examples of such nucleic acids include SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Biomass Composition-Modulating Polypeptide A nucleic acid encoding one of the biomass composition-modulating polypeptides described herein (e.g., a polypeptide set forth in FIG. 1 or a functional homolog thereof, a polypeptide set forth in FIG. 2 or a functional homolog thereof, or a polypeptide set forth in FIG. 4 or a functional homolog thereof, a polypeptide set forth in FIG. 6 or a functional homolog thereof, a polypeptide set forth in FIG. 8 or a functional homolog thereof, or a polypeptide set forth in FIG. 9 or a functional homolog thereof) can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular biomass composition-modulating polypeptide; i.e., for many amino acids, there is more than one nucleotide triplet that serves as the codon for the amino acid. Thus, codons in the coding sequence for a given biomass composition-modulating polypeptide can be modified such that optimal expression in a particular plant species is obtained, using appropriate codon bias tables for that species.

In some cases, expression of a biomass composition-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Biomass Composition-Modulating Polypeptide

Polynucleotides and recombinant constructs described herein can be used to inhibit expression of a biomass composition-modulating polypeptide (e.g. a polypeptide set forth in FIG. 3 or a functional homolog thereof, or a polypeptide set forth FIG. 5 or a functional homolog thereof) in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding biomass composition-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a biomass composition-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the biomass composition-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a biomass composition-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the biomass composition-modulating polypeptide. In other embodiments, one strand of the stem portion of a double stranded RNA comprises a sequence that is similar or identical to the sequence of an intron, or a fragment thereof, in the pre-mRNA encoding a biomass composition-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a biomass composition-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a biomass composition-modulating polypeptide, or a fragment of such sequences. In some embodiments, the sense or antisense sequence is identical or complementary to a sequence of the regulatory region that drives transcription of the gene encoding a biomass composition-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a biomass composition-modulating polypeptide described herein. The sense sequence complementary to the antisense sequence can be a sequence present within the mRNA of the biomass composition-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.,* 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, e.g., U.S. Patent Publication No. 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate biomass composition. A recombinant nucleic acid construct can comprise a nucleic acid encoding a biomass composition-modulating polypeptide as described herein, operably linked to a regulatory region suitable for expressing the biomass composition-modulating polypeptide in the plant or cell. Thus, in one embodiment a nucleic acid can comprise a coding sequence that encodes a biomass composition-modulating polypeptides as set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567.

Examples of nucleic acids encoding biomass composition-modulating polypeptides are set forth in SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265, or in the Sequence Listing. The biomass composition-modulating polypeptide encoded by a recombinant nucleic acid can be a native biomass composition-modulating polypeptide, or can be heterologous to the cell. In some cases, the recombinant construct contains a nucleic acid that inhibits expression of a biomass composition-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; Ser. Nos. 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao, *Plant Mal. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as gibberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and promoters used with Cry1A(b) and Cry1A(c) (Braga et al. 2003, *Journal of New Seeds* 5:209-221).

xii. Other Promoters

Other classes of promoters include, but are not limited to, shoot-preferential, callus-preferential, trichrome cell-preferential, guard cell-preferential such as PT0678, tuber-preferential, parenchyma cell-preferential, and senescence-preferential promoters. In some embodiments, a promoter may preferentially drive expression in reproductive tissues (e.g., PO2916 promoter, SEQ ID NO:31 in 61/364,903). Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a biomass composition-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

V. Sequences of Interest

Plants and cells described herein can also have a second exogenous nucleic acid that comprises a sequence of interest, which is preselected for its beneficial effect upon a trait of commercial value. An exogenous nucleic acid comprising a sequence of interest is operably linked to a regulatory region for transformation into plants, and plants are selected whose expression of the sequence of interest achieves a desired amount and/or specificity of expression. A suitable regulatory region is chosen as described herein. In most cases, expression of a sequence of interest is regulated independently of biomass composition-modulating sequences in plants. It will be appreciated, however, that in some embodiments expression of a sequence of interest is regulated by transcription factors that regulate biomass composition-modulating sequences as described herein.

A sequence of interest can encode a polypeptide or can regulate the expression of a polypeptide. A sequence of interest that encodes a polypeptide can encode a plant polypeptide, a non-plant polypeptide such as a mammalian polypeptide, a modified polypeptide, a synthetic polypeptide, or a portion of a polypeptide. In some embodiments, a sequence of interest is transcribed into an antisense or interfering RNA molecule.

More than one sequence of interest can be present in a plant, e.g., two, three, four, five, six, seven, eight, nine, or ten sequences of interest can be present in a plant. Each sequence of interest can be present on the same nucleic acid construct or can be present on separate nucleic acid constructs. The regulatory region operably linked to each sequence of interest can be the same or can be different.

Sequences of interest that can be used in the methods described herein include, but are not limited to, sequences encoding genes or fragments thereof that modulate cold tolerance, frost tolerance, heat tolerance, drought tolerance, water used efficiency, nitrogen use efficiency, pest resistance, biomass, chemical composition, plant architecture, and/or biofuel conversion properties. In particular, exemplary sequences are described in the following applications which are incorporated herein by reference in their entirety: US20080131581, US20080072340, US20070277269, US20070214517, US 20070192907, US 20070174936, US 20070101460, US 20070094750, US20070083953, US 20070061914, US20070039067, US20070006346, US20070006345, US20060294622, US20060195943, US20060168696, US20060150285, US20060143729, US20060134786, US20060112454, US20060057724, US20060010518, US20050229270, US20050223434, US20030217388, WO 2011/011412, WO 2010/033564, and WO2009/102965.

VI. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a biomass composition-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of biomass. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a biomass composition relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Cokhicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis,*

*Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (*eucalyptus*), *Triticosecale* (*triticum*—wheat X rye) and bamboo.

Suitable species also include *Helianthus annuus* (sunflower), *Carthamus tinctorius* (safflower), *Jatropha curcas* (*Jatropha*), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include *Rosa* spp. (rose), *Dianthus caryophyllus* (carnation), *Petunia* spp. (*petunia*) and *Poinsettia pulcherrima* (poinsettia). Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum,* or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus*x *giganteus, Miscanthus sinensis, Miscanthus* x *ogiformis, Miscanthus floridulus, Miscanthus transmorrisonensis, Miscanthus oligostachyus, Miscanthus nepalensis, Miscanthus sacchariflorus, Miscanthus* x *giganteus 'Amuri', Miscanthus* x *giganteus* 'Nagana', *Miscanthus* x *giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Pat. No. PP14,743), *Miscanthus* var. 'Gold bar' (U.S. Pat. No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. PP13, 008), *Miscanthus* var. 'Lottum', *Miscanthus* var. 'Malepartus', *Miscanthus* var. 'Morning Light', *Miscanthus* var. 'Mysterious Maiden' (U.S. Pat. No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen'(aka 'Little Dot'), *Miscanthus* var. 'Rigoletto', *Miscanthus* var. 'Sarabande', *Miscanthus* var. 'Silberpfeil' (Aka. Silver Arrow), *Miscanthus* var. 'Silverstripe', *Miscanthus* var. 'Super Stripe' (U.S. Pat. No. PP18, 161), *Miscanthus* var. 'Strictus', or *Miscanthus* var. 'Zebrinus'.

In some embodiments, a suitable species can be a wild, weedy, or cultivated sorghum species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum*

*virgatum, Sorghum vulgare*, or hybrids such as *Sorghum* x *almum, Sorghum* x *sudangrass* or *Sorghum* x *drummondii*.

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (Miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. X *Miscanthus* sp., *Sorghum* sp. X *Miscanthus* sp., e.g., *Panicum virgatum* x *Panicum amarum, Panicum virgatum* x *Panicum amarulum*, and *Pennisetum purpureum* x *Pennisetum typhoidum*).

D. Transgenic Plant Phenotypes

In some embodiments, a plant in which expression of a biomass composition-modulating polypeptide is modulated has increased or decreased levels of sugar, ash, or glucan content. A plant in which expression of a biomass composition-modulating polypeptide is modulated also can have increased or decreased conversion efficiency. A component of biomass composition can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of the biomass component in a corresponding control plant that does not express the transgene. In some embodiments, a plant in which expression of a biomass composition-modulating polypeptide is modulated can have decreased levels of a biomass component. The level can be decreased by at least 2 percent, e.g., 2, 3, 4, 5, 10, 15, 20, 25, 30, 35, or more than 35 percent, as compared to the level in a corresponding control plant that does not express the transgene.

Increases in a component of biomass composition (e.g., total sugar content) in such plants can provide improved nutritional availability in geographic locales where intake of plant foods is often insufficient, or for energy production (e.g., conversion efficiency). In some embodiments, decreases in a component of biomass composition in such plants can be useful in energy production.

In some embodiments, a plant in which expression of a biomass composition-modulating polypeptide is modulated can have increased or decreased levels of a biomass component (e.g., sugar content) in one or more plant tissues, e.g., vegetative tissues, reproductive tissues, or root tissues. For example, the level of a biomass component can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level in a corresponding control plant that does not express the transgene. In some embodiments, a plant in which expression of a biomass composition-modulating polypeptide is modulated can have decreased levels of a biomass component in one or more plant tissues. The level can be decreased by at least 2 percent, e.g., 2, 3, 4, 5, 10, 15, 20, 25, 30, 35, or more than 35 percent, as compared to the level in a corresponding control plant that does not express the transgene.

Typically, a difference in the amount of a biomass component in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of a biomass component is statistically significant at $p<0.01$, $p<0.005$, or $p<0.001$. A statistically significant difference in, for example, the amount of a biomass component in a transgenic plant compared to the amount of a control plant indicates that the recombinant nucleic acid present in the transgenic plant results in altered biomass composition.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be measured as described in the examples section. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. $DMY=((100-M)/100)*FMW$. Biomass can be quantified as fresh matter yield, which is the mass of biomass produced (usually reported in T/acre) on an as-received basis, which includes the weight of moisture.

VII. Modifying Endogenous Nucleic Acids Encoding Biomass Composition-Modulating Polypeptides This document also features plant cells and plants in which an endogenous biomass composition-modulating nucleic acid described herein has been modified (e.g., a regulatory region, intron, or coding region of the biomass composition-modulating nucleic acid has been modified). The biomass composition of such plants is altered relative to the corresponding composition of a control plant in which the endogenous nucleic acid is not modified. Such plants are referred to herein as modified plants and may be used to produce, for example, increased amounts of a biomass component (e.g., total sugar content).

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.*, 57:747-757 (2009); and Lloyd et al., *Proc. Natl. Acad. Sci. USA*, 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution). In some embodiments, site directed mutagenesis is achieved via non-homologous end joining such that after breaking DNA, endogenous DNA repair mechanisms ligate the break, often introducing slight deletions or additions that can be screened at the cell or plant level for desired phenotypes. Moore and Haber, *Mol Cell Biol.*, 16(5):2164-73 (1996).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA*, 106(5): 1660-1665 (2009); and Li et al., *Proc Natl Acad Sci USA*, 103(46):17337-42 (2006). In some embodiments, ZFNs engineered to create DNA double strand breaks at specific loci can be used to insert a DNA fragment having at least one region that overlaps with the endogenous DNA to facilitate homologous recombination, such that the non-overlapping portion of the DNA fragment is integrated at the break site. For example, a fragment can be inserted into an endogenous promoter and/or regulatory region at a specific site where a ZFN created a double stranded break to alter the expression of an endogenous gene. For example, a fragment that is inserted into an endogenous gene coding region at a specific site where a ZFN created a double stranded break can result in expression of a chimeric gene. For example, a fragment that functions as a regulatory region or promoter that is inserted into an endogenous DNA region immediately upstream of a gene coding sequence at a specific site where a ZFN creates a double strand break can result in altered expression of the endogenous gene.

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology*, 122:1003-1013 (2000).

In some embodiments, endogenous nucleic acids can be modified by introducing all engineered transcription activation/repression factor (e.g., zinc finger protein transcription factor, or ZFP TF. See, for example, the world wide web at sangamo.com/tech/tech_plat_over.html#whatarezfp). For example, a synthetic transcription facto sequence of a zinc finger DNA binding domain and a VP16 activation domain can be designed to bind to a specific endogenous DNA site and alter expression of an endogenous gene. An engineered transcription activation/repression factor (such as ZFP TF) can activate, repress, or switch the target endogenous biomass, sucrose, and/or conversion-gene expression by binding specifically to the promoter region or coding region of the endogenous gene.

Engineered nucleases that cleave specific DNA sequences in vivo can also be valuable reagents for targeted mutagenesis. One such class of sequence-specific nucleases can be created by fusing transcription activator-like effectors (TALEs) to the catalytic domain of the FoId endonuclease. Both native and custom TALE-nuclease fusions direct DNA double-strand breaks to specific, targeted sites. Christian, et al., *Genetics* 186: 757-761 (2010).

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet* 5(2):145-50 (2004).

In some embodiments, an endogenous nucleic acid can be modified via a gene silencing technique. See, for example, the section herein regarding "Inhibition of Expression of a Biomass composition-modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of biomass. For example, a population of progeny can be screened for those plants having a desired level of expression of a biomass composition-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in biomass composition relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous biomass composition-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in a component of biomass.

As with transgenic plant cells, modified plant cells can constitute part or all of a whole plant. Such plants can be grown in the same manner as described for transgenic plants and can be bred or propagated in the same manner as described for transgenic plants.

VIII. Plant Breeding

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescein) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., Pst1). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in biomass composition. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

IX. Articles of Manufacture

Transgenic plants provided herein have various uses in the agricultural and energy production industries. For example, transgenic plants described herein can be used to make animal feed (e.g., forage products) and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher biomass yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

X. EXAMPLES

Example 1

GA 20-Oxidase Overexpressing Rice Plants

A rice plant of the Kitaake variety was transformed with a vector intended to overexpress a transgene expected to produce a known phenotype. The phenotype of one transformation event unexpectedly showed a dramatic increase in height. Sequencing of the rice genomic DNA flanking the vector insertion site revealed that the insertion occurred about 8 kb 5' of the OsGA20ox1 gene. Overexpression of the OsGA20ox1 sequence was observed by RT-PCR. The morphology of the transformed plant was very similar to one previously reported for activation-tagged and transgenic OsGA20ox1 overexpressing rice plants (sec Oikawa, et al., 2004, supra). These results indicated that the increase in height and the morphology observed for this plant were due to trans-activation of the rice OsGA20ox1 gene rather than expression of the transgene per se.

Rice plants of the Kitaake variety were transformed separately with a vector to overexpress the transgene encoding a GA20-oxidase enzyme CeresAnnot: 8631464 (SEQ ID NO: 473) from *Sorghum bicolor*, GID1 GA receptor gene CeresClone:1857760 (SEQ ID NO: 101) from *Panicum virgatum*, or RNAi construct (SEQ ID NO: 1568) designed to target the rice locus for SLR1, Os03g49990 (CeresAnnot: 200242600), a gene encoding a DELLA protein. The phenotype of GA20-oxidase and GID transformation events showed dramatic increases in height. For the GA20-oxidase enzyme, overexpression of the sequence was observed by RT-PCR. This analysis of expression levels was not conducted for GID1 GA receptor or SLR1 RNAi. The morphology of the plants transformed with the GA20-oxidase and GID1 GA receptor sequences was very similar to the transgenic line described above for OsGA20ox1.

Nucleic acids for GID1 GA receptor, GA20-oxidase enzyme, and SLR1 RNAi were isolated from *Panicum virgatum, Sorghum bicolor*, and *Oryza sativa*, respectively, and cloned into a Ti plasmid vector, CV2, under the control of a PD3580 promoter, which is disclosed in WO2009/146015. Each construct contained a NPTII gene which confers paramyosin resistance to transformed plants. The presence of each vector containing a nucleic acid described above in the respective transgenic rice lines transformed with the vector was confirmed by paramyosin resistance, PCR amplification from green leaf tissue extract, and/or sequencing of PCR products.

*Sorghum* plants of the Wheatland and BTx430 varieties were transformed with a vector to overexpress the transgene encoding a GA20-oxidase enzyme CeresAnnot: 8631464 (SEQ ID NO: 473) from *Sorghum bicolor*. The vector was the same as that described above for the rice transformation.

Example 2

Cellulosic Biomass Conversion Characteristics of Rice Plants Overexpressing a Rice GA 20-Oxidase The transformed plant of Example 1 that was found to overexpress the OsGA20ox1 was crossed to a wild type rice plant. The progeny of the cross segregated 1:1 for the transgene and morphological phenotype. Biomass of transgenic (RiceS-1 No. 2 and RiceS-1 No. 4) and non-transgenic segregants (RiceS-1 No. 10) was harvested at maturity (after three months of growth) and subjected to a conversion assay as follows.

The yield of conversion can be directly calculated as follows: [PLN value+SAC value]/amount of biomass weight, where "PLN" refers to pretreatment liquor neutralized, and "SAC" refers to the sugar value from the saccharification analysis. The following procedures were used to obtain the PLN and SAC values.

Sample preparation and milling: Samples were prepared for analysis by drying the tissue samples for at least 3 days in an incubator set at 45° C. Dried tissues were milled using a Wiley Mill fitted with 2 mm mesh filter.

Microwave pretreatment: Milled tissues were weighed to obtain approximately 0.025 g. The moisture content of the weighed tissues was determined using the Denver Moisture Content analyzer. Tissues were transferred into separate Biotage microwave vials that were previously tared. Appropriate volume of sulfuric acid was then added into the samples to give a final concentration of 1.3% (w/w) in aqueous solution. Samples were pretreated in the Biotage microwave using the following settings: 160° C., 5 minutes, very high absorbance, 2.0-5.0 vial, 600 rpm stir speed (SWAVE default). The vials with the microwaved samples were centrifuged at 4000 rpm for 5 min with a deceleration rate set at ≤5. A minimum of 4 ml of PL (pretreated liquor) from each vial was transferred into pre-labeled 15 ml Corning conical tubes. The pH of the PL fraction was measured. The PL was directly neutralized with calcium carbonate ($CaCO_3$) for PLN and subsequent HPLC analysis or kept frozen until ready to analyze. The solid residue in each vial was washed several times by adding 5 ml water followed by centrifugation step at 4000 rpm for 5 min. The pH of the wash was monitored until it reached between 5 and 6 using appropriate pH indicator strips. The solid fraction was stored for saccharification analysis.

Pretreatment Liquor Analysis: To determine PLN, calcium carbonate ($CaCO_3$) was added to an appropriate aliquot of each PL fraction until its pH reached between 5 and 6. The neutralized mixture was centrifuged at 4000 rpm for 2 min; after which 2 ml of the neutralized liquor was transferred to storage tubes.

To determine the amount of sugar released after acid pretreatment, the neutralized fraction (PLN) was analyzed by HPLC. Table 1 presents the amount of glucose (GLC) and xylose (XYL) released as PLN mg GLC/g dry biomass and PLN mg XYL/g dry biomass for the transgenic (RiceS-1 No. 2 and No. 4) and wild-type (RiceS-1 No. 10) plants.

Saccharification Analysis: Water was added to the solid fraction obtained from the microwave pretreatment. A solution of citrate buffer (50 mM final), tetracycline (0.04 mg/mL final), cycloheximide (0.03 mg/mL final), Spezyme® and Novozyme 188 was added to make 20 mg or 2 mg enzyme/g dry biomass. The reaction mixture was then incubated at 50° C. in a rotating incubator. After 24 hours of incubation, an aliquot from the reaction was transferred to a microcentrifuge tube. The reaction was stopped by boiling the mixture for 5 min. The mixture was centrifuged for 2 min at 14,000 rpm. The supernatant was removed for sugar analysis (glucose monomers) by HPLC. Table 1 presents the amount of glucose (GLC) and xylose (XYL) released after enzymatic hydrolysis as SAC mg GLC/g dry biomass and SAC mg XYL/g dry biomass for the transgenic (RiceS-1 No. 2 and No. 4) and wild-type (RiceS-1 No. 10) plants. Table 1 also presents the total glucose and total xylose released (total from the PLN and SAC assays) for the transgenic and wild-type plants.

TABLE 1

| Sample (mg enzyme) | SAC mg GLC/g dry biomass | SD | SAC mg XYL/g dry biomass | SD |
|---|---|---|---|---|
| RiceS-1 No. 2 (20) | 221.5 | 3.9 | 6.5 | 0.4 |
| RiceS-1 No. 2 (2) | 134.1 | 3.3 | 0.2 | 0.3 |
| RiceS-1 No. 4 (20) | 202.4 | 1.8 | 4.6 | 0.2 |
| RiceS-1 No. 4 (2) | 124.3 | 3.5 | 0.4 | 0.1 |
| RiceS-1 No. 10 (20) | 280.1 | 4.9 | 7.6 | 0.4 |
| RiceS-1 No. 10 (2) | 143.0 | 0.0 | 0.3 | 0.3 |

| Sample | PLN mg GLC/g dry biomass | SD | PLN mg XYL/g dry biomass | SD |
|---|---|---|---|---|
| RiceS-1 No. 2 (20) | 154.1 | 11.6 | 124.4 | 0.6 |
| RiceS-1 No. 2 (2) | 168.1 | 3.8 | 120.9 | 1.6 |
| RiceS-1 No. 4 (20) | 209.4 | 4.2 | 114.0 | 2.3 |
| RiceS-1 No. 4 (2) | 211.7 | 2.6 | 117.2 | 3.8 |
| RiceS-1 No. 10 (20) | 28.5 | 0.1 | 155.3 | 1.6 |
| RiceS-1 No. 10 (2) | 25.1 | 0.2 | 146.0 | 1.4 |

| Sample | Total Glucose release | SD | Total Xylose release | SD |
|---|---|---|---|---|
| RiceS-1 No. 2 (20) | 375.6 | 15.5 | 130.9 | 1.0 |
| RiceS-1 No. 2 (2) | 302.2 | 7.1 | 121.1 | 1.9 |
| RiceS-1 No. 4 (20) | 411.8 | 6.0 | 118.6 | 2.5 |
| RiceS-1 No. 4 (2) | 336.0 | 6.1 | 117.6 | 3.9 |
| RiceS-1 No. 10 (20) | 308.6 | 5.0 | 162.9 | 2.0 |
| RiceS-1 No. 10 (2) | 168.1 | 0.2 | 146.3 | 1.7 |

Example 3

Cellulosic Biomass Conversion Characteristics of Rice Plants Overexpressing a GA 20-Oxidase Sequence from Sorghum Bicolor The transformed rice plants of Example 1 overexpressing the GA 20-oxidase sequence from *Sorghum bicolor* (SEQ ID NO:473) were analyzed for cellulosic biomass conversion characteristics. All plants were of the primary transformant generation, T0. Control plants included plants derived from the same transformation procedure as the transgenic lines but that tested negative for PCR products associated with the transgenes.

The yield of conversion can be directly calculated as follows: [PLN value+SAC value]/amount of biomass weight, where "PLN" refers to pretreatment liquor neutralized, and "SAC" refers to the sugar value from the saccharification analysis. The following procedures were used to obtain the PLN values.

Sample preparation and milling, microwave pretreatment, and pretreatment liquor analysis for GLC only were carried out as described in Example 2.

Saccharification Analysis: Water was added to the solid fraction obtained from the microwave pretreatment. A solution of citrate buffer (50 mM final), tetracycline (0.04 mg/ml final), cycloheximide (0.03 mg/ml final), Novozyme CTec2 was added to make 20 mg, 2 mg, or 1 mg enzyme/g dry biomass. The reaction mixture was then incubated at 50° C. in a rotating incubator. After 24 hours of incubation, an aliquot from the reaction was transferred to a microcentrifuge tube. The reaction was stopped by boiling the mixture for 5 min. The mixture was centrifuged for 2 min at 14,000 rpm. The supernatant was removed for sugar analysis (glucose monomers) by HPLC.

Determining Sucrose and Glucose in dry biomass: Accelerated Solvent Extractor (Dionex ASE 200) cells (22 ml stainless steel cells, Cat no. 049561) were filled with milled biomass (2 mm). Samples were loaded in ASE 200 and both sucrose and glucose compounds in the biomass were extracted using water as a solvent. During the extraction, the cells were filled with water and heated to 100° C. and 1500 psi pressure. The extracts were collected in vials. Volume of the extracts was measured accurately and a homogenized subset of the sample was used to run HPLC to determine the sugar profile.

Two sets of samples were used to characterize the sugars extractable in pretreatment. For one sample set, sucrose and glucose were extracted and measured as explained above to determine the SUG value in Table 2, which is the sum of free glucose and glucose theoretically generated by sucrose hydrolysis. The other sample set was subjected to PLN analysis to determine total glucose (GLC in the PLN group) in Table 2.

HPLC: The neutralized sample from PLN and extracts from ASE were run on HPLC (Agilent 1100 series) to determine the sugar profile. A HPLC carbohydrate analysis column (Aminex® HPX-87P column) was used for the sugar analysis. The column was heated at 80° C. and the flow rate was set at 0.6 ml/min and 1 ml/min for analyzing PLN and ASE extracts, respectively. Corona® CAD® detector (Thermo Scientific) was used to analyze the sugar samples. The data was analyzed using Agilent Chemstation software.

Table 2 presents the amount of glucose (GLC) released after both pretreatment (PLN GLC) and saccharification enzymatic hydrolysis (SAC GLC) as determined for three separate enzyme dose levels (20 mg, 10 mg, and 1 mg) for transgenic and non-transgenic control plants. The GLC from PLN, SUG, and associated standard deviations (SD) were determined based on two replicate samples from a single plant for each enzyme dose level for a total of six samples. CW/Starch (mg/gDry biomass) was then calculated by subtracting the SUG from the GLC to determine the remaining amount of glucose from cell wall release and starch combined. Subsequent evaluations demonstrated that the starch only accounts for a small proportion of the PLN (CW/Starch) (see Example 4). The glucose released from saccharification and associated standard deviations (SD) were measured from two sample replicates for each enzyme dose level. The total GLC was calculated as the sum of PLN GLC and SAC GLC.

mobilization of cell wall material in pretreatment to increase PLN (CW/starch). The increase in PLN (CW/starch) increases conversion efficiency with more cell wall material released.

Example 4

Biomass Conversion Characteristics of Rice Plants Overexpressing a GID1GA Receptor Sequence from *Panicum virgatum* and Rice Plants Overexpressing an RNAi Construct for the Rice SLR1 Gene Three events of the transformed rice plants of Example 1 overexpressing the GID1 GA receptor encoding sequence (SEQ ID NO: 101) were designated Os1043-12, Os1043-13, and Os1043-18. Three events of the transformed plants of Example 1 overexpressing the SLR1 RNAi sequence (SEQ ID NO: 1568) were designated Os1044-06, Os1044-19, and Os1044-27. All plants were of the primary transformant generation, T0. Control plants included untransformed wild-type plants and plants derived from the same transformation procedure as the transgenic lines but that tested negative for PCR products associated with the transgenes.

Sample preparation, milling, microwave pretreatment, and pretreatment liquor analysis were carried out as described in Example 2 for GLC only. Determining sucrose and glucose in dry biomass, and HPLC were carried out as described in Example 3.

Determining Starch in dry biomass: Finely milled (0.5 mm) biomass was used to analyze the starch content in biomass. Megazyme Total Starch assay kit (K-TSTA) was used for determining starch content of the biomass. The absorbance for each sample was read and the D-glucose control (supplied with the kit) at 510 nm against the reagent blank using a spectrophotometer (Agilent 8453 UV-Vis).

Table 3 presents the amount of glucose (GLC) released after pretreatment (PLN GLC) and its portion released from cell wall for transgenic and control plants. The data for each event were based on the average of two tissue sample replicates for single plants. Total free glucose was determined using separate sets of samples of dry material that was

TABLE 2

| | PLN GLC | | | | SAC GLC | | | |
|---|---|---|---|---|---|---|---|---|
| | GLC (mg/gDry biomass) | SUG (mg/gDry biomass) | CW/Starch (mg/gDry biomass) | SD | Enzyme dose | GLC (mg/gDry biomass) | SD | Total GLC | SD |
| Control (NT) | 63.4 | 35.4 | 28.1 | 4.1 | 20 mg | 211.6 | 1.2 | 275.0 | 5.3 |
| | 63.4 | 35.4 | 28.1 | 4.1 | 2 mg | 158.7 | 10.3 | 222.1 | 14.4 |
| | 63.4 | 35.4 | 28.1 | 4.1 | 1 mg | 136.8 | 14.8 | 200.3 | 18.9 |
| Transgenic | 182.2 | 91.6 | 90.6 | 7.8 | 20 mg | 179.7 | 6.5 | 361.9 | 14.3 |
| | 182.2 | 91.6 | 90.6 | 7.8 | 2 mg | 143.2 | 2.3 | 325.4 | 10.1 |
| | 182.2 | 91.6 | 90.6 | 7.8 | 1 mg | 115.3 | 8.4 | 297.5 | 16.2 |

The results demonstrate that the total glucose released increased in transgenic rice plants overexpressing the GA 20-oxidase sequence from *Sorghum bicolor* in comparison to non-transgenic control plants. This increase is based on the significant increases in sugar and glucose release from pretreatment alone (PLN SUG and GLC) and in a greater placed in aqueous solution and run through HPLC analyses, then total free glucose was calculated by adding half of the sucrose to the glucose measured (HPLC data not shown). Glucose from cell wall was calculated by subtracting the total free sugar value and the total starch value from the PNL glucose value.

TABLE 3

| Samples | PLN GLC (mg/gDry biomass) | PLN (SD) | Total free GLC (mg/gDry biomass) | Total Starch (mg/gDry biomass) | GLC from Cell Wall (mg/gDry biomass) | Plant height (cm) | Heading time (days) |
|---|---|---|---|---|---|---|---|
| WT | 84.8 | 4.1 | 47.5 | 18.6 | 18.7 | 97 | 41 |
| PCR - | 79.4 | 8.0 | 46.0 | 16.4 | 17.0 | 81 | 39 |
| Os1043-12 | 61.8 | 7.0 | 20.9 | 12.5 | 28.4 | 126 | 40 |
| Os1043-13 | 68.7 | 4.7 | 30.0 | 07.6 | 31.1 | 116 | 41 |
| Os1043-18 | 99.8 | 3.5 | 39.8 | 21.7 | 38.3 | 118 | 41 |
| Os1044-06 | 117.5 | 0.0 | 40.8 | 22.9 | 53.8 | 100 | 44 |
| Os1044-19 | 63.3 | 0.7 | 31.9 | 13.0 | 18.4 | 89 | 38 |
| Os1044-27 | 110.1 | 6.7 | 38.2 | 30.4 | 41.5 | 93 | 41 |

The results demonstrate that the total glucose released by pretreatment from cell wall increased in transgenic rice plants overexpressing the GID1 GA receptor sequence from *Panicum virgalum* or the RNAi construct targeting SLR1 in comparison to control plants. This increase is based on the significant increase in sugar release from a greater mobilization of cell wall material in pretreatment to increase glucose from the cell wall. The increase in availability of sugars from cell wall improves conversion characteristics.

Example 5

Sugar Characteristics of *Sorghum* Plants Overexpressing GA 20-Oxidase Sequence from *Sorghum Bicolor*

Four events of the transformed sorghum plants of Example 1 overexpressing the GA20-oxidase enzyme from *Sorghum bicolor* (SEQ ID NO:473) were designated SbGA20-054, SbGA20-071, SbGA20-048, and SbGA20-52. All plants were of the primary transformant generation, T0, in the sorghum variety Wheatland. Control plants were of the Wheatland variety and grown from seed. SbGA20-054 was treated as a negative control based on short height phenotype that matched the control.

Five stalk juice samples were harvested at approximately soft to hard dough stages. After harvesting, the Brix value of each juice sample was measured. HPLC was carried out as described in Example 3, except that juice samples were used instead of dry material derived samples and the amount of fructose (FRU) was also measured.

Table 4 presents the Brix and HPLC-determined sugar profiles from juice samples of transgenic and control plants. The data for each event were based on one juice sample for single plants.

respectively, although an increase in sugar concentration was seen in all cases. Combining stature and juice yield with sugar profile, the significant advantage of increased sugar yield associated with the transgenic events becomes apparent in comparison to the controls.

Example 6

*Sorghum* seeds are planted in the field and allowed to germinate. At 2 week intervals following planting, the field is sprayed with GA3 at the rate of 50 g per hectare. Biomass of sorghum plants from the field is harvested about four months after planting. The biomass is subjected to a cellulosic sugar extraction process (see Example 2) for use in ethanol fermentation. The process results in increased sugars and/or requires lower amounts of the saccharification enzyme cocktail for sugar release per unit biomass, as compared to similar processing of biomass of sorghum plants of the same variety grown in under the same field conditions except for gibberellin treatment.

Example 7

*Miscanthus* plantlets are transplanted to a field. At 2 week intervals during the second growing season, the field is sprayed with GA3 at a rate of 50 gm per hectare. Biomass from the field is harvested and subjected to a pretreatment and enzymatic saccharification process (see Example 2). The process yields increased sugars and/or requires lower amounts of the saccharification enzyme cocktail for sugar release per unit biomass, as compared to similar processing of biomass of *Miscanthus* plants of the same variety grown in under the same field conditions except for gibberellin treatment.

TABLE 4

| Stature | Sample | PCR | Brix % | SUC (mg/ml) | GLC (mg/ml) | FRU (mg/ml) | Total (mg/ml) | Sucrose Purity (%) | Juice volume (ml juice/ Stalk) | Sugar Yield (mg sugar/ Stalk) |
|---|---|---|---|---|---|---|---|---|---|---|
| Control (Short) | Wheatland | - | 6.5 | 13.1 | 0.7 | 0.2 | 14.0 | 93.7% | 27.5 | 385.8 |
| Short | SbGA20-054 | + | 13.3 | 71.8 | 2.1 | 1.5 | 75.3 | 95.3% | 7.5 | 564.9 |
| Tall | SbGA20-071 | + | 11.2 | 69.5 | 2.2 | 1.5 | 73.2 | 95.0% | 25.0 | 1830.8 |
| Tall | SbGA20-048 | + | 14.2 | 82.1 | 2.2 | 1.7 | 86.0 | 95.4% | 40.0 | 3442.0 |
| Tall | SbGA20-052 | + | 7.6 | 30.7 | 1.5 | 1.1 | 33.3 | 92.2% | 75.0 | 2495.3 |

The SbGA20-071, SbGA20-048, SbGA20-052 transgenic lines all showed an increase in plant height in comparison to control plants.

Total sugar values for SbGA20-054 and SbGA20-052 deviated from the expected trend at 75.3 and 33.3 mg/ml, Example 8

Switchgrass seeds are planted in the field and allowed to germinate. At 2 week intervals during the third growing season, the field is sprayed with GA3 at the rate of 50 gm per hectare. Biomass from the field is harvested and subjected to a pretreatment and enzymatic saccharification process. The process yields increased sugars and/or requires lower amounts of the saccharification enzyme cocktail for sugar release per unit biomass, as compared to similar processing of biomass of switchgrass plants of the same variety grown in under the same field conditions except for gibberellin treatment.

Example 9

Sugarcane stalk cuttings are transplanted to a field. At 2 week intervals during the growing season, the field is sprayed with GA3 at a rate of 50 gm per hectare. Biomass from the field is harvested and subjected to a pretreatment and enzymatic saccharification process (see Example 2). The process yields increased sugars and/or requires lower amounts of the saccharification enzyme cocktail for sugar release per unit biomass, as compared to similar processing of biomass of sugarcane plants of the same variety grown in under the same field conditions except for gibberellin treatment.

Example 10

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 471, 99, 188, 1, 287, 1429, 1542, 1386, and 1274 are shown in FIGS. 1-9, respectively. Additional exemplary homologs are correlated to certain Figures in the Sequence Listing.

Example 11

Determination of Functional Homologs by Hidden Markov Models

Hidden Markov Models (HMMs) were generated by the program HMMER 3.0. To generate each HMM, the default HMMER 3.0 program parameters were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 471.

The procedure above was repeated and an HMM was generated for each group of sequences shown in FIGS. 1-9, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11299747B2). An electronic copy of the "Sequence Listing" will also be available from the USPTO upon request and payment of the fee set forth in 37 CFR 1.19(b)(3).

What is claimed is:

1. A rice plant comprising an exogenous nucleic acid said exogenous nucleic acid comprising a regulatory region operably linked to a nucleotide sequence encoding a polypeptide having 90 percent or greater sequence identity to the amino acid sequence of SEQ ID NO:473, wherein the rice plant is selected for having a biomass with increased saccharification efficiency relative to the corresponding saccharification efficiency of a biomass of a control plant that does not comprise said exogenous nucleic acid.

2. The rice plant of claim 1, wherein the polypeptide comprises the amino acid sequence of SEQ ID NO:473.

3. A method of producing a rice plant, said method comprising
growing rice plant comprising an exogenous nucleic acid, said exogenous nucleic acid comprising a regulatory region operably linked to a nucleotide sequence encoding a polypeptide having 90 percent or greater sequence identity to the amino acid sequence of SEQ ID NO:473,
selecting the rice plant for having increased saccharification efficiency as compared to the corresponding saccharification efficiency of a control plant that does not comprise said nucleic acid.

4. The rice plant of claim 1, wherein the plant is selected for having a biomass with increased saccharification efficiency, resulting in an at least 2.0 fold increase in glucose, fructose, and sucrose, relative to the saccharification efficiency of a biomass of a control plant that does not comprise said nucleic acid, and wherein the regulatory region is heterologous with respect to the nucleotide sequence.

5. The rice plant of claim 4, wherein the plant is selected for having an increase in sugar concentration relative to a control plant that does not comprise said nucleic acid.

6. The rice plant of claim 4, wherein the plant is further selected for having an increase in plant height relative to a control plant that does not comprise said nucleic acid.

7. The method of claim 3, wherein selecting said plant comprises selecting said plant for having an increase in sugar concentration relative to a control plant that does not comprise said nucleic acid.

8. The method of claim 7, wherein the plant is selected for having an at least a 1.5 fold, a 2.0 fold, or a 2.5 fold increase in glucose from cell wall as compared to that of a control plant that does not comprise said exogenous nucleic acid.

9. The method of claim 7, wherein the plant is selected for having an at least a 3 fold, a 4 fold, or a 6 fold increase in sugar yield as compared to that of a control plant that does not comprise said exogenous nucleic acid.

10. A progeny of the rice plant of claim 1, wherein the progeny comprises the exogenous nucleic acid.

11. A seed producing the rice plant of claim 1.

* * * * *